United States Patent
Cen et al.

(10) Patent No.: US 12,391,662 B2
(45) Date of Patent: Aug. 19, 2025

(54) LIPID COMPOUNDS AND LIPID NANOPARTICLE COMPOSITIONS

(71) Applicants: RINUAGENE BIOTECHNOLOGY CO., LTD., Suzhou (CN); RINUAGENE INTERNATIONAL HK LIMITED, Kowloon (CN)

(72) Inventors: Shan Cen, Suzhou (CN); Kai Lv, Suzhou (CN); Zhenlei Yu, Suzhou (CN); Yijie Dong, Suzhou (CN)

(73) Assignees: RINUAGENE BIOTECHNOLOGY CO. LTD. (CN); RINUAGENE INTERNATIONAL HK LIMITED (CN)

( * ) Notice: Subject to any disclaimer, the term of this patent is extended or adjusted under 35 U.S.C. 154(b) by 0 days.

(21) Appl. No.: 18/675,317

(22) Filed: May 28, 2024

(65) Prior Publication Data

US 2024/0343701 A1    Oct. 17, 2024
US 2025/0145582 A2    May 8, 2025

Related U.S. Application Data

(63) Continuation of application No. PCT/CN2023/142449, filed on Dec. 27, 2023.

(30) Foreign Application Priority Data

Dec. 28, 2022 (WO) ................ PCT/CN2022/143065
Oct. 13, 2023  (WO) ................ PCT/CN2023/124515
Dec. 25, 2023  (CN) ............................ 202311790946.8

(51) Int. Cl.
| | | |
|---|---|---|
| C07D 317/12 | (2006.01) | |
| A61K 9/51 | (2006.01) | |
| A61K 45/06 | (2006.01) | |
| C07D 319/06 | (2006.01) | |
| C07D 327/04 | (2006.01) | |
| C07D 339/06 | (2006.01) | |

(52) U.S. Cl.
CPC .......... *C07D 317/12* (2013.01); *A61K 9/5123* (2013.01); *A61K 45/06* (2013.01); *C07D 319/06* (2013.01); *C07D 327/04* (2013.01); *C07D 339/06* (2013.01)

(58) Field of Classification Search
CPC .. C07D 317/12; C07D 319/06; C07D 327/04; C07D 339/06; A61K 9/5123; A61K 45/06
See application file for complete search history.

(56) References Cited

U.S. PATENT DOCUMENTS

2022/0162521 A1    5/2022    Drummond et al.

FOREIGN PATENT DOCUMENTS

| CN | 114044741 A | 2/2022 | |
|---|---|---|---|
| CN | 114728886 A | 7/2022 | |
| CN | 114728887 A | 7/2022 | |
| CN | 114746398 A | 7/2022 | |
| JP | 02207018 A  * | 8/1990 | |
| WO | 2022216787 A2 | 10/2022 | |
| WO | 2022246555 A1 | 12/2022 | |
| WO | 2022246568 A1 | 12/2022 | |
| WO | WO-2023184038 A1 * | 10/2023 | ......... A61K 48/0041 |

OTHER PUBLICATIONS

JP02207018A Googe Patent English Translation (Year: 1990).*
Adeoluwa (Dhaka University Journal of Pharmaceutical Sciences, (2022) 20(3), 359-372.) (Year: 2022).*
Klein (Can a person prevent multiple sclerosis? Medical News Today (2020), 1-15) (Year: 2020).*
Pande (Indian J Endocr Metab 2023; 27:277-85) (Year: 2023).*

* cited by examiner

*Primary Examiner* — Kortney L. Klinkel
*Assistant Examiner* — Richard Grant Peckham
(74) *Attorney, Agent, or Firm* — Fox Rothschild LLP

(57) ABSTRACT

The present application disclosed a compound of formula (I) and a salt and a stereoisomer thereof, wherein each variable is as defined in the specification. The present application also disclosed a nanoparticle composition comprising the compound or a salt or a stereoisomer thereof, and the use of the nanoparticle composition for delivering active agents.

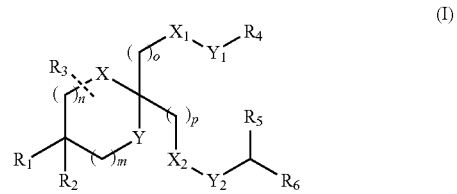

20 Claims, 5 Drawing Sheets

LIPID COMPOUNDS AND LIPID NANOPARTICLE COMPOSITIONS

CROSS-REFERENCE TO RELATED APPLICATIONS

The present application is a continuation of International Appl. No. PCT/CN2023/142449 filed Dec. 27, 2023, which claims the benefit of priority to International Appl. No. PCT/CN2022/143065 filed Dec. 28, 2022, International Appl. No. PCT/CN2023/124515 filed Oct. 13, 2023, and Chinese Appl. No. 202311790946.8 filed Dec. 25, 2023, the disclosures of all of which are hereby incorporated by reference in their entireties.

TECHNICAL FIELD

The present application relates to the field of biotechnology, and particularly to lipid compounds and lipid nanoparticle compositions. In particular, the present application relates to methods of delivering active agents, such as nucleic acids, and lipid compounds and lipid nanoparticle compositions for delivering the same.

BACKGROUND

Efficient targeted delivery of biologically active substances such as small molecule drugs, proteins and nucleic acids is a continuing medical challenge. The key to the success of gene therapy is whether it is possible to deliver the therapeutic agent via a vector into the target cell safely and effectively in vivo. Due to the relative instability of nucleic acids and the low cellular permeability of such substances, the delivery of nucleic acids to cells is difficult. Accordingly, there is a need to develop methods and compositions to facilitate the delivery of therapeutic and/or prophylactic agents, such as nucleic acids, to cells. Gene therapy vectors are classified into viral vectors and non-viral vectors. Although the viral vector is used as a highly efficient delivery system to achieve the purpose of target gene transfection and treatment, due to the problems of containing immunogenic viral proteins, limited target gene loading, high price and the like, the lipid nanoparticles (LNPs) as non-viral vectors are widely considered due to the advantages of good stability in vitro, degradability in vivo, safety and reliability, and the like, and are widely applied to gene therapy research of congenital and acquired genetic defects.

Lipid-containing nanoparticles or lipid nanoparticles, liposomes and lipid complexes have been demonstrated to be effective transport vectors to deliver biologically active substances such as small molecule drugs, proteins and nucleic acids into and/or within cells. LNPs refer to vesicles formed from one or more lipid components that are effective in compressing and delivering a variety of nucleic acid molecules, from DNA, RNA, to chromosomes, and even cells; LNP is beneficial to large-scale production due to the characteristics of a determined construction scheme, modifications for targeting a ligand easily and the like.

LNPs typically include one or more cationic lipids and/or amino (ionizable) lipids, phospholipids, structural lipids (such as cholesterol), and/or polyethylene glycol-containing lipids (PEG lipids). Cationic and/or ionizable lipids, including, for example, amine-containing lipids, can be readily protonated.

Lipid Nanoparticle (LNP) formulations represent a revolution in the field of nucleic acid delivery. Onpattro™ is an early example of a lipid nanoparticle product approved for clinical use. Onpattro™ is a lipid nanoparticle-based short interfering RNA (siRNA) pharmaceutical formulation for the treatment of polyneuropathy caused by hereditary transthyretin amyloidosis. The success of said LNP delivery system paves the way for the clinical development of the leading LNP-based COVID-19 mRNA vaccine.

The Onpattro™ LNP formulation consists of four major lipid components, namely, ionizable amino lipid MC3, Distearoyl phosphatidylcholine (DSPC), cholesterol, and polyethylene glycol conjugated lipid (PEG-lipid), in molar amounts of 50/10/38.5/1.5, respectively. The Onpattro™ is still considered as the gold standard for comparison in LNP studies Although research related to LNP-mediated nucleic acid delivery has advanced sufficiently, it is well known that the Onpattro™ formulation accumulates primarily in liver tissue. The ability of LNPs to accumulate in organs and tissues other than the liver would greatly expand the clinical utility of these delivery systems.

DISCLOSURE OF INVENTION

Based on the above, the present application discloses a lipid compound and a lipid nanoparticle composition comprising such compound, and the lipid nanoparticle has advantages of high encapsulation efficiency, low toxicity, high expression, suitability for vaccine or mRNA delivery, extrahepatic delivery, etc.

Specifically, the present application includes the following embodiments (Part I):
1. A compound of formula (I), or a salt (especially a pharmaceutically acceptable salt) or a stereoisomer thereof,

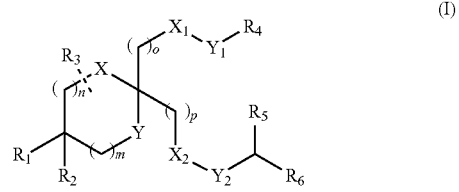

wherein
$R_1$ is

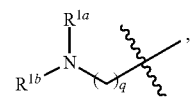

wherein $R^{1a}$ and $R^{1b}$ are independently selected from H or C1-C6alkyl, and $R^2$ and $R_3$ are independently selected from H or C1-C6alkyl, or $R_1$ and $R_2$, together with the carbon atom to which they are attached, form a substituted or unsubstituted 5-7 membered nitrogen-containing heterocyclic ring, and $R_3$ is selected from H or C1-C6alkyl, or $R_1$ and $R_3$, together with the carbon atoms to which they are attached, form ring A, which is substituted or unsubstituted 5-7 membered carbocyclic or heterocyclic ring, and $R_2$ is selected from H or C1-C6alkyl;

$R_4$, $R_5$ and $R_6$ are independently selected from C1-C14alkyl;

X and Y are independently selected from O or S;

$X_1$ and $X_2$ are independently selected from C=O or O, and $Y_1$ and $Y_2$ are independently selected from C=O or O, with the proviso that $X_1$ and $Y_1$ are not both C=O or O, and $X_2$ and $Y_2$ are not both C=O or O;

m and n are independently selected from 0, 1 or 2, with the proviso that m and n are not both 0;

o and p are independently selected from 1, 2, 3, 4, 5, 6, 7, 8, 9 or 10;

q is selected from 0, 1, 2, 3, 4, 5 or 6.

2. The compound according to item 1, or a salt (especially a pharmaceutically acceptable salt) or a stereoisomer thereof, the compound of formula (I) is of formula (IA),

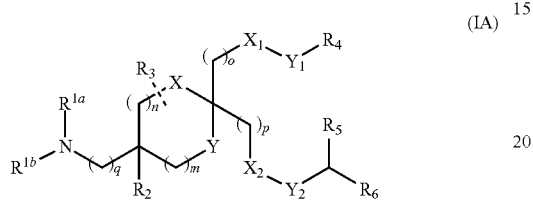

(IA)

wherein q is selected from 1, 2, 3 or 4.

3. The compound according to any one of the preceding items or a salt (especially a pharmaceutically acceptable salt), or a stereoisomer thereof, wherein $R_4$ is C9, C10, C11 or C12 linear alkyl; and $R_5$ and $R_6$ are each independently selected from C6, C7, C8 or C9 linear alkyl.

4. The compound according to any one of the preceding items or a salt (especially a pharmaceutically acceptable salt), or a stereoisomer thereof, wherein o is 5 or 6.

5. The compound according to any one of the preceding items or a salt (especially a pharmaceutically acceptable salt), or a stereoisomer thereof, wherein p is 7 or 8.

6. The compound according to any one of the preceding items or a salt (especially a pharmaceutically acceptable salt), or a stereoisomer thereof, wherein X and Y are both O.

7. The compound according to any one of the preceding items or a salt (especially a pharmaceutically acceptable salt), or a stereoisomer thereof, wherein n is 1, m is 0; or n is 1, m is 1; or n is 0, m is 1;

for example, n is 1, m is 0; for example, n is 1, m is 1.

8. The compound according to any one of the preceding items or a salt (especially a pharmaceutically acceptable salt), or a stereoisomer thereof, the compound of formula (I) being selected from the following structure

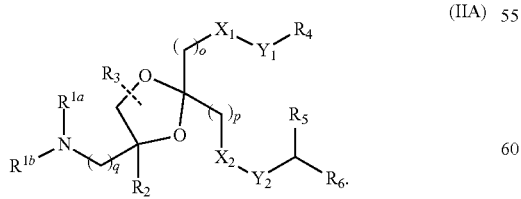

(IIA)

9. The compound according to any one of the preceding items or a salt (especially a pharmaceutically acceptable salt), or a stereoisomer thereof, the compound of formula (I) being selected from the following structure

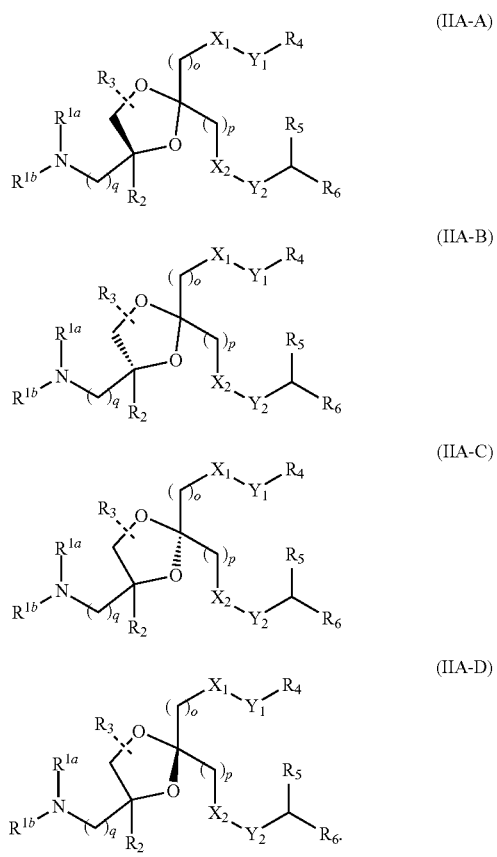

(IIA-A)

(IIA-B)

(IIA-C)

(IIA-D)

10. The compound according to any one of the preceding items or a salt (especially a pharmaceutically acceptable salt), or a stereoisomer thereof, the compound of formula (I) being selected from the following structure:

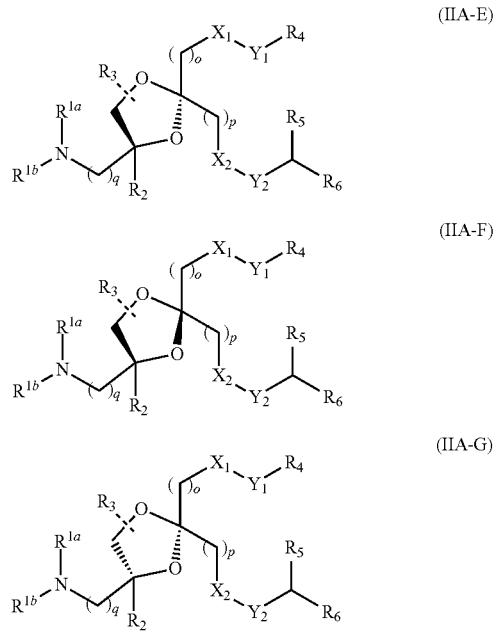

(IIA-E)

(IIA-F)

(IIA-G)

-continued

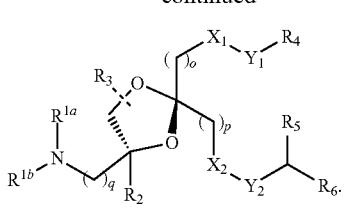

(IIA-H)

11. The compound according to any one of the preceding items or a salt (especially a pharmaceutically acceptable salt), or a stereoisomer thereof, wherein C1-C6alkyl is independently selected from —CH₃, —CH₂CH₃ or —CH(CH₃)₂;
for example, C1-C6alkyl is independently selected from —CH₃.

12. The compound according to any one of the preceding items or a salt (especially a pharmaceutically acceptable salt), or a stereoisomer thereof, wherein
$R^{1a}$ and $R^{1b}$ are independently selected from —CH₃;
$R_2$ and $R_3$ are independently selected from H;
$R_4$ is C10, C11 or C12 linear alkyl;
$R_5$ and $R_6$ are identical, and are selected from C6, C7 and C8 linear alkyl;
X and Y are independently selected from O;
$X_1$ and $X_2$ are independently selected from C=O or O, $Y_1$ and $Y_2$ are independently selected from C=O or O, with the proviso that $X_1$ and $Y_1$ are not both C=O or O, and $X_2$ and $Y_2$ are not both C=O or O;
m is 0, and n is 1;
o is 5 or 6;
p is 7 or 8, for example p is 7;
q is 2, 3 or 4, for example q is 2 or 3, for example q is 2;
for example, p is 7, and q is 2 or 3;
for example, p is 7, and q is 2.

13. The compound according to any one of items 1-12 or a salt (especially a pharmaceutically acceptable salt) or a stereoisomer thereof, wherein $X_1$ and $X_2$ are both C=O, and $Y_1$ and $Y_2$ are both O.

14. The compound according to any one of items 1-12 or a salt (especially a pharmaceutically acceptable salt) or a stereoisomer thereof, wherein $X_1$ is O, $Y_1$ is C=O, and $X_2$ is C=O, $Y_2$ is O.

15. The compound according to any one of items 1-12 or a salt (especially a pharmaceutically acceptable salt) or a stereoisomer thereof, wherein $X_1$ is C=O, $Y_1$ is O, and $X_2$ is O, $Y_2$ is C=O; or, $X_1$ and $X_2$ are both O, and $Y_1$ and $Y_2$ are both C=O.

16. The compound according to any one of the preceding items or a salt (especially a pharmaceutically acceptable salt), or a stereoisomer thereof, wherein $R_4$ is C10-C11 linear alkyl.

17. The compound according to any one of the preceding items or a salt (especially a pharmaceutically acceptable salt), or a stereoisomer thereof, wherein $R_5$ and $R_6$ are both C8 linear alkyl.

18. The compound according to any one of the preceding items or a salt (especially the pharmaceutically acceptable salt), or a stereoisomer thereof, wherein
o is 5, $R_4$ is C11 linear alkyl, p is 7, and $R_5$ and $R_6$ are both C8 linear alkyl, or
o is 6, $R_4$ is C10 linear alkyl, p is 7, and $R_5$ and $R_6$ are both C8 linear alkyl.

19. The compound according to item 1, or a salt (especially a pharmaceutically acceptable salt) or a stereoisomer thereof, wherein the compound is selected from:

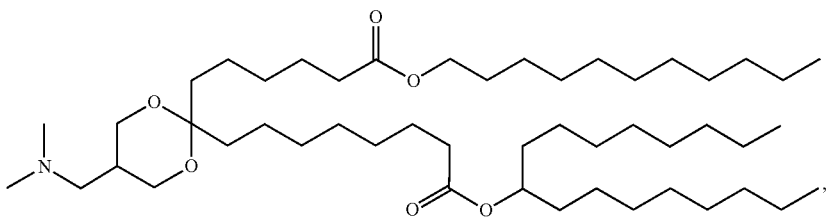

Compound 1

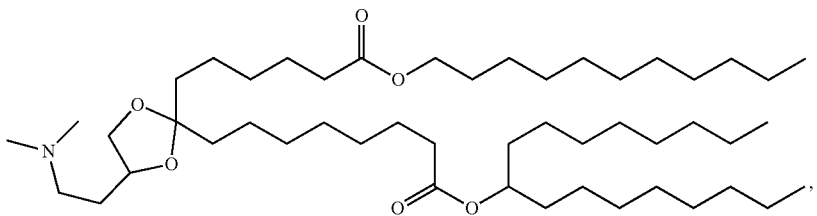

Compound 2

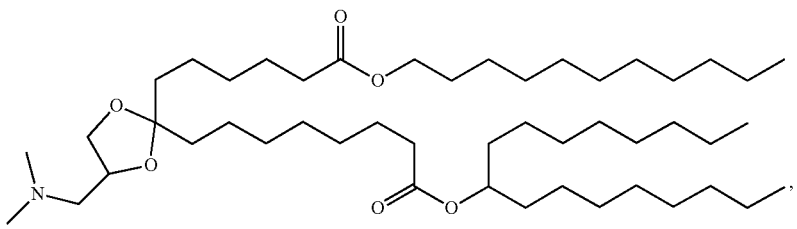

Compound 3

-continued
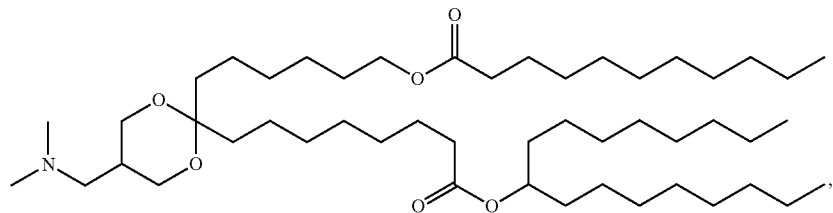
Compound 4
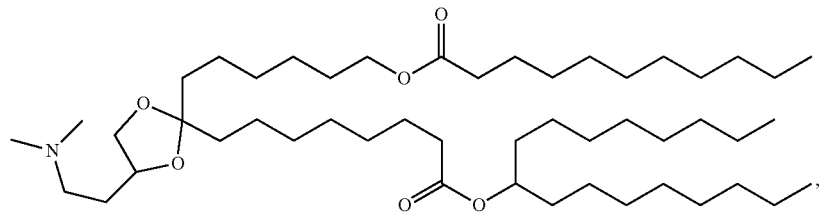
Compound 5
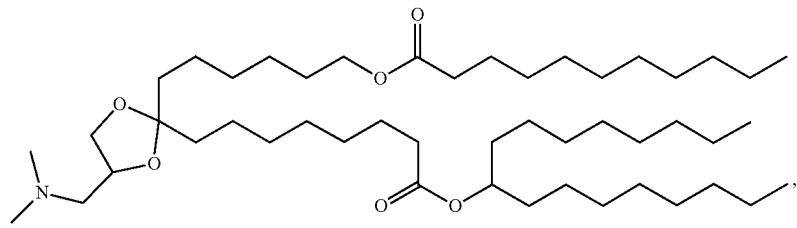
Compound 6
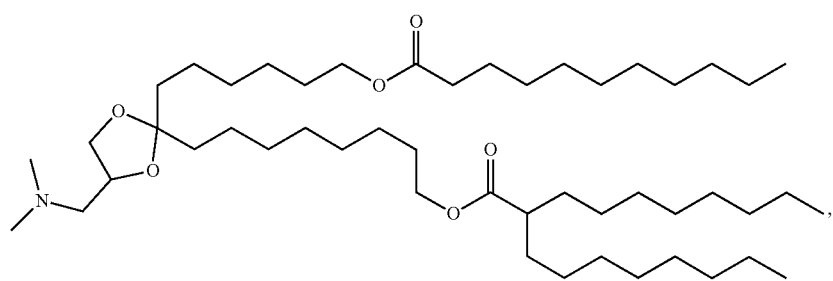
Compound 7
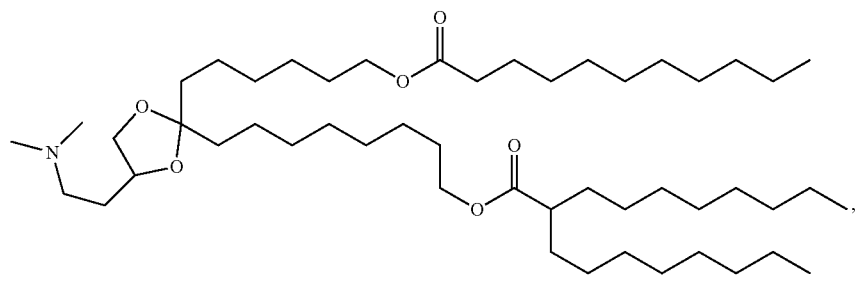
Compound 8
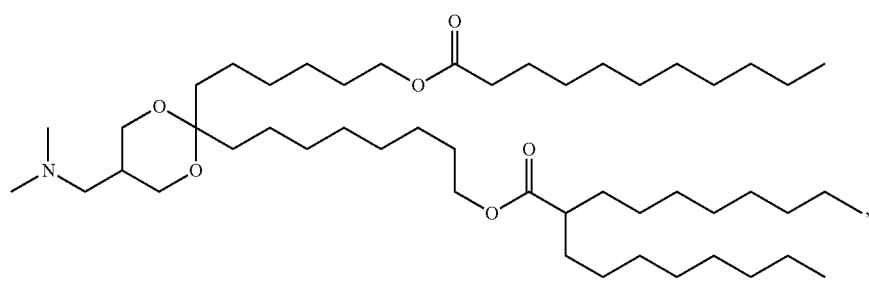
Compound 9

-continued
Compound 10
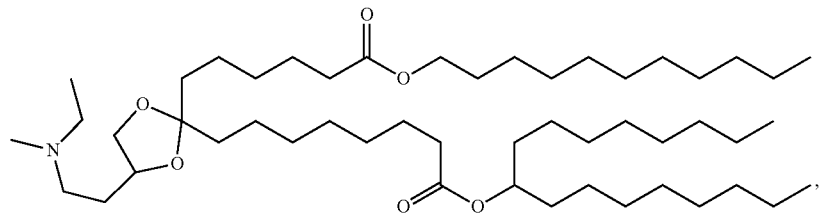
Compound 11
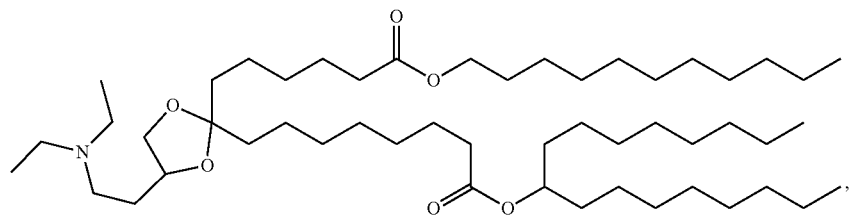
Compound 12
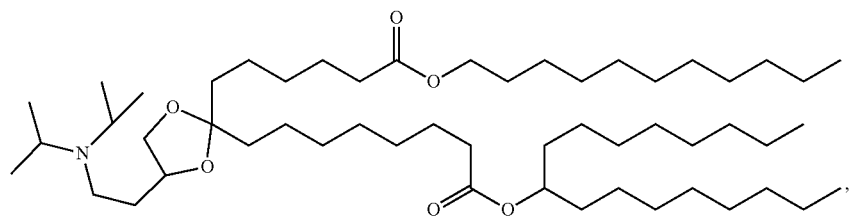
Compound 13
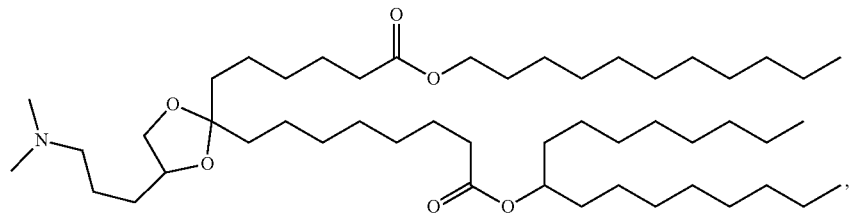
Compound 14
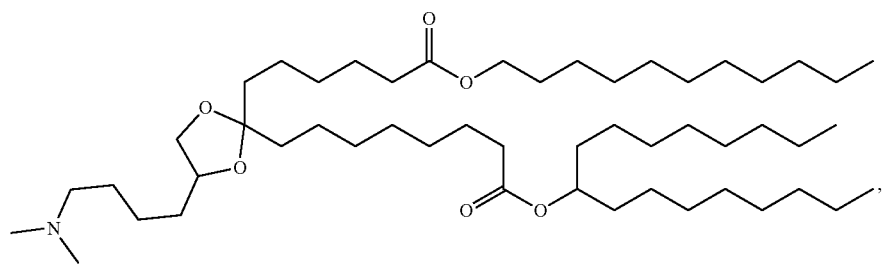
Compound 15
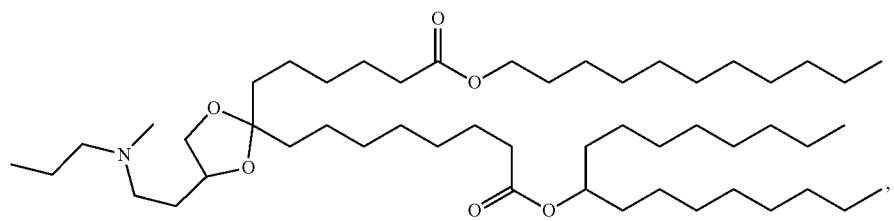
Compound 16
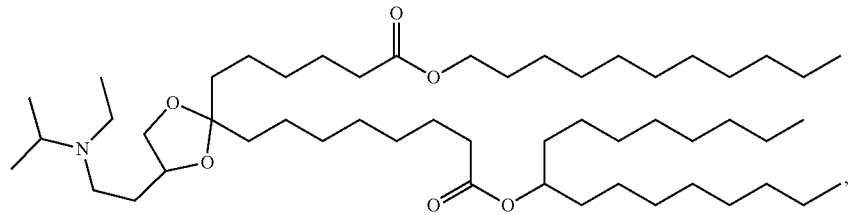

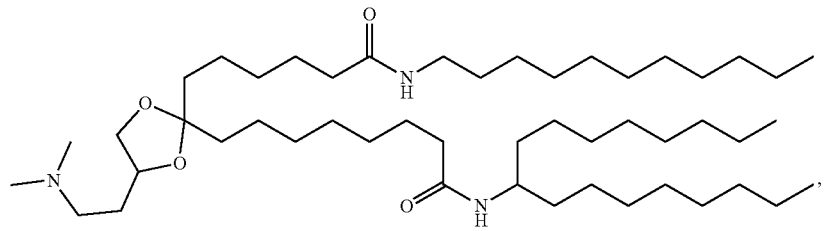
Compound 17
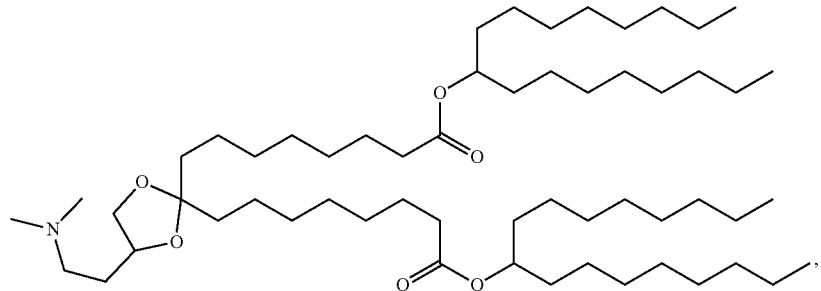
Compound 18
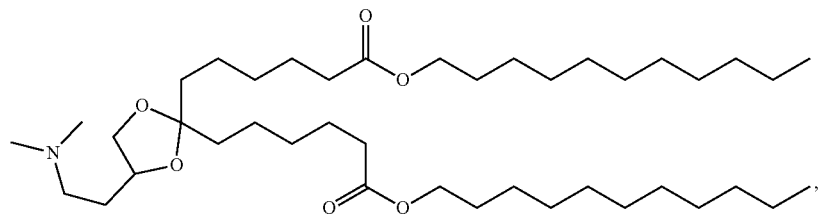
Compound 19
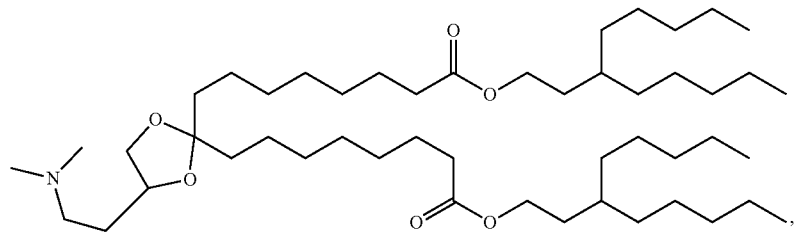
Compound 20
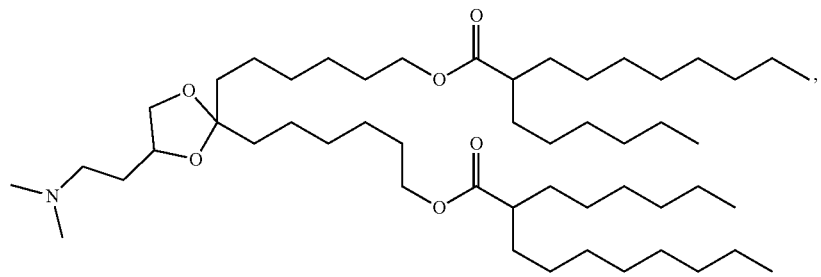
Compound 21
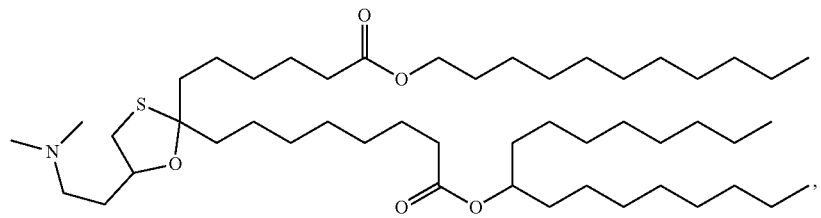
Compound 22

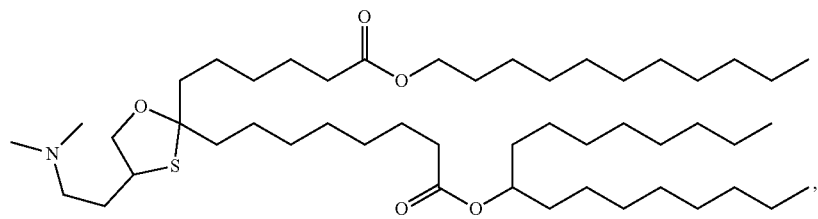
Compound 23
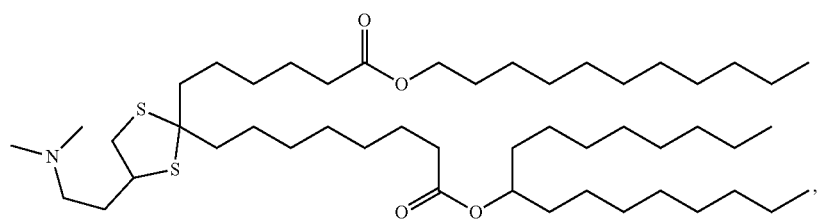
Compound 24
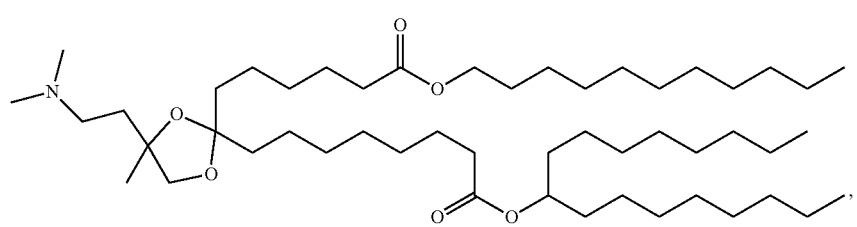
Compound 25
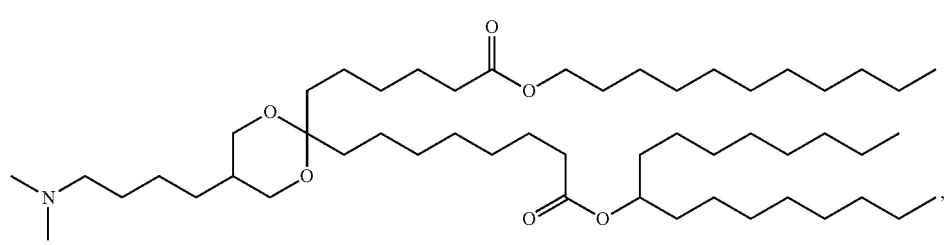
Compound 26
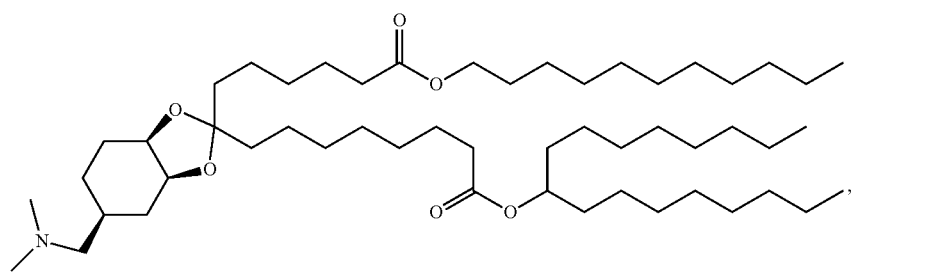
Compound 27
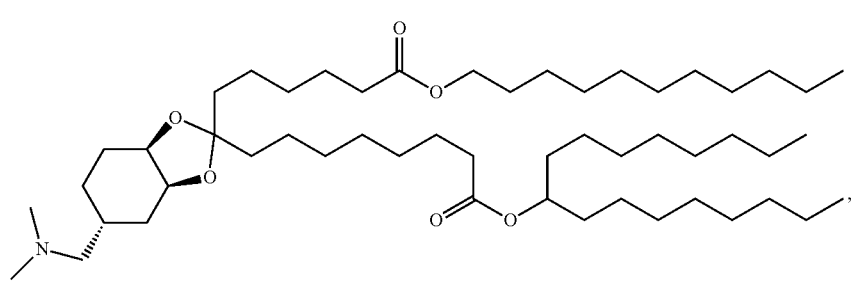
Compound 28

Compound 29
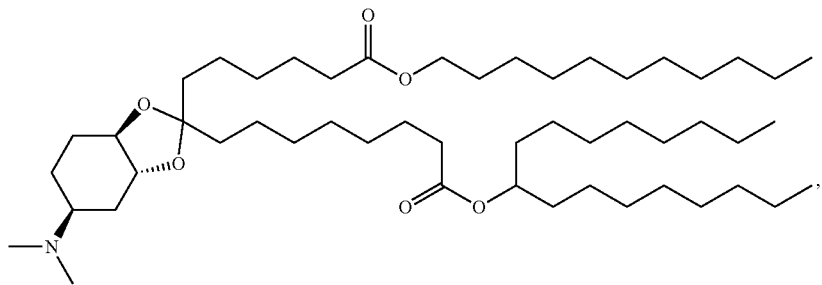
Compound 30
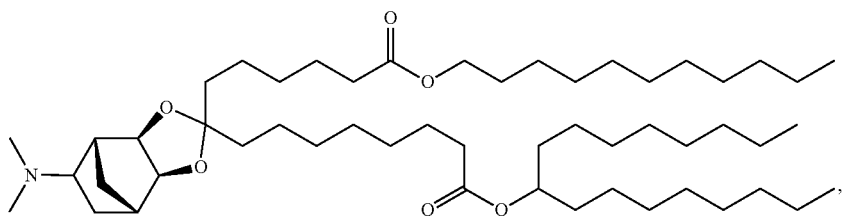
Compound 31
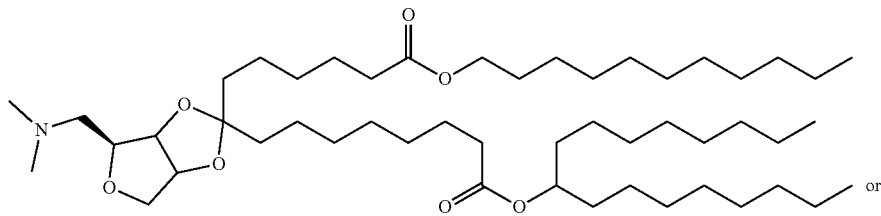
or
Compound 32
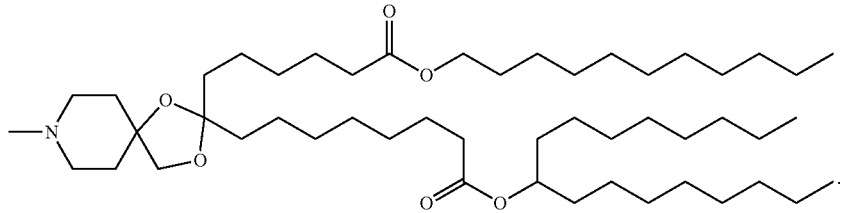
20. The compound according to item 1, or a salt (especially a pharmaceutically acceptable salt) or a stereoisomer thereof, wherein the compound is selected from:
Compound 2A
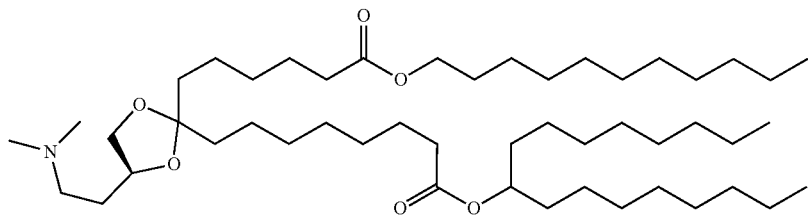
Compound 2B
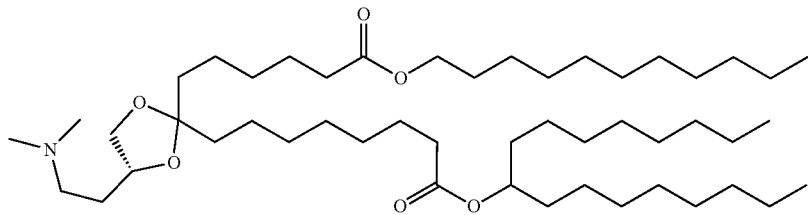

-continued
Compound 2C
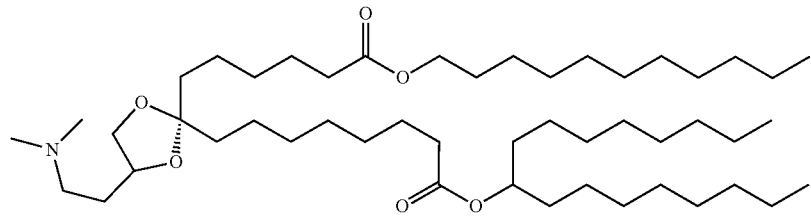
Compound 2D
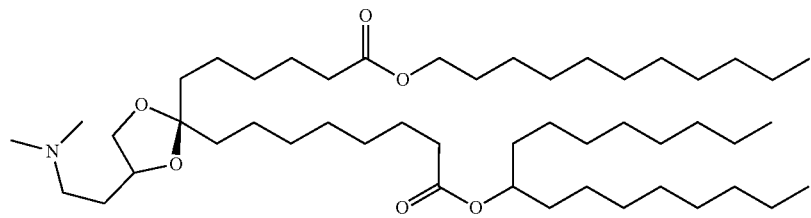
Compound 2E
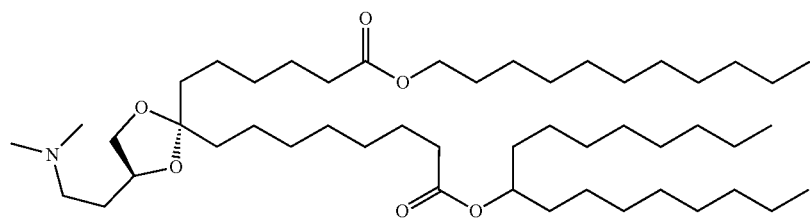
Compound 2F
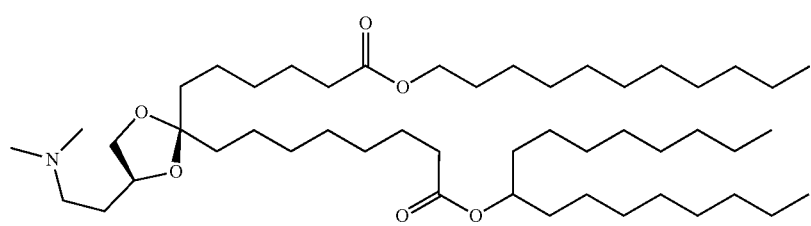
Compound 2G
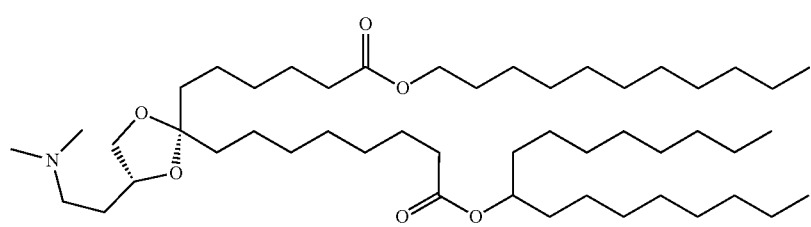
Compound 2H
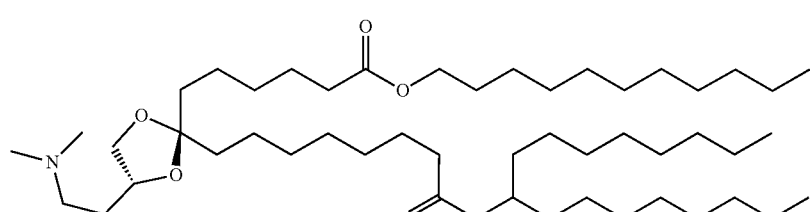
Compound 5A
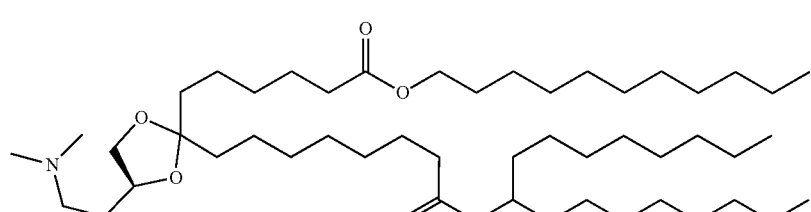

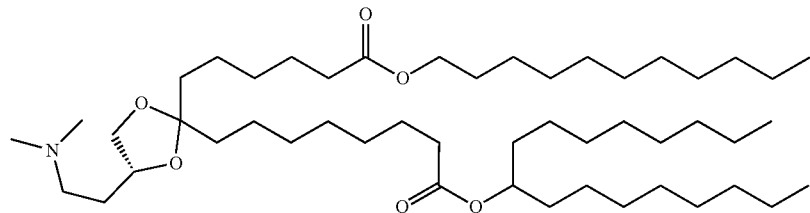
Compound 5B
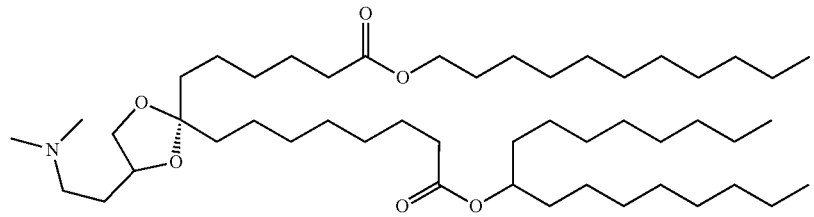
Compound 5C
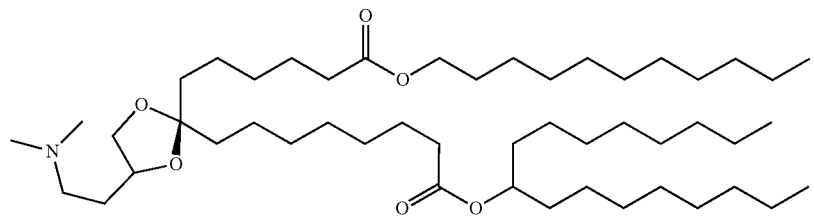
Compound 5D
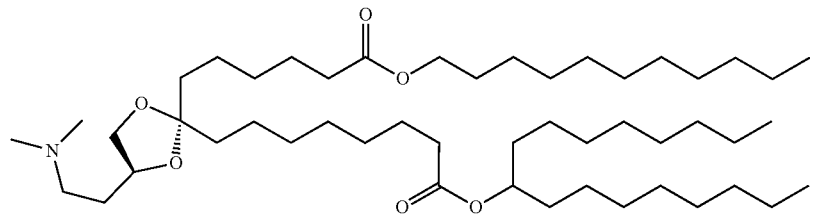
Compound 5E
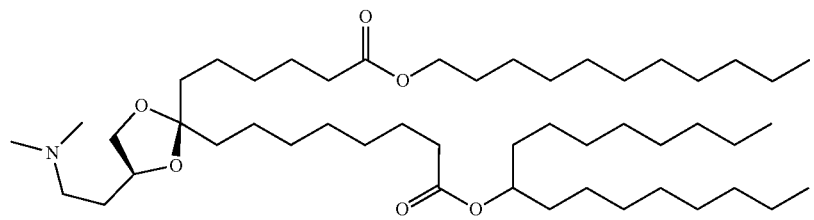
Compound 5F
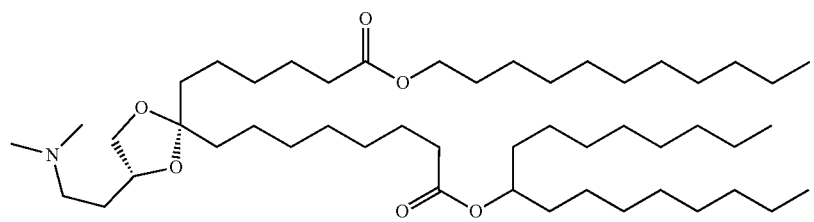
Compound 5G
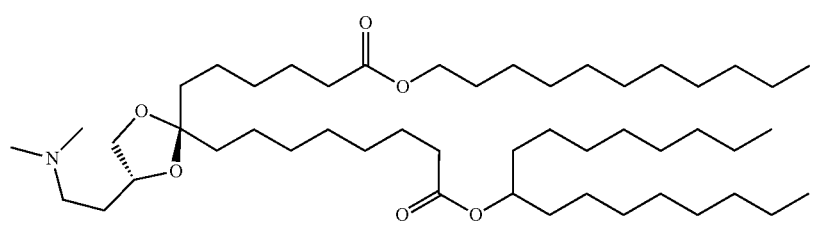
Compound 5H -continued
Compound 13A
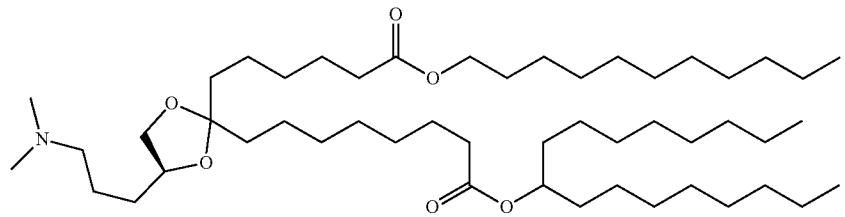
Compound 13B
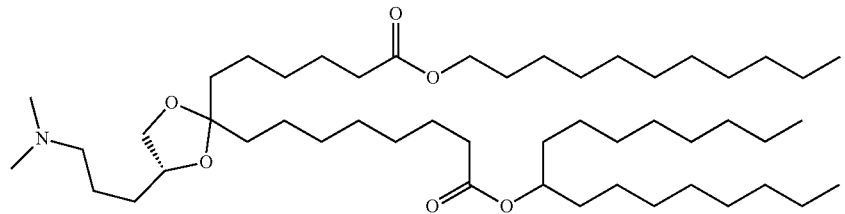
Compound 13C
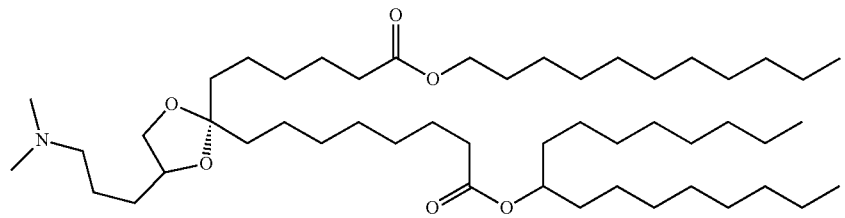
Compound 13D
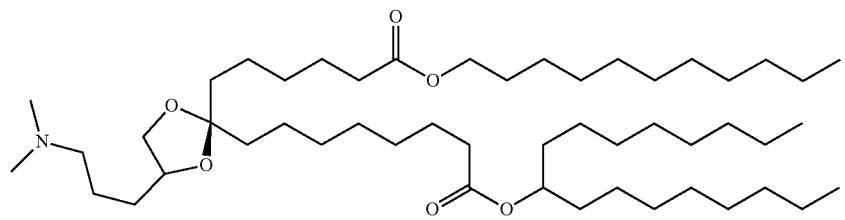
Compound 13E
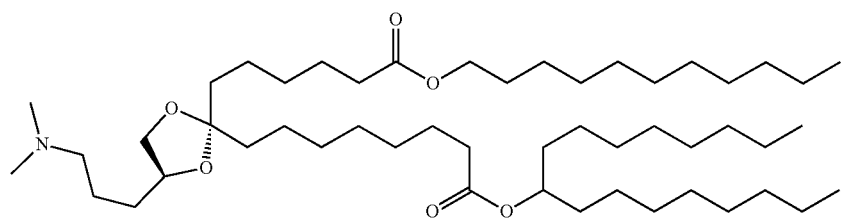
Compound 13F
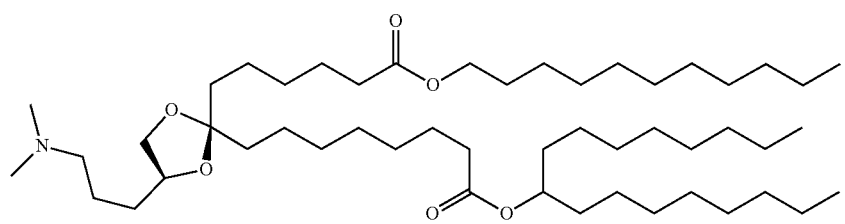
Compound 13G
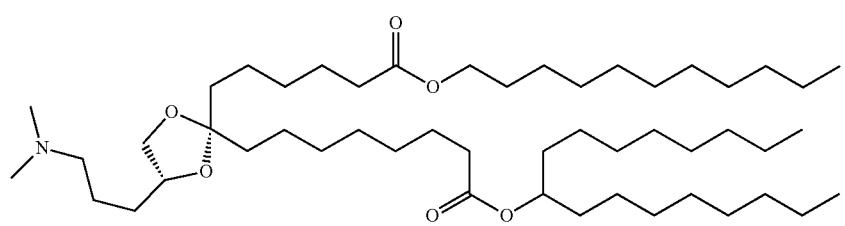

-continued
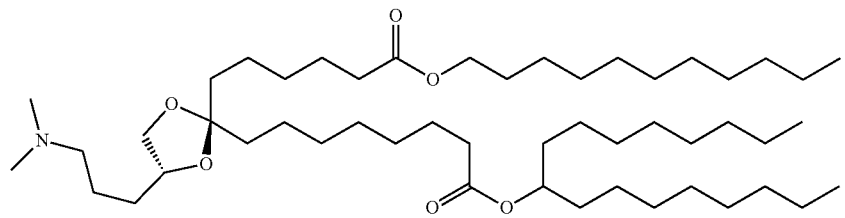
Compound 13H
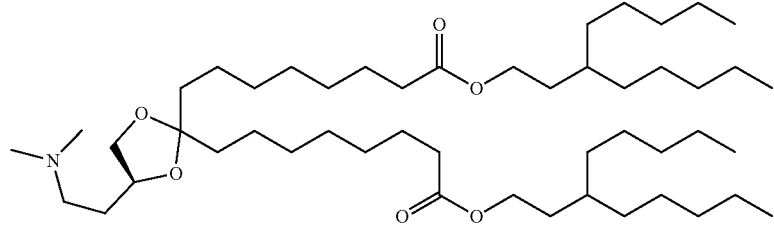
Compound 20A
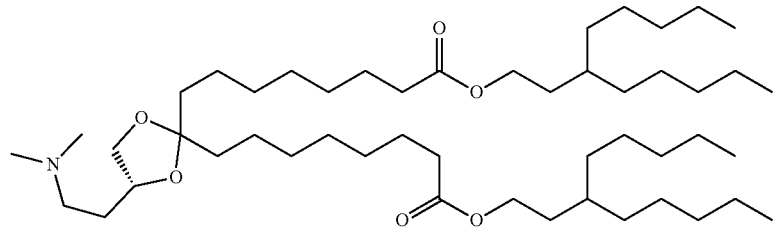
Compound 20B
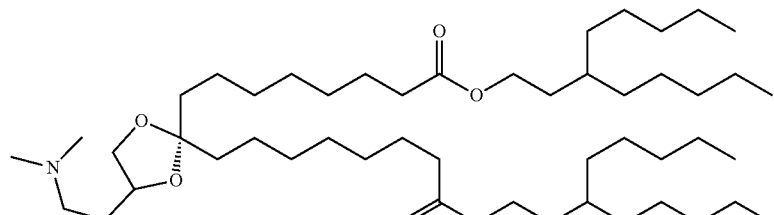
Compound 20C
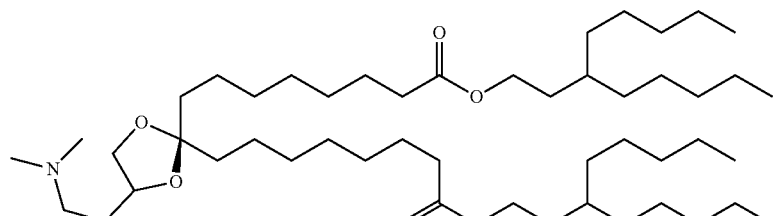
Compound 20D
Compound 20E
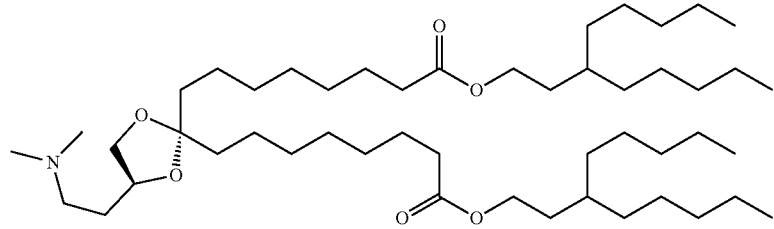

-continued

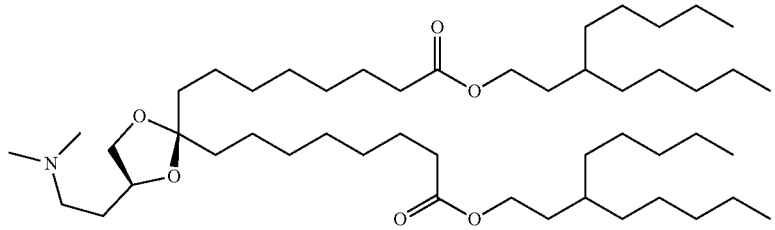
Compound 20F

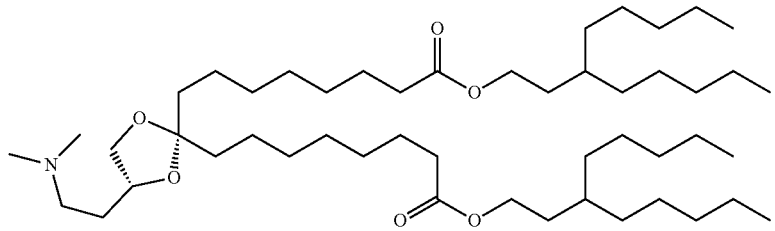
Compound 20G

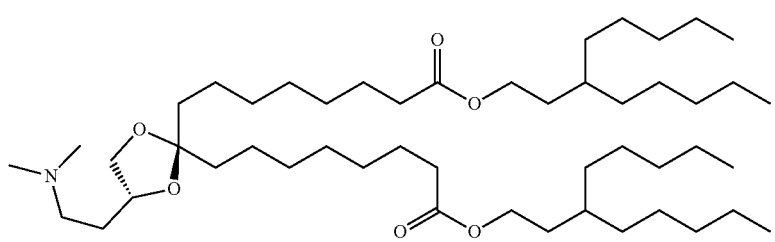
Compound 20H

21. A method for preparing a compound according to any one of items 1 to 20, wherein Compound (IA) is obtained from Compound J as a starting material,

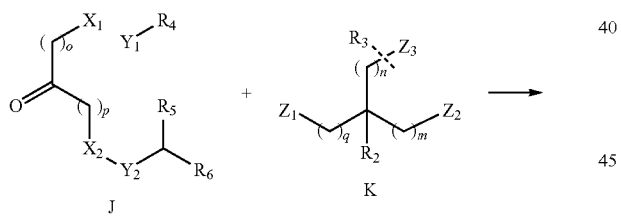

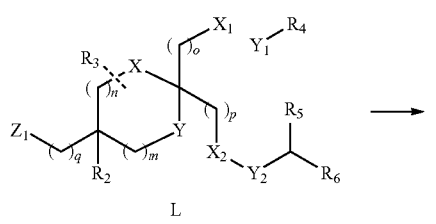

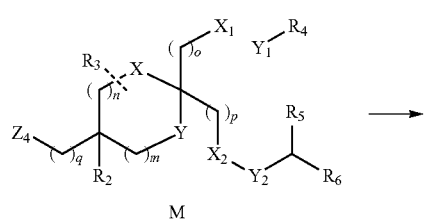

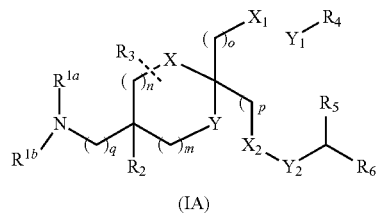

(IA)

wherein $Z_1$ is selected from OH, $Z_2$ and $Z_3$ are independently selected from OH or SH, respectively, and $Z_4$ is selected from OMs (Ms is methylsulfonyl); and X, Y, $X_1$, $X_2$, $Y_1$, $Y_2$, $R^{1a}$, $R^{1b}$, $R_2$, $R_3$, $R_4$, $R_5$, $R_6$, m, n, o, p and q are as defined in any one of items 1 to 20;

wherein compound J is reacted with compound K in a benzene-based solution of pyridinium 4-methylbenzenesulfonate to provide compound L, a benzene-based solvent used in said benzene solution is preferably toluene;

said compound L is reacted in a haloalkane solution of $(CH_3SO_2)_2O$ to provide a compound M, and said haloalkane is preferably DCM, dichloroethane or chloroform;

said compound M is reacted in a polar aprotic solvent to form a compound IA, and said polar aprotic solvent is preferably THF.

22. The preparation method according to item 21, wherein Compound J is obtained from Compound H and Compound C as starting materials,

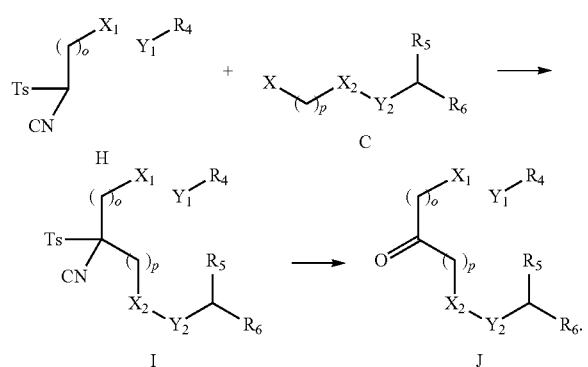

wherein X is selected from halogen; and $X_1$, $X_2$, $R_4$, $R_5$, $R_6$, o and p are as defined in any one of items 1 to 20;

wherein said compound H is reacted with Compound C in the presence of a carbonate salt, NBu$_4$I and a polar aprotic solvent to provide Compound I, said carbonate salt is preferably Cs$_2$CO$_3$ or K$_2$CO$_3$; said polar aprotic solvent is preferably DMF or DMA;

said Compound I is reacted at pH 1-5 to provide Compound J, preferably, said pH is adjusted by a hydrochloric acid solution, and said reaction is haloalkane, and preferably DCM, dichloroethane or chloroform.

23. The preparation method according to item 22, wherein Compound F is reacted with Compound G to provide Compound H,

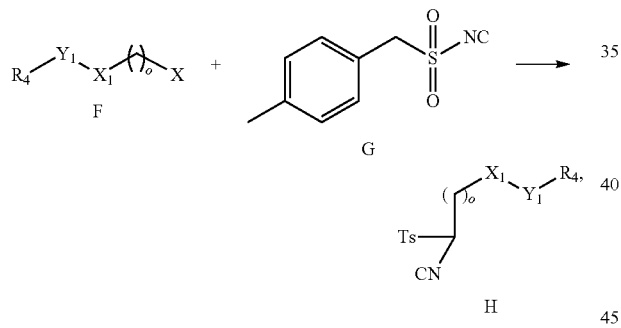

wherein X is selected from halogen;

$X_1$, $Y_1$, $R_4$ and o are as defined in any one of items 1 to 20;

wherein said Compound F is reacted with Compound G in the presence of a carbonate salt, NBu$_4$I and a polar aprotic solvent to provide Compound H, said carbonate salt is preferably Cs$_2$CO$_3$ or K$_2$CO$_3$; and said polar aprotic solvent is preferably DMF or DMA.

24. A nanoparticle composition comprising a lipid component which comprises a compound or a salt (especially a pharmaceutically acceptable salt) or a stereoisomer thereof according to in any one of items 1-20; preferably, said nanoparticle composition is lipid nanoparticle (LNP).

25. The nanoparticle composition according to item 24, wherein said lipid component further comprises a phospholipid, a structural lipid and/or a PEG lipid; wherein said phospholipid is preferably selected from one or more of the following compounds:

Dilauroyl lecithin (DLPC),
Dimyristoyl phosphatidylcholine (DMPC),
Dioleoyl lecithin (DOPC),
Dipalmitoyl phosphatidylcholine (DPPC),
Distearoyl phosphatidylcholine (DSPC),
Dioleoyl phosphatidylcholine (DUPC),
Palmitoyl oleoyl phosphatidylcholine (POPC),
1,2-Di-O-octadecyl-sn-glycero-3-phosphocholine (18:0 Diether PC),
1-Oleoyl-2-cholesteryldimethylsuccinoyl-sn-glycero-3-phosphocholine (OChemsPC),
1-Hexadecyl-sn-glycero-3-phosphocholine (C16 Lyso PC),
1,2-Divinyl-sn-glycero-3-phosphocholine,
1,2-Diarylacyl-sn-glycero-3-phosphocholine,
1,2-Dioleoyl-sn-glycero-3-phosphorylethanolamine (DOPE),
1,2-Di-phytanoyl-sn-glycero-3-phosphoethanolamine (ME 16.0 PE),
1,2-Distearoyl-sn-glycero-3-phosphoethanolamine,
1,2-Diethenol-sn-glycero-3-phosphoethanolamine,
1,2-Divinyl-sn-glycero-3-phosphoethanolamine,
1,2-Diaryl-sn-glycero-3-phosphoethanolamine,
1,2-Dithiohexaenoate-sn-glycero-3-phosphoethanolamine,
1,2-dioleoyl-sn-glycero-3-phosphate-(1-glycerol) sodium salt (DOPG) or sphingomyelin, for example, said phospholipid is DOPE or DSPC;

said structural lipid is preferably selected from one, two or more of cholesterol, coprosterol, sitosterol, ergosterol and stigmasterol; for example, said structural lipid is cholesterol; and/or said PEG lipid is preferably selected from one, two or more of PEG-modified phosphatidylethanolamine, PEG-modified phosphatidic acid, PEG-modified ceramide, PEG-modified dialkylamine, PEG-modified diacylglycerol or PEG-modified dialkylglycerol.

26. The nanoparticle composition according to any one of items 24-25, wherein said lipid component further comprises cationic and/or ionizable lipid.

27. The nanoparticle composition according to any one of items 24-26, further comprises a therapeutic agent and/or a prophylactic agent, said therapeutic and/or prophylactic agent is selected from vaccines, or compounds capable of eliciting an immune response, and/or nucleic acids, the nucleic acid is preferably RNA, and said RNA is selected from one, two or more of siRNA, aiRNA, miRNA, dsRNA, shRNA or mRNA, for example, said therapeutic and/or prophylactic agent is mRNA.

28. The nanoparticle composition according to any one of items 24-27, wherein the encapsulation efficiency of said therapeutic and/or prophylactic agent is ≥50%; or ≥80%; or ≥90%; and/or said nanoparticle composition has an average particle size of 50 nm-110 nm; and/or said nanoparticle composition have a polydispersity index of 0.04-0.20.

29. Use of the compound according to any one of items 1-20 or a salt thereof (especially a pharmaceutically acceptable salt) or stereoisomer thereof in the preparation of a lipid nanoparticle composition.

30. A pharmaceutical composition comprising the nanoparticle composition according to any one of items 24-28 as well as a pharmaceutically acceptable excipient.

31. A method of delivering a therapeutic and/or prophylactic agent to a mammalian cell, comprising administering the nanoparticle composition according to any one of items 24-28 or the pharmaceutical composition according to item 30 to a subject, said administration comprises contacting the cell with said nanoparticle composition or said pharmaceutical composition to deliver the therapeutic and/or prophylactic agent to the cell; e.g., the mammalian cell is in a mammal; for example said mammal is a human; e.g., said nanoparticle composition or pharmaceutical composition is administered intravenously, intramuscularly, intradermally, subcutaneously, intranasally, or by inhalation.

32. A method of producing the polypeptide of interest in a mammalian cell, comprising contacting the cell with the nanoparticle composition according to any one of claims 24-28 or the pharmaceutical composition according to item 30 to deliver a therapeutic and/or prophylactic agent to the cell, wherein said therapeutic and/or prophylactic agent is an mRNA encoding the polypeptide of interest, whereby the mRNA is capable of being translated in the cell to produce the polypeptide of interest; e.g., the mammalian cell is in a mammal; e.g., said mammal is a human; e.g., said nanoparticle composition or pharmaceutical composition is administered intravenously, intramuscularly, intradermally, subcutaneously, intranasally, or by inhalation.

33. A method of treating or preventing a disease or condition in a mammal, such as a human, comprising administering a therapeutically or prophylactically effective amount of a nanoparticle composition according to any one of items 24-28, or a pharmaceutical composition according to item 30 to the mammal; e.g., said disease or condition is characterized by a dysfunctional or abnormal protein or polypeptide activity; e.g., said disease or condition is selected from infectious diseases, cancer and proliferative diseases, genetic diseases, autoimmune diseases, diabetes, neurodegenerative diseases, cardiovascular diseases, renal vascular diseases or metabolic diseases; for example, said nanoparticle composition or pharmaceutical composition is administered intravenously, intramuscularly, intradermally, subcutaneously, intranasally, or by inhalation.

34. A method of specifically delivering a therapeutic and/or prophylactic agent to a mammalian organ, comprising administering to the mammal the nanoparticle composition according to any one of items 24-28 or the pharmaceutical composition according to item 30, said administration comprises contacting the mammalian organ with said nanoparticle composition or pharmaceutical composition, thereby delivering the therapeutic and/or prophylactic agent to the organ; e.g., said mammal is a human; e.g., said nanoparticle composition or pharmaceutical composition is administered intravenously, intramuscularly, intradermally, subcutaneously, intranasally, or by inhalation; e.g., said mammal is pretreated 24 hours prior to the contacting or administering step or less hours; e.g. about one hour prior to the contacting or administering step.

35. A method of delivering a therapeutic and/or prophylactic agent to a patient, comprising administering to a patient in need thereof the nanoparticle composition according to any one of items 24-28 or the pharmaceutical composition according to item 30.

36. A method of introducing a nucleic acid into a cell, comprising contacting said cell with a nanoparticle composition according to any one of items 24-28 or a pharmaceutical composition according to item 30.

37. The nanoparticle composition according to any one of items 24-28 or the pharmaceutical composition according to item 30, for use as a medicament.

38. The nanoparticle composition according to any one of items 24-28 or the pharmaceutical composition according to item 30 for use in delivering a therapeutic and/or prophylactic agent to a mammalian cell; e.g., the mammalian cell is in a mammal; e.g., said mammal is a human; e.g., said nanoparticle composition or pharmaceutical composition is administered intravenously, intramuscularly, intradermally, subcutaneously, intranasally, or by inhalation.

39. The nanoparticle composition of any one of items 24-28 or the pharmaceutical composition of item 30, which is used to produce a polypeptide of interest in a mammalian cell, wherein said composition comprises a therapeutic and/or prophylactic agent, which is an mRNA encoding the polypeptide of interest, whereby the mRNA is capable of being translated in the cell to produce the polypeptide of interest; e.g., the mammalian cell is in a mammal; e.g., said mammal is a human; e.g., said nanoparticle composition or pharmaceutical composition is administered intravenously, intramuscularly, intradermally, subcutaneously, intranasally, or by inhalation.

40. The nanoparticle composition according to any one of items 24-28 or the pharmaceutical composition according to item 30, for use in treating or preventing a disease or condition in a mammal, such as a human.

41. The nanoparticle composition of any one of items 24-28 or the pharmaceutical composition of item 30 for use in treating or preventing a disease or condition in a mammal, such as a human, said disease or condition is characterized by a dysfunctional or abnormal protein or polypeptide activity; e.g., said disease or condition is selected from infectious diseases, cancer and proliferative diseases, genetic diseases, autoimmune diseases, diabetes, neurodegenerative diseases, cardiovascular diseases, renal vascular diseases or metabolic diseases; for example, said nanoparticle composition or pharmaceutical composition is administered intravenously, intramuscularly, intradermally, subcutaneously, intranasally, or by inhalation.

42. The nanoparticle composition according to any one of items 24-28 or the pharmaceutical composition according to item 30, for use in the specific delivery of a therapeutic and/or prophylactic agent to a mammalian organ; e.g., said mammal is a human; e.g., said nanoparticle composition or pharmaceutical composition is administered intravenously, intramuscularly, intradermally, subcutaneously, intranasally, or by inhalation.

43. The nanoparticle composition according to any one of items 24-28 or the pharmaceutical composition according to item 30, for use in the specific delivery of a therapeutic and/or prophylactic agent to a mammalian organ; e.g., said mammal is a human; e.g., said nanoparticle composition or pharmaceutical composition is administered intravenously, intramuscularly, intradermally, subcutaneously, intranasally, or by inhalation, wherein said mammal is pretreated 24 hours prior to the contacting or administering step or less hours; e.g. about one hour prior to the contacting or administering step.

44. The nanoparticle composition according to any one of items 24-28 or the pharmaceutical composition according to item 30 for delivering a therapeutic and/or prophylactic agent to a patient.

45. The nanoparticle composition according to any one of items 24-28 or the pharmaceutical composition according to item 30 for introducing a nucleic acid into a cell.
46. Use of the nanoparticle composition according to any one of items 24-28 or the pharmaceutical composition according to item 30 in the manufacture of a medicament for delivering a therapeutic and/or prophylactic agent to a mammalian cell; e.g., the mammalian cell is in a mammal; e.g., said mammal is a human; e.g., said nanoparticle composition or pharmaceutical composition is administered intravenously, intramuscularly, intradermally, subcutaneously, intranasally, or by inhalation.
47. Use of the nanoparticle composition according to any one of items 24-28 or the pharmaceutical composition according to item 30 in the manufacture of a medicament for producing a polypeptide of interest in a mammalian cell, wherein said medicament comprises a therapeutic and/or prophylactic agent, which is mRNA coding the polypeptide of interest, whereby the mRNA is capable of being translated in the cell to produce the polypeptide of interest; e.g., the mammalian cell is in a mammal; e.g., said mammal is a human; e.g., said nanoparticle composition or pharmaceutical composition is administered intravenously, intramuscularly, intradermally, subcutaneously, intranasally, or by inhalation.
48. Use of the nanoparticle composition according to any one of items 24-28 or the pharmaceutical composition according to item 30 in the manufacture of a medicament for the treatment or prevention of a disease or condition in a mammal, e.g., a human.
49. Use of the nanoparticle composition according to any one of items 24-28 or the pharmaceutical composition according to item 30 in the manufacture of a medicament for the treatment or prevention of a disease or condition in a mammal, e.g., a human, and said disease or condition is characterized by a dysfunctional or abnormal protein or polypeptide activity; e.g., said disease or condition is selected from infectious diseases, cancer and proliferative diseases, genetic diseases, autoimmune diseases, diabetes, neurodegenerative diseases, cardiovascular diseases, renal vascular diseases or metabolic diseases; for example, said nanoparticle composition or pharmaceutical composition is administered intravenously, intramuscularly, intradermally, subcutaneously, intranasally, or by inhalation.
50. Use of the nanoparticle composition according to any one of items 24-28 or the pharmaceutical composition according to item 30 in the manufacture of a medicament for the specific delivery of a therapeutic and/or prophylactic agent to a mammalian organ; e.g., said mammal is a human; e.g., said nanoparticle composition or pharmaceutical composition is administered intravenously, intramuscularly, intradermally, subcutaneously, intranasally, or by inhalation.
51. Use of the nanoparticle composition according to any one of items 24-28 or the pharmaceutical composition according to item 30 in the manufacture of a medicament for the specific delivery of a therapeutic and/or prophylactic agent to a mammalian organ; e.g., said mammal is a human; e.g., said nanoparticle composition or pharmaceutical composition is administered intravenously, intramuscularly, intradermally, subcutaneously, intranasally, or by inhalation, wherein said mammal is pretreated 24 hours prior to the contacting or administering step or less hours; e.g. about one hour prior to the contacting or administering step.
52. Use of the nanoparticle composition according to any one of items 24-28 or the pharmaceutical composition according to item 30 in the manufacture of a medicament for delivering a therapeutic and/or prophylactic agent to a patient.
53. Use of the nanoparticle composition according to any one of items 24-28 or the pharmaceutical composition according to item 30 in the preparation of a product for introducing nucleic acids into a cell.
54. Use of the nanoparticle composition according to any one of items 24-28 or the pharmaceutical composition according to item 30 for use in the treatment or prevention a disease or condition in a mammal, such as a human; e.g., said disease or condition is characterized by a dysfunctional or abnormal protein or polypeptide activity; e.g., said disease or condition is selected from infectious diseases, cancer and proliferative diseases, genetic diseases, autoimmune diseases, diabetes, neurodegenerative diseases, cardiovascular diseases, renal vascular diseases or metabolic diseases; for example, said nanoparticle composition or pharmaceutical composition is administered intravenously, intramuscularly, intradermally, subcutaneously, intranasally, or by inhalation.

The present application further includes the following embodiments (Part II):

1. A compound of formula (I), or a salt or an isomer thereof, (I)

wherein, $R_1$ is wherein $R^{1a}$, $R^{1b}$ are independently selected from H, C1-C6alkyl, $R_2$, $R_3$ are independently selected from H or C1-C6alkyl, or $R_1$ and $R_2$, together with the carbon atom to which they are attached, form a substituted or unsubstituted 5-7 membered nitrogen-containing heterocyclic ring, and $R_3$ is selected from H or C1-C6alkyl, or $R_1$ and $R_3$, together with the carbon atoms to which they are attached, form ring A, which is a substituted or unsubstituted 5-7 membered carbocyclic or heterocyclic ring, and $R_2$ is selected from H or C1-C6alkyl;

$R_4$, $R_5$ and $R_6$ are independently selected from C1-C14alkyl;

X and Y are independently selected from O or S;

$X_1$ and $X_2$ are independently selected from C=O or O, and $Y_1$ and $Y_2$ are independently selected from C=O or O, with the proviso that $X_1$ and $Y_1$ are not both C=O or O, and $X_2$ and $Y_2$ are not both C=O or O;

m and n are independently selected from 0, 1 or 2, with the proviso that m and n are not both 0;

o and p are independently selected from 1, 2, 3, 4, 5, 6, 7, 8, 9 or 10;

q is selected from 0, 1, 2, 3, 4, 5 or 6.

2. The compound according to item 1, wherein the compound of formula (I) is of formula (IA),

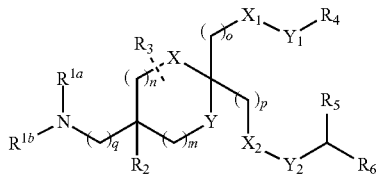
(IA)

wherein q is selected from 0, 1, 2, 3 or 4.

3. The compound according to item 1, wherein the compound of formula (I) is of formula (IB),

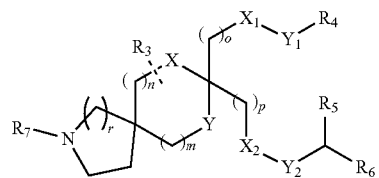
(IB)

wherein $R_7$ is selected from H or C1-C6alkyl;
r is selected from 0, 1, 2 or 3.

4. The compound according to item 1, wherein the compound of formula (I) is of formula (IC) or (ID),

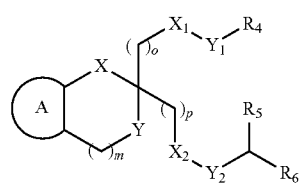
(IC)

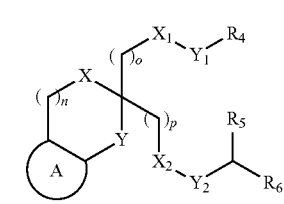
(ID)

wherein, ring A is substituted by one or more $R_8$, said $R_8$ being

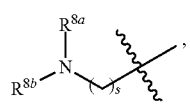

wherein $R^{8a}$ and $R^{8b}$ are independently selected from H or C1-C6alkyl, and s is selected from 0, 1, 2, 3, 4, 5 or 6.

5. The compound according to item 4, said ring A is selected from

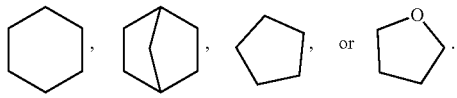

6. The compound according to any one of items 1-5, wherein $R_4$ is C10-C11alkyl.

7. The compound according to item 6, wherein $R_4$ is C10-C11 linear alkyl.

8. The compound according to any one of items 1-7, wherein $R_5$ and $R_6$ are C8alkyl.

9. The compound according to item 8, wherein $R_5$ and $R_6$ are C8 linear alkyl.

10. The compound according to any one of items 1-9, wherein said o is 5 or 6.

11. The compound according to any one of items 1-10, wherein said p is 7 or 8.

12. The compound according to any one of items 1-11, wherein o is 5, $R_4$ is C11 linear alkyl, p is 7, and, $R_5$ and $R_6$ are C8 linear alkyl, or o is 6, $R_4$ is C10 linear alkyl, p is 7, and, $R_5$ and $R_6$ are C8 linear alkyl.

13. The compound according to any one of items 1-12, wherein said $X_1$, $X_2$ are C=O, and said $Y_1$ and $Y_2$ are O.

14. The compound according to any one of items 1-12, wherein said $X_1$ is O, $Y_1$ is C=O, and said $X_2$ is C=O, $Y_2$ is O.

15. The compound according to any one of items 1-12, wherein said $X_1$ is C=O, $Y_1$ is O, and said $X_2$ is O, $Y_2$ is C=O.

16. The compound according to any one of items 1-12, wherein said $X_1$ and $X_2$ are O, and said $Y_1$ and $Y_2$ are C=O.

17. The compound according to any one of items 1-16, wherein said X and Y are both O.

18. The compound according to any one of items 1-16, wherein said n is 0, m is 1, or n is 1, m is 0, or n is 1, m is 1.

19. The compound according to any one of items 1-18, wherein said C1-C6alkyl is selected from —$CH_3$, —$CH_2CH_3$ or —$CH(CH_3)_2$.

20. The compound according to item 1, wherein the compound of formula (I) is selected from:
Compound 1
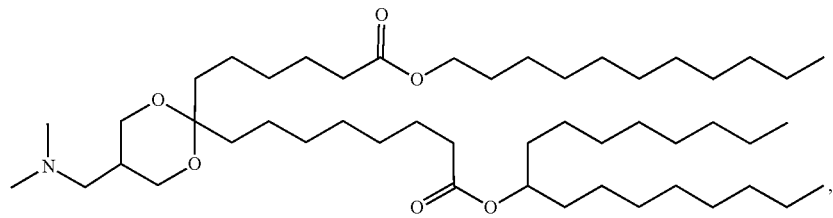
Compound 2
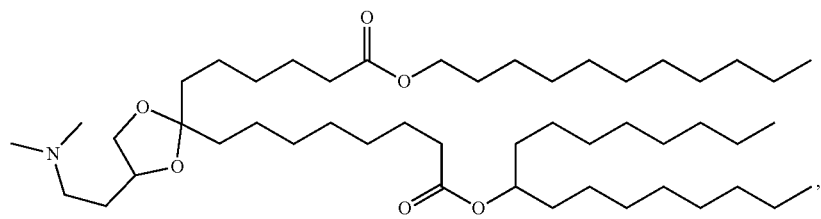
Compound 3
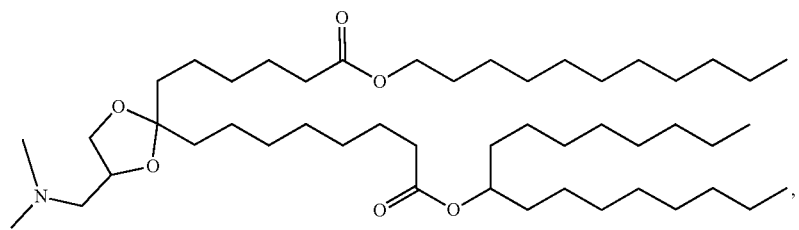
Compound 4
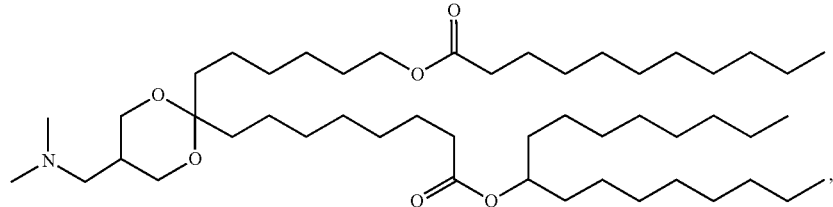
Compound 5
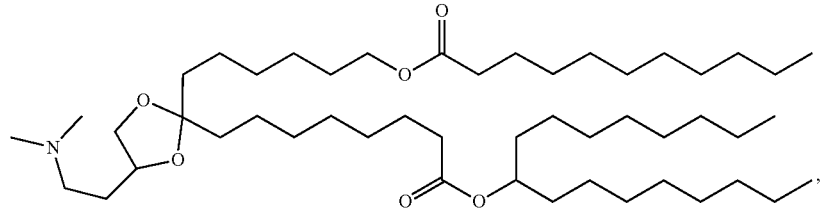
Compound 6
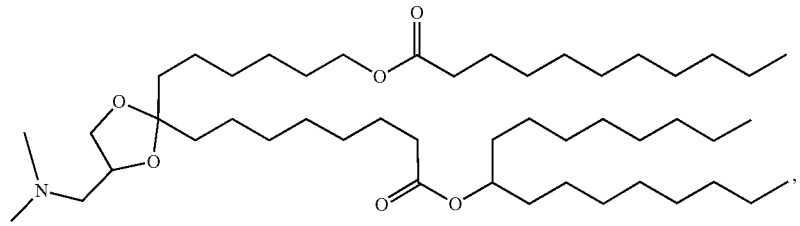

-continued
Compound 7
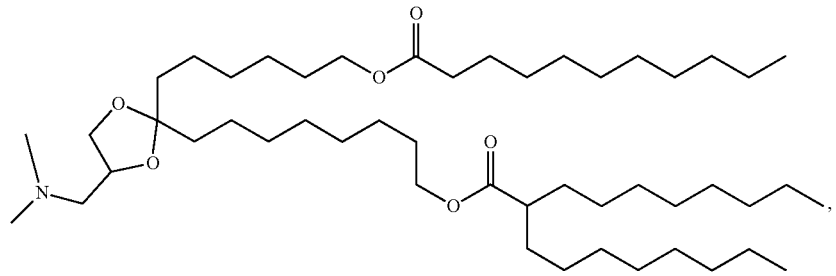
Compound 8
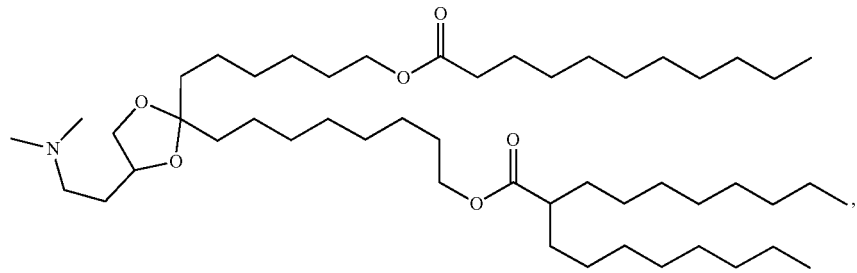
Compound 9
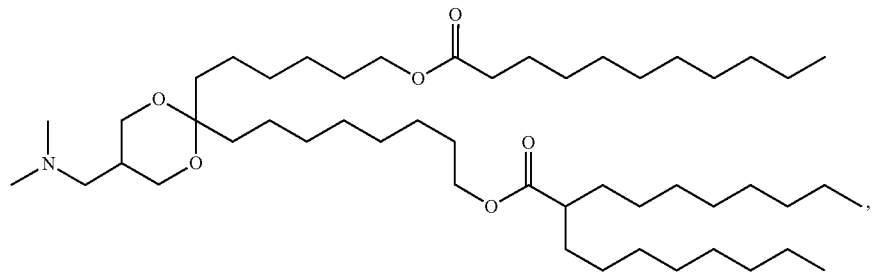
Compound 10
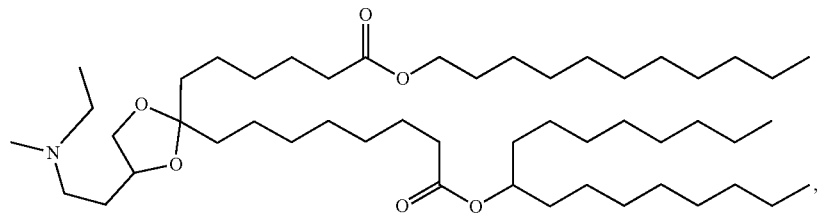
Compound 11
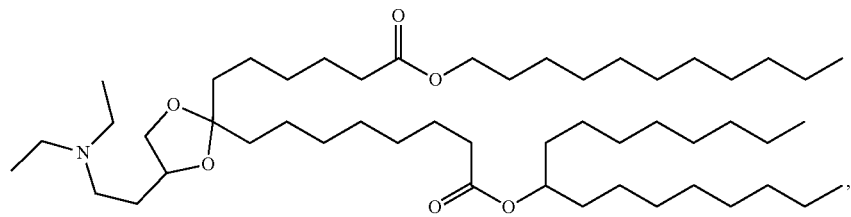
Compound 12
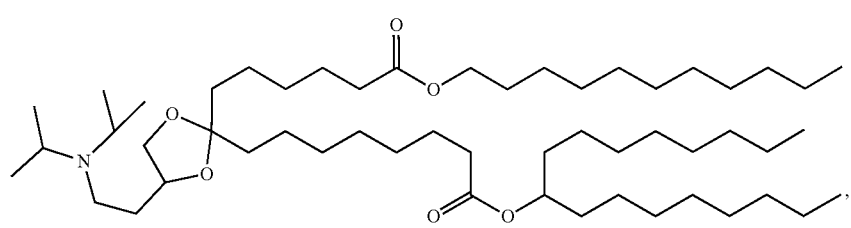

-continued
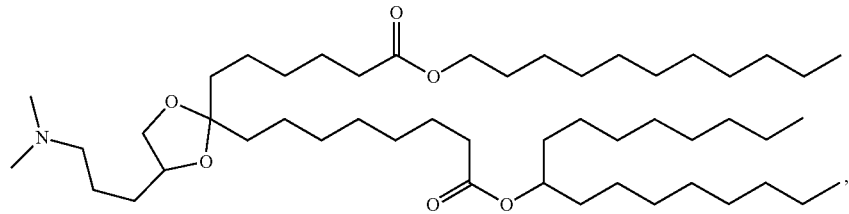
Compound 13
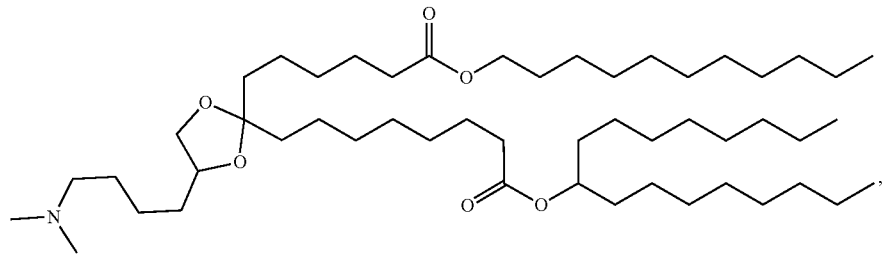
Compound 14
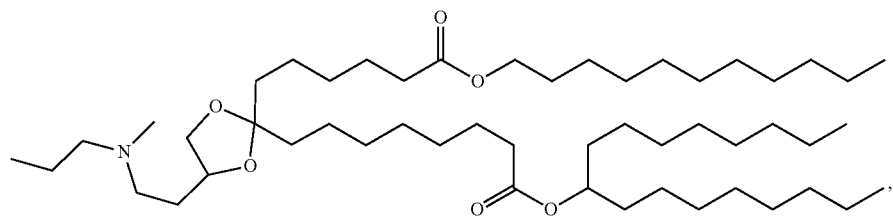
Compound 15
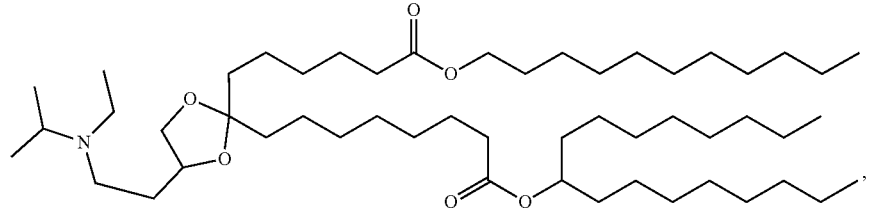
Compound 16
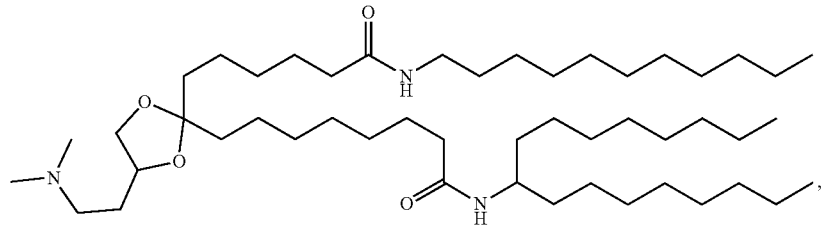
Compound 17
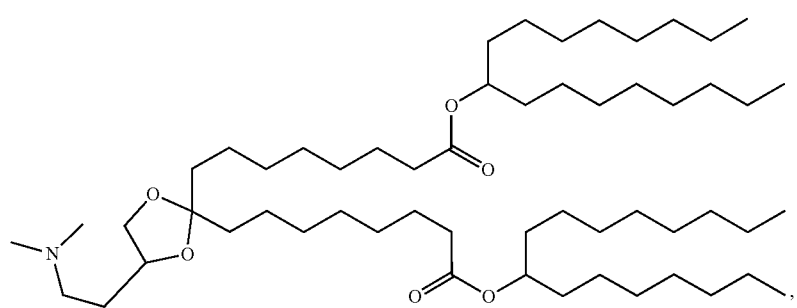
Compound 18

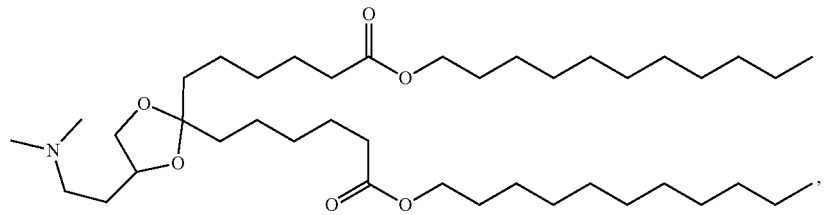
Compound 19
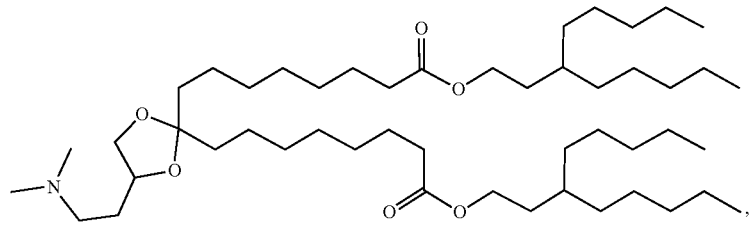
Compound 20
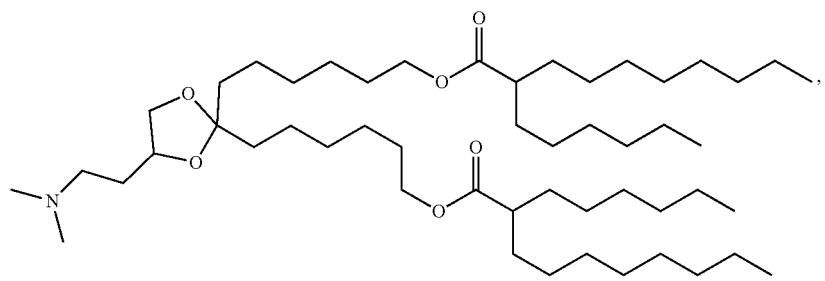
Compound 21
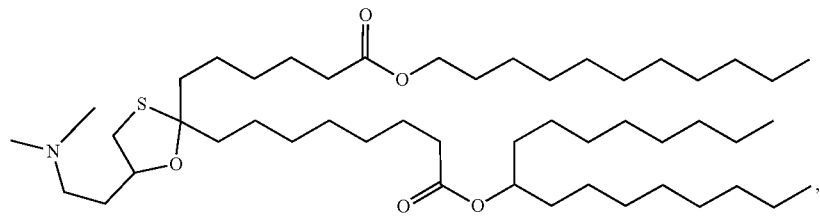
Compound 22
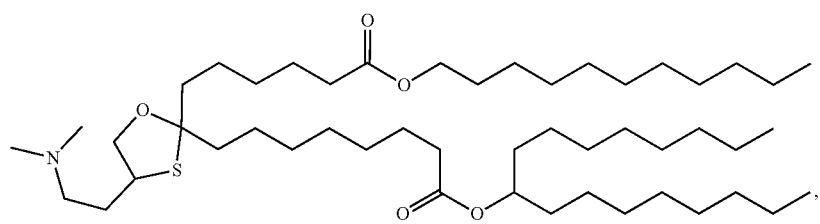
Compound 23
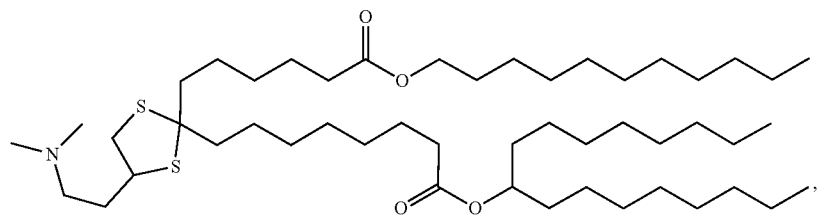
Compound 24

Compound 25
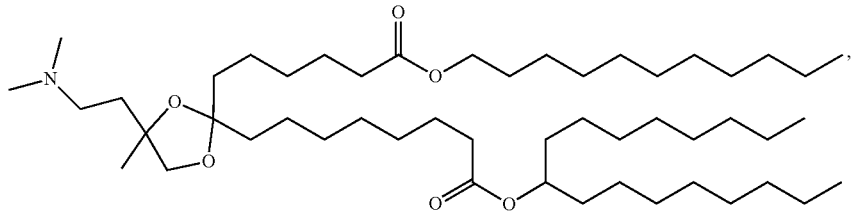
Compound 26
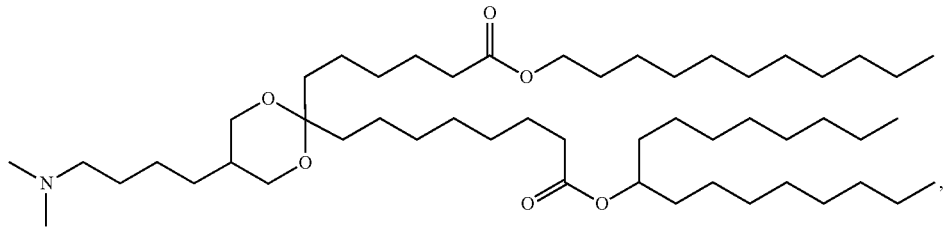
Compound 27
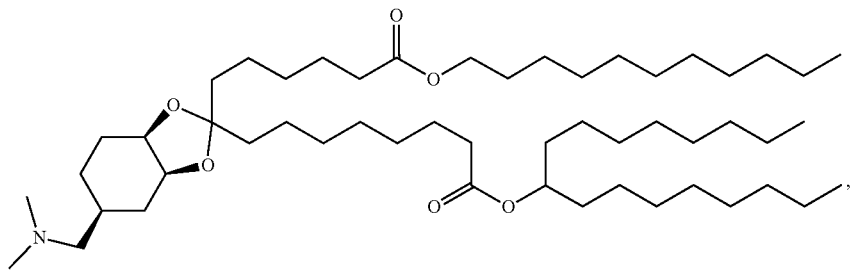
Compound 28
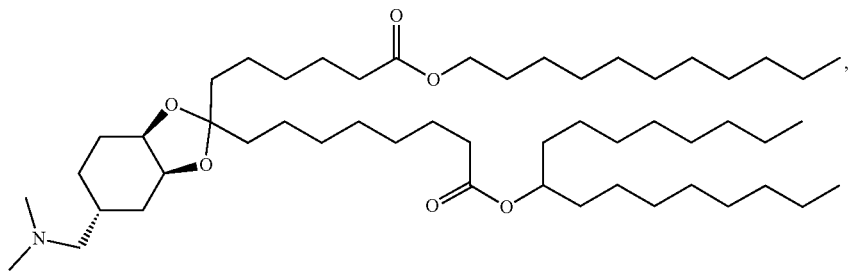
Compound 29
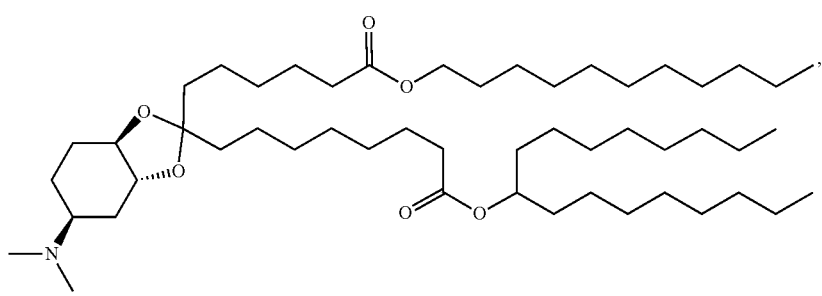
Compound 30
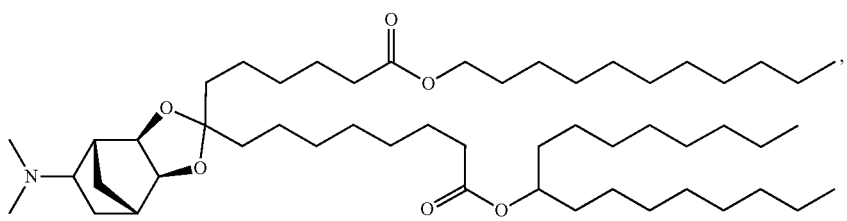

-continued

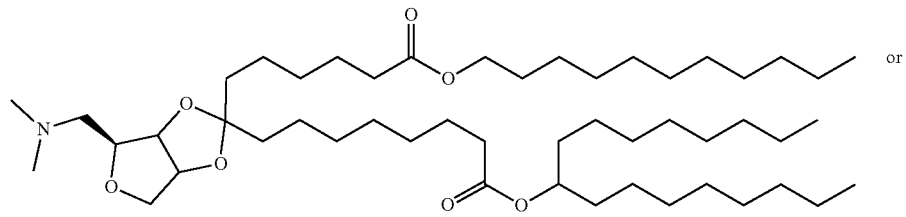

Compound 31 or

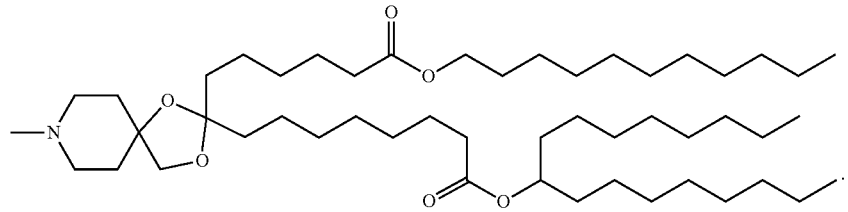

Compound 32

21. A method of preparing the compound according to any one of items 1-20, wherein Compound (IA) is obtained from Compound J as a starting material,

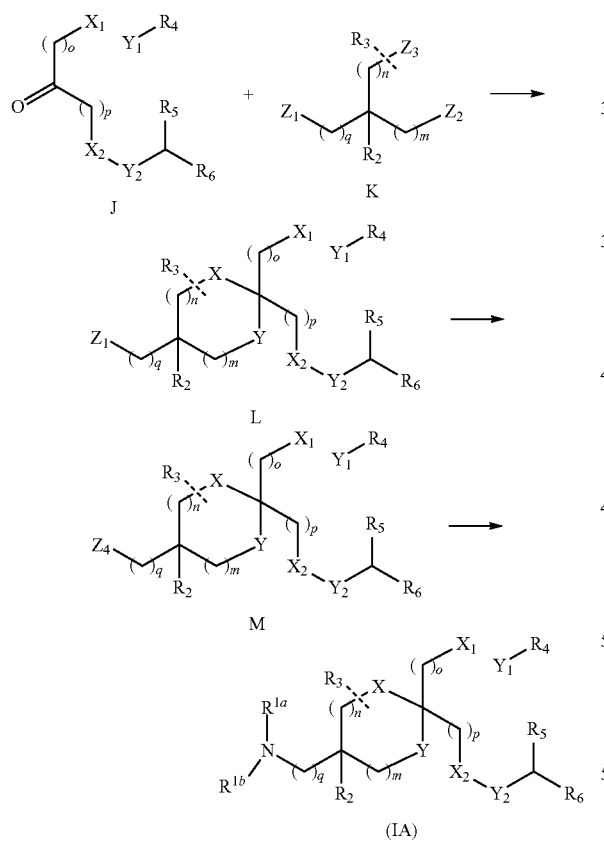

wherein $Z_1$ is selected from OH, $Z_2$ and $Z_3$ are independently selected from OH or SH, respectively, and $Z_4$ is selected from OMs;
X and Y are independently selected from O or S;
$X_1$ and $X_2$ are independently selected from C=O or O, $Y_1$ and $Y_2$ are independently selected from C=O or O, with the proviso that $X_1$ and $Y_1$ are not both C=O or O, and $X_2$ and $Y_2$ are not both C=O or O;
$R^{1a}$ and $R^{1b}$ are independently selected from H or C1-C6alkyl;
$R_2$ and $R_3$ are independently selected from H or C1-C6alkyl;
$R_4$, $R_5$ and $R_6$ are independently selected from C1-C14alkyl;
m and n are independently selected from 0, 1, 2, with the proviso that m and n are not both 0;
o and p are independently selected from 1, 2, 3, 4, 5, 6, 7, 8, 9 or 10;
q is selected from 0, 1, 2, 3, 4, 5 or 6;
wherein said Compound J is reacted with Compound K in a benzene-based solution of Tso-Py to provide Compound L, the benzene-based solvent used is preferably toluene;
said Compound L is reacted in the solution of $(CH_3SO_2)_2O$ in haloalkane to provide Compound M, and said haloalkane is preferably DCM, dichloroethane or chloroform;
said Compound M is reacted in a polar aprotic solvent to produce Compound IA, said polar aprotic solvent is preferably THF.
22. The preparation method according to item 21, wherein Compound J is obtained from Compound H and Compound C as starting materials,

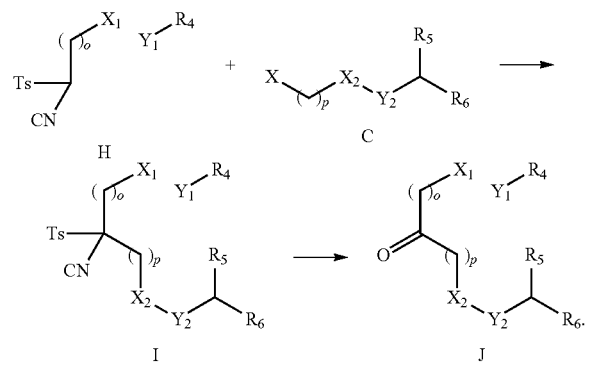

wherein $X_1$ and $X_2$ are independently selected from C=O or O, $Y_1$ and $Y_2$ are independently selected from C=O or O, with the proviso that $X_1$ and $Y_1$ are not both C=O or O, and $X_2$ and $Y_2$ are not both C=O or O;

X is selected from halogen;

$R_4$, $R_5$ and $R_6$ are independently selected from C1-C14alkyl;

o and p are independently selected from 1, 2, 3, 4, 5, 6, 7, 8, 9 or 10;

wherein said Compound H is reacted with Compound C in the presence of a carbonate salt, $NBu_4I$ and a polar aprotic solvent to provide Compound I, said carbonate salt is preferably $Cs_2CO_3$ and $K_2CO_3$; and said polar aprotic solvent is preferably DMF or DMA;

said Compound I is reacted at pH 1-5 to provide Compound J, preferably, said pH is adjusted by a hydrochloric acid solution, and said reaction solvent is haloalkane, and preferably DCM, dichloroethane or chloroform.

23. The preparation method according to item 22, wherein Compound F is reacted with Compound G with to provide Compound H,

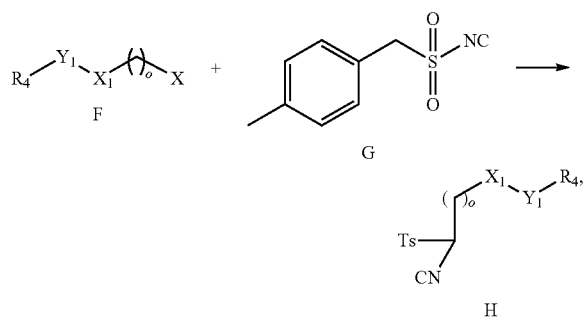

wherein $X_1$ and $Y_1$ are independently selected from C=O or O;

X is selected from halogen; $R_4$ is selected from C1-C14alkyl;

o is selected from 1, 2, 3, 4, 5, 6, 7, 8, 9, 10;

wherein said Compound F is reacted with Compound G in the presence of a carbonate salt, $NBu_4I$ and a polar aprotic solvent to provide Compound H, said carbonate salt is preferably $Cs_2CO_3$, $K_2CO_3$; and said polar aprotic solvent is preferably DMF or DMA.

24. A nanoparticle composition comprising a lipid component which comprises a compound according to any one of items 1-20.

25. The nanoparticle composition according to item 24, wherein said lipid component further comprises a phospholipid.

26. The nanoparticle composition according to item 25, wherein said phospholipid is selected from one, two or more of the following compounds:

Dilauroyl lecithin (DLPC),
Dimyristoyl phosphatidylcholine (DMPC),
Dioleoyl lecithin (DOPC),
Dipalmitoyl phosphatidylcholine (DPPC),
Distearoyl phosphatidylcholine (DSPC),
Dioleoyl phosphatidylcholine (DUPC),
Palmitoyl oleoyl phosphatidylcholine (POPC),
1,2-Di-O-octadecyl-sn-glycero-3-phosphocholine (18:0 Diether PC),
1-Oleoyl-2-cholesteryldimethylsuccinoyl-sn-glycero-3-phosphocholine (OChemsPC),
1-Hexadecyl-sn-glycero-3-phosphocholine (C16 Lyso PC),
1,2-Divinyl-sn-glycero-3-phosphocholine,
1,2-Diarylacyl-sn-glycero-3-phosphocholine,
1,2-Dioleoyl-sn-glycero-3-phosphorylethanolamine (DOPE),
1,2-Di-phytanoyl-sn-glycero-3-phosphoethanolamine (ME 16.0 PE),
1,2-Distearoyl-sn-glycero-3-phosphoethanolamine,
1,2-Diethenol-sn-glycero-3-phosphoethanolamine,
1,2-Divinyl-sn-glycero-3-phosphoethanolamine,
1,2-Diaryl-sn-glycero-3-phosphoethanolamine,
1,2-Dithiohexa-enoate-sn-glycero-3-phosphoethanolamine,
1,2-dioleoyl-sn-glycero-3-phosphate-(1-glycerol) sodium salt (DOPG) or sphingomyelin.

27. The nanoparticle composition according to item 25, wherein said phospholipid is DOPE.

28. The nanoparticle composition according to item 25, wherein said phospholipid is DSPC.

29. The nanoparticle composition according to any one of items 24 to 28, wherein said lipid component further comprises a structural lipid.

30. The nanoparticle composition according to item 29, wherein said structural lipid is selected from one, two or more of cholesterol, coprosterol, sitosterol, ergosterol, stigmasterol.

31. The nanoparticle composition according to item 29, wherein said structural lipid is cholesterol.

32. The nanoparticle composition according to any one of items 24 to 31, wherein said lipid component further comprises a PEG lipid.

33. The nanoparticle composition according to item 32, wherein said PEG lipid is selected from one, two or more of PEG-modified phosphatidylethanolamine, PEG-modified phosphatidic acid, PEG-modified ceramide, PEG-modified dialkylamine, PEG-modified diacylglycerol or PEG-modified dialkylglycerol.

34. The nanoparticle composition according to any one of items 24 to 33, wherein said lipid component further comprises cationic and/or ionizable lipid.

35. The nanoparticle composition according to any one of items 24 to 34, further comprising a therapeutic and/or prophylactic agent which is selected from vaccines, or compounds capable of eliciting an immune response, nucleic acids, preferably said nucleic acid is RNA, and said RNA is selected from one, two or more of siRNA, aiRNA, miRNA, dsRNA, shRNA or mRNA.

36. The nanoparticle composition according to any one of items 24 to 35, wherein the encapsulation efficiency of said therapeutic and/or prophylactic agent is ≥50%; or ≥80%; or ≥90%.

37. The nanoparticle composition according to any one of items 24 to 36, wherein said nanoparticle composition has an average particle size of 50 nm-110 nm.

38. The nanoparticle composition according to any one of items 24 to 36, wherein said nanoparticle composition has a polydispersity index of 0.04-0.20.

39. Use of the compound according to any one of items 1-20 in the preparation of a lipid nanoparticle composition.

40. A pharmaceutical composition comprising the nanoparticle composition according to any one of items 24 to 38 and a pharmaceutically acceptable carrier.

41. A method of delivering a therapeutic and/or prophylactic agent to a mammalian cell, comprising administering the nanoparticle composition according to any one of items 24 to 38 or the pharmaceutical composition according to item 40 to a subject, said administration comprises contacting the cell with said nanoparticle composition or said pharmaceutical composition to deliver the therapeutic and/or prophylactic agent to the cell.

42. The method according to item 41, wherein the mammalian cell is in a mammal.

43. The method according to item 41 or 42, wherein the mammal is a human.

44. The method according to any one of items 41 to 43, wherein said nanoparticle composition is administered intravenously, intramuscularly, intradermally, subcutaneously, intranasally, or by inhalation.

45. A method of producing the polypeptide of interest in a mammalian cell, comprising contacting the cell with the nanoparticle composition according to any one of claims 24 to 38 or the pharmaceutical composition according to item 40 to deliver a therapeutic and/or prophylactic agent to the cell, wherein said therapeutic and/or prophylactic agent is mRNA coding the polypeptide of interest, whereby the mRNA is capable of being translated in the cell to produce the polypeptide of interest.

46. The method according to item 45, wherein the mammalian cell is in a mammal.

47. The method according to any one of items 45 or 46, wherein the mammal is a human.

48. The method according to any one of items 45 to 47, wherein the nanoparticle composition or pharmaceutical composition is administered intravenously, intramuscularly, intradermally, subcutaneously, intranasally, or by inhalation.

49. A method of treating a disease or condition in a mammal, comprising administering a therapeutically effective amount of the nanoparticle composition according to any one of items 24 to 38 or the pharmaceutical composition according to item 40 to the mammal.

50. The method according to item 49, wherein said disease or condition is characterized by dysfunction or abnormality of activity of protein or polypeptide.

51. The method according to items 49 or 50, wherein said disease or condition is selected from infectious diseases, cancer and proliferative diseases, genetic diseases, autoimmune diseases, diabetes, neurodegenerative diseases, cardiovascular diseases, renal vascular diseases or metabolic diseases.

52. The method according to any one of items 49 to 51, wherein the mammal is a human.

53. The method according to any one of items 49 to 52, wherein the nanoparticle composition or pharmaceutical composition is administered intravenously, intramuscularly, intradermally, subcutaneously, intranasally, or by inhalation.

54. A method of specifically delivering a therapeutic and/or prophylactic agent to a mammalian organ, comprising administering the nanoparticle composition according to any one of items 24 to 38 or the pharmaceutical composition according to item 40 to the mammal, said administration comprises contacting the mammalian organ with said nanoparticle composition or pharmaceutical composition, thereby delivering the therapeutic and/or prophylactic agent to the organ.

55. The method according to item 54, wherein the mammal is a human.

56. The method according to item 54 or 55, wherein the nanoparticle composition is administered intravenously, intramuscularly, intradermally, subcutaneously, intranasally, or by inhalation.

57. The method according to any one of items 54 to 56, wherein said mammal is pretreated 24 hours prior to the contacting or administering step or less hours.

58. The method according to any one of items 54 to 57, wherein said mammal is pre-treated about one hour prior to the contacting or administering step.

Effects of the Invention

The compound of the present application can be used for the preparation of lipid nanoparticles, and the nanoparticle composition containing the compound of the present application can achieve encapsulation and delivery of the therapeutic agent/prophylactic agent, deliver the therapeutic agent/prophylactic agent to a target site safely, achieve high expression, and exert the effects of the therapeutic/prophylactic agent.

The lipid nanoparticles prepared in the present application have the advantages of small average particle size, high encapsulation efficiency and low toxicity, which has wide application prospects in the field of drug delivery.

The present application reported a synthetic method of the cationic lipid with asymmetric tail chains and containing an acetal structure for the first time. Firstly, two different bromo-substituted tail-chain compounds were synthesized; subsequently, nucleophilic substitution reactions with tosyl isocyanide were sequentially carried out under different alkaline conditions to obtain tosyl isocyanide-substituted double-long-chain compounds; and finally, double-tail-chain carbon compounds as the key intermediates were obtained by acid hydrolysis.

Specific Embodiments

In the following description of exemplary embodiments of the present application, various details of the embodiments of the present application are included to aid in understanding, which should be construed as merely illustrative. Accordingly, those of ordinary skill in the art will recognize that various changes and modifications of the embodiments described herein can be made without departing from the scope and spirit of the present application. Also, descriptions of well-known functions and structures are omitted in the following description for clarity and conciseness.

Terms and Definitions

As used herein, the term "alkyl" refers to a group containing one or more carbon atoms (for example, one, two, three, four, five, six, seven, eight, nine, ten, eleven, twelve, thirteen, fourteen, fifteen, sixteen, seventeen, eighteen, nineteen, twenty or more carbon atoms), which is optionally substituted. The term "C1-C14alkyl" refers to an optionally substituted linear or branched saturated hydrocarbon containing from 1 to 14 carbon atoms. Unless otherwise indicated, alkyl groups described herein refer to both unsubstituted and substituted alkyl groups.

As used herein, the term "carbocyclic ring" or "carbocyclyl" refers to an optionally substituted monocyclic or polycyclic system comprising one or more carbon rings. The ring may be a three, four, five, six, seven, eight, nine, ten, eleven, twelve, thirteen, fourteen, fifteen, sixteen, seventeen, eighteen, nineteen or twenty membered ring. The term "5-7 membered ring" refers to monocyclic, fused, spiro carbocyclic rings having 5-7 carbon atoms. Carbocyclic rings may include one or more carbon-carbon double bonds or triple bonds and may be non-aromatic or aromatic (e.g., cycloalkyl or aryl). Examples of carbocyclic rings include cyclopentyl, cyclohexyl, phenyl, naphthyl, and 1, 2-dihydronaphthyl.

As used herein, "cycloalkyl" refers to a non-aromatic carbocyclic ring, and may include or may not include any double or triple bonds. Unless otherwise indicated, carbocyclic ring described herein refers to unsubstituted and substituted carbocyclic groups, i.e. an optionally substituted carbocyclic ring.

As used herein, the term "heterocyclic ring" or "heterocyclyl" refers to an optionally substituted monocyclic or polycyclic system comprising one or more rings, wherein at least one of the rings comprises at least one heteroatom, such as one, two, three, four or five heteroatoms, which may be, for example, nitrogen, oxygen or sulfur atoms. The ring may be a three, four, five, six, seven, eight, nine, ten, eleven, twelve, thirteen or fourteen membered ring. The heterocyclic ring may include one or more double or triple bonds and may be non-aromatic or aromatic (e.g., heterocycloalkyl or heteroaryl). Examples of heterocyclic rings include imidazolyl, imidazolinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrryl, pyrrolyl group, pyrrolyl, pyrrolyl, furanyl, thienyl, pyrrolyl, pyrrolyl, pyrrolyl, furyl, thienyl, phenyl.

As used herein, the term "heterocycloalkyl" refers to a non-aromatic heterocyclic ring and may include or may not include any double or triple bond. Unless otherwise indicated, heterocyclic ring as used herein refers to unsubstituted and substituted heterocyclic groups, i.e., optionally substituted heterocyclic rings.

As used herein, "aryl" is an optionally substituted carbocyclic group comprising one or more aromatic rings. Examples of aryl groups include phenyl and naphthyl.

As used herein, "heteroaryl" refers to an optionally substituted heterocyclic group comprising one or more aromatic rings. Examples of heteroaryl include pyrrolyl, furanyl, thienyl, imidazolyl, oxazolyl, and thiazolyl. Both aryl and heteroaryl may be optionally substituted. Unless otherwise indicated, aryl or heteroaryl as used herein refers to unsubstituted and substituted groups, i.e., optionally substituted aryl or heteroaryl.

Unless otherwise indicated, the alkyl group may be optionally substituted. Optional substituents may be selected from, but are not limited to, halogen atom (e.g., chloro, bromo, fluoro, or iodo group), carboxylic acid (e.g., —C(O)OH), alcohol (e.g., hydroxyl, —OH), ester (e.g., —C(O)OR or —OC(O)R), aldehyde (e.g., —C(O)H), carbonyl group (e.g., —C(O)R, or denoted by C=O), acyl halide (e.g., —C(O)X, wherein X is a halide selected from bromide, fluoride, chloride, and iodide), carbonate (e.g., —OC(O)OR), alkoxy (e.g., —OR), acetal, phosphate, thiol (e.g., —SH), sulfoxide (e.g., —S(O)R), sulfurous acid group (e.g., —S(O)OH), sulfonic acid group (e.g., —S(O)$_2$OH), thiol (e.g., —C(S)H), sulfate, sulfonyl (e.g. —S(O)$_2$—), amide (e.g. —C(O)NR$_2$ or —N(R)C(O)R), azide (e.g. —N$_3$), nitro (e.g. —NO$_2$), cyano (e.g. —CN), isocyano (e.g. —NC), acyloxy (e.g. —OC(O)R), amino (e.g. —NR$_2$, —NRH, or —NH$_2$), carbamoyl (e.g. —OC(O)NR$_2$, —OC(O)NRH or —OC(O)NH$_2$), sulfonamide, alkyl, alkenyl and cyclic groups (e.g., carbocyclyl or heterocyclyl). In any one of the proceedings, R is alkyl or alkenyl as defined herein. In some embodiments, the substituent itself may be further substituted with, for example, one, two, three, four, five or six substituents as defined herein. For example, C$_{1-6}$ alkyl may be further substituted with 1, 2, 3, 4, 5, or 6 substituents described herein.

As used herein, the term "compound" is meant to include all isomers and isotopes of the described structures. "Isotope" refers to atoms having the same atomic number but differing in mass number due to the difference in neutron numbers in the nucleus. For example, isotopes of hydrogen include tritium and deuterium. In addition, the compounds, salts or complexes of the present application may be used to form solvates and hydrates by preparation through conventional methods in combination with solvent or water molecules.

As used herein, the term "contacting" refers to establishing a physical connection between two or more entities. For example, contacting a mammalian cell with a nanoparticle composition means that the mammalian cell and the nanoparticle share a physical connection. Methods for contacting cell with external entities, both in vivo and ex vivo, are well known in the biological field. For example, the nanoparticle composition may contact with a mammalian cell in a mammal by a variety of routes of administration (e.g., intravenous, intramuscular, intradermal, and subcutaneous), and various amounts of the nanoparticle composition may be involved. In addition, the nanoparticle composition may contact more than one mammalian cell.

As used herein, the term "delivery" refers to providing an entity to a target site. For example, delivering a therapeutic and/or prophylactic agent to a subject may include administering a nanoparticle composition containing a therapeutic and(or) prophylactic agent to a subject (e.g., by intravenous, intramuscular, intradermal, or subcutaneous routes). Administering a nanoparticle composition to a mammal or mammalian cell may involve contacting one or more cells with the nanoparticle composition.

As used herein, the term "enhance delivery" refers to delivering more (e.g., at least 1.5-fold, at least 2-fold, at least 3-fold, at least 4-fold, at least 5-fold, at least 6-fold, at least 7-fold, at least 8-fold, at least 9-fold, at least 10-fold) therapeutic and/or prophylactic agent by the nanoparticle to a target tissue of interest (e.g., mammalian liver), compared to the level of therapeutic and/or prophylactic agent delivered by a control nanoparticle to the target tissue (e.g., MC3, KC2, or DLinDMA). The comparison may be done by comparing the amount of protein produced in the tissue to the weight of said tissue, comparing the amount of therapeutic and/or prophylactic agent in the tissue to the weight of the tissue, comparing the amount of protein produced in the tissue to the amount of total protein in the tissue, or comparing the amount of therapeutic and/or prophylactic agent in the tissue to the total amount of therapeutic and/or prophylactic agent in said tissue. It is to be understood that the enhanced delivery of nanoparticles to a target tissue is not necessary to be determined in the subject being treated, but may be determined in an alternative such as an animal model (e.g., rat model). In certain embodiments, the nanoparticle compositions comprising a compound of formula (I), (IA), (IB), (IC), (ID) have substantially the same level of delivery enhancement, regardless of the route of administration.

As used herein, the term "specific delivery" or "specifically delivering" refers to delivering more (e.g., at least 1.5-fold, at least 2-fold, at least 3-fold, at least 4-fold, at least 5-fold, at least 6-fold, at least 7-fold, at least 8-fold, at least 9-fold, at least 10-fold) therapeutic and/or prophylactic agent to a target tissue (e.g., mammalian liver, spleen, stomach, intestinal tract) by a nanoparticle as compared to a non-target tissue. The level of nanoparticle delivery to a particular tissue may be measured by comparing the weight of protein produced in the tissue to the weight of said tissue, comparing the amount of therapeutic and/or prophylactic agent in the tissue to the weight of the tissue, comparing the weight of protein produced in the tissue to the weight of total protein in said tissue, or comparing the amount of therapeutic and/or prophylactic agent in the tissue to the total amount of therapeutic and/or prophylactic agent in said tissue.

As used herein, "encapsulation efficiency" refers to the amount of therapeutic and/or prophylactic agent that becomes part of a nanoparticle composition, relative to the total amount of therapeutic or prophylactic agent used in the preparation of the nanoparticle composition. For example, if 97 mg of the therapeutic and/or prophylactic agent is encapsulated in a nanoparticle composition out of a total of 100 mg of therapeutic and/or prophylactic agent initially provided for the composition, the encapsulation efficiency may be 97%. As used herein, "encapsulation" may refer to complete, substantial, or partial encapsulation, closure, enclosure, or envelopment.

As used herein, "expression" of a nucleic acid sequence refers to translation of mRNA into a polypeptide or protein and/or post-translational modification of a polypeptide or protein.

As used herein, the term "in vitro" refers to events that occur in an artificial environment, such as in a test tube or reaction vessel, in a cell culture, in a culture dish, etc., rather than events that occur within an organism. (e.g., animal, plant, or microorganism).

As used herein, the term "in vivo" refers to events that occur within an organism (e.g., an animal, plant, or microorganism or a cell or tissue thereof).

As used herein, the term "ex vivo" refers to events that occur outside an organism (e.g., an animal, plant or microorganism or a cell or tissue thereof). An ex vivo event may occur in an environment that is minimally altered from the natural (e.g., in vivo) environment.

As used herein, the term "isomer" refers to any geometric isomer, tautomer, zwitterion, stereoisomer, enantiomer or diastereoisomer of a compound. The compounds may contain one or more chiral centers and/or double bonds and thus may exist as stereoisomers, such as double bond isomers (i.e., geometric E/Z isomers) or diastereomers (e.g., enantiomers (i.e., (+) or (−)) or cis-trans isomers). The present application encompasses any and all isomers of the compounds described herein. Enantiomeric and stereoisomeric mixtures of compounds and methods of resolving them into their component enantiomers or stereoisomers are well known.

As used herein, "lipid component" is a component of a nanoparticle composition that includes one or more lipids. For example, the lipid component may include one or more cationic/ionizable lipids, pegylated lipids, structural lipids, or other lipids, such as phospholipids.

As used herein, "linker" is a moiety that connects two moieties, e.g., a linkage between two nucleosides of a cap. The linker may include one or more groups including, but are not limited to, phosphate groups (e.g., phosphate, borophosphate, thiophosphate, selenophosphate, and phosphonate), alkyl, amide, or glycerol. For example, the two nucleosides of a cap analog may be linked at their 5' positions by a triphosphate group or by a chain comprising two phosphate moieties and a borophosphate moiety.

As used herein, "method of administration" may include intravenous, intramuscular, intradermal, subcutaneous administration, or other methods of delivering a composition to a subject.

Any one of the methods of administration may be selected for targeted delivering (e.g., specifically delivering) to a particular region or system of a body.

As used herein, "modified" refers to non-natural. For example, the RNA may be a modified RNA. That is, the RNA may include one or more non-naturally occurring nucleobases, nucleosides, nucleotides, or linkers. A "modified" material may also be referred to herein as an "engineered" material. The substance may be chemically, structurally or functionally modified or altered. For example, the modified nucleobase species may comprise one or more non-naturally occurring substitutions.

As used herein, "nanoparticle composition" is a composition comprising one or more lipids. The particle size of the nanoparticle composition is typically on the order of microns or less, and may include a lipid bilayer. A nanoparticle composition includes a lipid nanoparticle (LNP), liposome (e.g., lipid vesicle), and lipid complex. For example, a nanoparticle composition may be a liposome having a lipid bilayer of 500 nm or less in diameter.

As used herein, "naturally occurring" means existing naturally without artificial assistance.

As used herein, "patient" refers to a subject who may seek or need treatment, requires treatment, is undergoing treatment, is about to undergo treatment, or is being cared for a particular disease by a trained professional.

As used herein, "PEG lipid" or "pegylated lipid" refers to a lipid comprising a polyethylene glycol component.

The term "pharmaceutically acceptable" is used herein to refer to those compounds, materials, compositions, and/or dosage forms which are, within the scope of rational medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically acceptable excipient" refers to any ingredient other than the compounds described herein (e.g., a vehicle capable of suspending, complexing, or dissolving the active compound) and which is substantially non-toxic and non-inflammatory to the patient. Excipients may include, for example: antiadherents, antioxidants, binders, coatings, compression aids, disintegrants, dyes (colorants), moistening agent, emulsifiers, fillers (diluents), film formers or coatings, flavors, fragrances, glidants (flow enhancers), lubricants, preservatives, printing inks, adsorbents, suspending or dispersing agents, sweeteners and water for hydration. Exemplary excipients include, but are not limited to: butylated hydroxytoluene (BHT), calcium carbonate, calcium phosphate (dibasic acid), calcium stearate, croscarmellose, crosslinked polyvinylpyrrolidone, citric acid, crospovidone, cysteine, ethylcellulose, gelatin, hydroxypropylcellulose, hydroxypropylmethylcellulose, lactose, magnesium stearate, maltitol, mannitol, methionine, methylcellulose, methylparaben, microcrystalline cellulose, polyethylene glycol, polyvinylpyrrolidone, povidone, pregelatinized starch, propyl paraben, retinyl palmitate, shellac, silicon dioxide, sodium carboxymethylcellulose, sodium citrate, sodium starch glycolate, sorbitol, starch (corn), stearic acid, sucrose, talc, titanium dioxide, vitamin A, vitamin E (alpha-tocopherol), vitamin C, xylitol and others disclosed herein.

In the present application, the structural formula of the compound shows certain isomers for convenience, but the present application includes all isomers, such as geometric isomers, optical isomers based on asymmetric carbon, stereoisomers, tautomers and the like, and it should be understood that not all isomers may have the same activity level.

In addition, the crystalline polymorphism may be present in the compounds represented by the structural formulae of the compounds described in the present application. It is noted that any crystalline form, mixture of crystalline forms or anhydride or hydrate thereof is included within the scope of the present application.

The terms "crystalline polymorph", "polymorph", or "crystalline form" refer to a crystal structure in which a compound (or a salt or solvate thereof) may crystallize in different crystal packing arrangements, all of which have the same elemental composition. Different crystalline forms typically have different X-ray diffraction patterns, infrared spectra, melting points, density hardnesses, crystal shapes, optical and electrical properties, stabilities and solubilities. Recrystallization solvent, crystallization rate, storage temperature and other factors may cause one form to predominate. Crystalline polymorphs of a compound may be prepared by crystallization under different conditions.

The nanoparticle compositions of the present application may further comprise one or more salts of a compound. The salt may be a pharmaceutically acceptable salt. As used herein, "pharmaceutically acceptable salts" refer to derivatives of the disclosed compounds wherein the parent compound is altered by converting an existing acid or base moiety into its salt form (e.g., by reacting the free base with a suitable organic acid). Examples of pharmaceutically acceptable salts include, but are not limited to, inorganic or organic acid salts of basic residues such as amines; base or organic salts of acidic residues such as carboxylic acids, and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, hydrobromide, hydrochloride, hydroiodide, 2-hydroxy-ethanesulfonate, lactate, laurate, lauryl sulfate, malate, maleate, malonate, methanesulfonate, 2-naphthalenesulfonate, nicotinate, nitrate, oleate, oxalate, palmitate, hexadecanoate, pectate, 3-phenylpropionate, phosphate, picrate, pivalate, propionate, stearate, succinate, sulfate, tartrate, thiocyanate, tosylate, undecanoate, valerate salts and the like.

Representative alkali metal or alkaline earth metal salts include sodium, lithium, potassium, calcium, magnesium, and the like, as well as non-toxic ammonium, quaternary ammonium, and amine cations including, but are not limited to, ammonium, tetramethyl ammonium, tetraethyl ammonium, methylamine, dimethylamine, trimethylamine, triethylamine, ethylamine, and the like. Pharmaceutically acceptable salts of the present application include, for example, conventional non-toxic salts of the parent compound formed from non-toxic inorganic or organic acids. The pharmaceutically acceptable salts of the present application may be synthesized by conventional chemical methods from parent compounds containing basic or acidic portions. Typically, these salts may be prepared by reacting the free acidic or basic forms of these compounds with chemically calculated amounts of suitable bases or acids in water or in organic solvents or in mixtures of both. Typically, non-aqueous media such as ether, ethyl acetate, ethanol, isopropanol or acetonitrile are preferred.

As used herein, "phospholipid" is a lipid that includes a phosphate moiety and one or more carbon chains, e.g., unsaturated fatty acid chains. The phospholipid may comprise one or more multiple (e.g. double or triple bond) bonds (e.g. one or more unsaturated bonds). Certain phospholipids may promote fusion with the membrane. For example, a cationic phospholipid may interact with one or more negatively charged phospholipids of a membrane (e.g., a cell membrane or an intracellular membrane). The fusion of the phospholipid to the membrane may allow one or more elements of the lipid-containing composition to pass through the membrane, thereby allowing, for example, delivery of the one or more elements to the cell.

As used herein, "polydispersity index" is a ratio describing the uniformity of the particle size distribution of a system. Relatively small values, for example less than 0.3, indicate a narrow particle size distribution.

As used herein, the term "polypeptide" or "polypeptide of interest" refers to a polymer of amino acid residues, typically linked by peptide bonds, which may be produced naturally (e.g., isolated or purified) or synthetically.

As used herein, "RNA" refers to ribonucleic acids that may or may not occur naturally. For example, the RNA may include modified and/or non-naturally occurring components, such as one or more nucleobases, nucleosides, nucleotides, or linkers. The RNA may include a cap structure, a chain terminating nucleoside, a stem loop, a polyA sequence, and/or a polyadenylation signal. The RNA may have a nucleotide sequence encoding a polypeptide of interest. For example, the RNA may be messenger RNA (mRNA). Translation of mRNA encoding a particular polypeptide, e.g., in vivo translation of mRNA inside a mammalian cell, may result in the encoded polypeptide. RNA may be selected from the non-limiting group consisting of small interfering RNA (siRNA), asymmetric interfering RNA (airRNA), micro RNA (miRNA), double stranded RNA (dsRNA), small hairpin RNA (shRNA), mRNA and mixtures thereof.

As used herein, "single unit dose" is a dose of any therapeutic agent that is administered at one dose/one time/single route/single contact point, i.e., a single administration.

As used herein, "divided doses" refers to that a single unit dose or total daily dose is divided into two or more doses.

As used herein, "total daily dose" is the amount given or prescribed over a 24-hour period. It may be administered in a single unit dose.

As used herein, "particle size" or "average particle size" in the context of a nanoparticle composition refers to the average diameter of the nanoparticle composition.

As used herein, the term "subject" or "patient" refers to any organism to which a composition according to the present application may be administered, e.g., for experimental, diagnostic, prophylactic and/or therapeutic purposes. Typical subjects include animals (e.g., mammals, such as mice, rats, rabbits, non-human primates, and humans) and/or plants.

As used herein, "target cell" refers to any one or more cells of interest. Cells may be found in vitro, in vivo, in situ, or in a tissue or organ of an organism. The organism may be an animal, preferably a mammal, more preferably a human, most preferably a patient.

As used herein, "target tissue" refers to any one or more tissue types of interest in which therapeutic and/or prophylactic delivery will result in a desired biological and/or pharmacological effect. Examples of target tissues include specific tissues, organs and systems or groups thereof. For particular uses, the target tissue may be kidney (e.g., intracoronary or intrafemoral), or blood vessels (e.g., by intratumoral injection) of kidney, lung, spleen, vascular endothelium. "Non-target tissue" is meant any tissue type or tissue types in which expression of the encoded protein does not result in the desired biological and/or pharmacological effect. For particular uses, non-target tissue may include liver and spleen.

The term "therapeutic agent" or "prophylactic agent" refers to any agent that, when administered to a subject, has a therapeutic, diagnostic and/or prophylactic effect and/or elicits a desired biological and/or pharmacological effect. Therapeutic agents are also referred to as "active agents" or "active components". Such substances include, but are not limited to, cytotoxins, radioactive ions, chemotherapeutic agents, small molecule drugs, proteins, and nucleic acids.

As used herein, the term "therapeutically effective amount" refers to an sufficient amount of an agent to be delivered (e.g., nucleic acid, drug, composition, therapeutic agent, diagnostic agent, prophylactic agent, etc.) for the following circumstance: administering to a subject suffering from or susceptible to an infection, disease, disorder, and/or condition for the purpose of treating, ameliorating symptoms thereof, diagnosing, preventing, and/or delaying the onset of the infection, disease, disorder, and/or condition.

As used herein, "transfection" refers to the introduction of a species (e.g., RNA) into a cell. Transfection may be performed, for example, in vitro, ex vivo or in vivo.

As used herein, the term "treatment" refers to partial or complete response, alleviation, amelioration, remission of specific infections, diseases, disorders and/or conditions, delaying its onset, inhibiting its progression, reducing its severity and/or reducing the incidence of one or more symptoms or signs thereof. For example, "treating" cancer may refer to inhibiting the survival, growth, and/or spread of a tumor. To reduce risk, a subject not exhibiting a disease, disorder, and/or condition, pathologically progressive condition associated with a disease, disorder and/or condition and/or a subject exhibiting only early signs of a disease, disorder, and/or condition, pathologically progressive condition associated with a disease, disorder and/or condition may be treated.

The present application discloses a compound described in formula (I), or a salt or an isomer thereof,

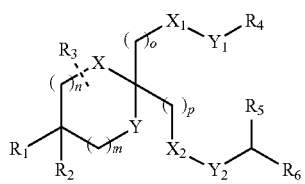

wherein X and Y are independently selected from O or S;
$X_1$ and $X_2$ are independently selected from C=O or O, $Y_1$ and $Y_2$ are independently selected from C=O or O, with the proviso that $X_1$ and $Y_1$ are not both C=O or O, and $X_2$ and $Y_2$ are not both C=O or O;
$R_1$ is

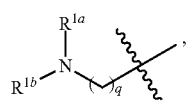

wherein $R^{1a}$ and $R^{1b}$ are independently selected from H or C1-C6alkyl, $R_2$, $R_3$ are independently selected from H or C1-C6alkyl, or $R_1$ and $R_2$, together with the carbon atom to which they are attached, form a substituted or unsubstituted 5-7 membered nitrogen-containing heterocyclic ring, and $R_3$ is selected from H or C1-C6alkyl, or
$R_1$ and $R_3$, together with the carbon atoms to which they are attached, form ring A, which is a substituted or unsubstituted carbocyclic or heterocyclic ring, and $R_2$ is selected from H or C1-C6alkyl;
$R_4$, $R_5$ and $R_6$ are independently selected from C1-C14alkyl;
m and n are independently selected from 0, 1, 2, with the proviso that m and n are not both 0;
o and p are independently selected from 1, 2, 3, 4, 5, 6, 7, 8, 9 or 10;
q is selected from 0, 1, 2, 3, 4, 5 or 6.

In a preferred embodiment, said $R_1$ is

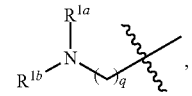

and in a specific embodiment, the compound of formula (I) is as shown in formula (IA),

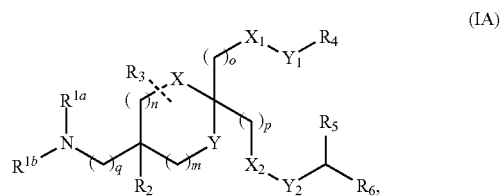

wherein q is preferably selected from 0, 1, 2, 3 or 4.
Further preferably, q is selected from 2 or 3.
Further preferably, q is selected from 2.
In a preferred embodiment, wherein the compound of formula (I) is of formula (IA),

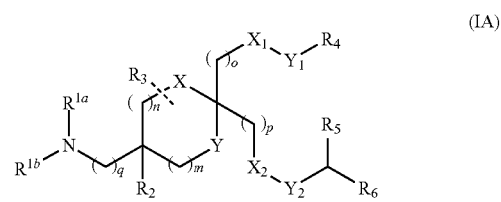

wherein q is selected from 2 or 3, and $R^{1a}$ and $R^{1b}$ are selected from —CH3, —CH2CH3 or —CH(CH3)$_2$,
$R_2$ is H, and $R_3$ is H,
n is 1, m is 0,
X, Y are both O,
o is 5 or 6,
p is 7,
$X_1$ and $X_2$ are both C=O, $Y_1$ and $Y_2$ is O, or $X_1$ is O, $Y_1$ is C=O, $X_2$ is C=O, and $Y_2$ is O,
$R_4$ is C10 linear alkyl or C11 linear alkyl,
$R_5$ and $R_6$ are C8 linear alkyl.
Further preferably, $R^{1a}$ and $R^{1b}$ are both selected from —CH3.

In a preferred embodiment, said $R_1$ and $R_2$, together with the carbon atom to which they are attached, form a substituted or unsubstituted 5-7 membered nitrogen-containing heterocyclic ring, $R_3$ is selected from H or C1-C6alkyl, in a specific embodiment, the compound of formula (I) is as shown in formula (IB),

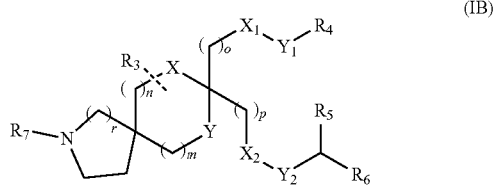
(IB)

wherein $R_7$ is selected from H or C1-C6alkyl; and r is selected from 0, 1, 2 or 3.

In a preferred embodiment, said $R_1$ and $R_3$, together with the carbon atoms to which they are attached, form ring A, which is a substituted or unsubstituted 5-7 membered carbocyclic or heterocyclic ring; $R_2$ is selected from H or C1-C6alkyl; in a specific embodiment, the compound of formula (I) is as shown in formula (IC),

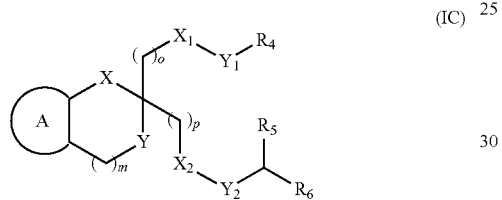
(IC)

wherein ring A is substituted by one or more $R_8$, said $R_8$ being

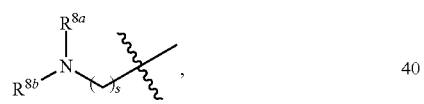

wherein $R^{8a}$ and $R^{8b}$ are independently selected from H or C1-C6alkyl, and s is selected from 0, 1, 2, 3, 4, 5 or 6.

In a specific embodiment, the compound of formula (I) is as shown in formula (ID),

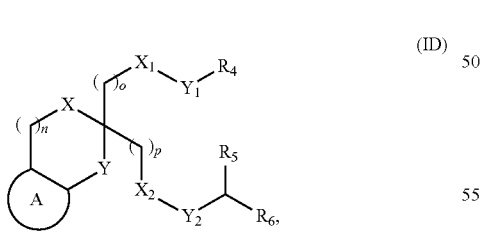
(ID)

wherein ring A is substituted by one or more $R_8$, said $R_8$ being

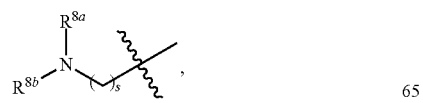

wherein $R^{8a}$ and $R^{8b}$ are independently selected from H or C1-C6alkyl, and s is selected from 0, 1, 2, 3, 4, 5 or 6.

In a specific embodiment, said ring A is

;

said compound of formula (IC) is as shown in (IC-1),

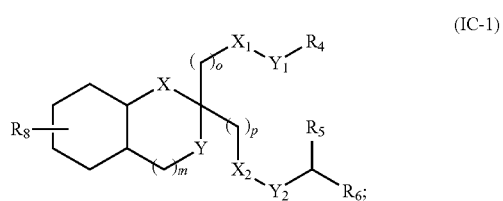
(IC-1)

The compound of formula (ID) is as shown in (ID-1),

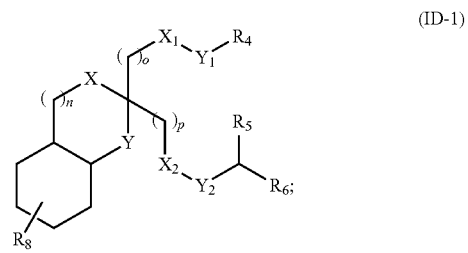
(ID-1)

In a specific embodiment, said ring A

;

said compound of formula (IC) is as shown in (IC-2),

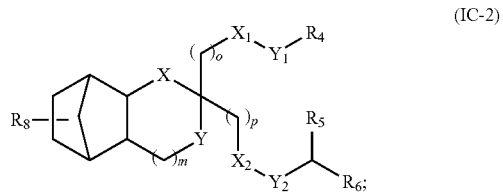
(IC-2)

The compound of formula (ID) is as shown in (ID-2),

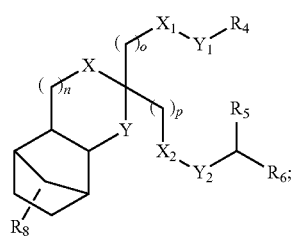
(ID-2)

In a specific embodiment, said ring A is

said compound of formula (IC) is as shown in (IC-3),

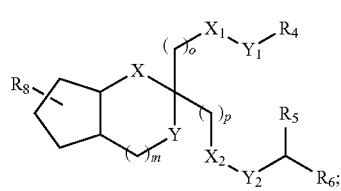
(IC-3)

The compound of formula (ID) is as shown in (ID-3),

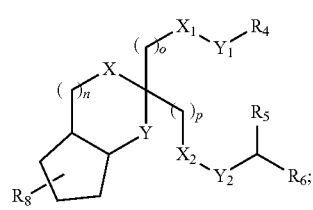
(ID-3)

In a specific embodiment, said ring A is

said compound of formula (IC) is as shown in (IC-3),

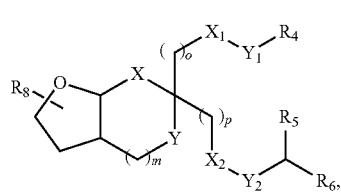
(IC-3)

said compound of formula (IC) is as shown in (IC-4),

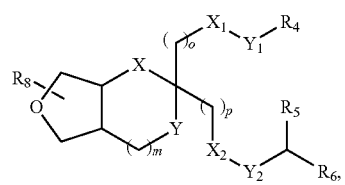
(IC-4)

or said compound of formula (IC) is as shown in (IC-5)

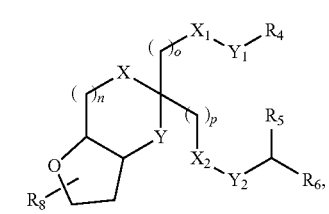
(IC-5)

The compound of formula (ID) is as shown in (ID-3),

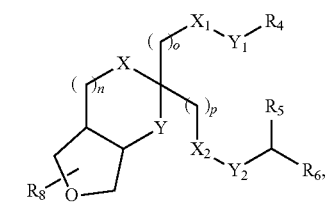
(ID-3)

the compound of formula (ID) is as shown in (ID-4),

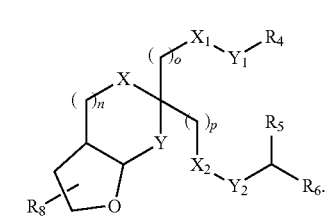
(ID-4)

or the compound of formula (ID) is as shown in (ID-5)

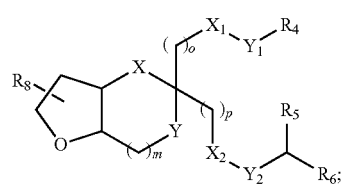
(ID-5)

In a preferred embodiment, in the above formula (I), (IA), (IIA), (IIA-A), (IIA-B), (IIA-C), (IIA-D), (IIA-E), (IIA-F), (IIA-G), (IIA-H), (IB), (IC), (IC-1), (IC-2), (IC-3), (IC-4), (IC-5), (ID), (ID-1), (ID-2), (ID-3), (ID-4), (ID-5), said $R_4$ is selected from C1-C14alkyl, for example, $R_4$ is selected from C2-C14alkyl, $R_4$ is selected from C3-C14alkyl, $R_4$ is selected from C4-C14alkyl, $R_4$ is selected from C5-C14alkyl, $R_4$ is selected from C6-C14alkyl, $R_4$ is selected from C7-C14alkyl, $R_4$ is selected from C8-C14alkyl, $R_4$ is selected from C9-C14alkyl, $R_4$ is selected from C10-C14alkyl, C10-C13alkyl, C10-C12alkyl, or C10-C11alkyl, for example, $R_4$ is C1alkyl, $R_4$ is C2alkyl, $R_4$ is C3alkyl, $R_4$ is C4alkyl, $R_4$ is C5alkyl, $R_4$ is C6alkyl, $R_4$ is C7alkyl, $R_4$ is C8alkyl, $R_4$ is C9alkyl, $R_4$ is C10alkyl, $R_4$ is C11alkyl, $R_4$ is C12alkyl, $R_4$ is C13alkyl, or $R_4$ is C14alkyl. In further preferred embodiments, $R_4$ is C10alkyl; in further preferred embodiments, $R_4$ is C11alkyl.

In a preferred embodiment, said $R_4$ is selected from C1-C14 linear alkyl, for example, $R_4$ is selected from C2-C14 linear alkyl, $R_4$ is selected from C3-C14 linear alkyl, $R_4$ is selected from C4-C14 linear alkyl, $R_4$ is selected from C5-C14 linear alkyl, $R_4$ is selected from C6-C14 linear alkyl, $R_4$ is selected from C7-C14 linear alkyl, $R_4$ is selected from C8-C14 linear alkyl, $R_4$ is selected from C9-C14 linear alkyl, $R_4$ is selected from C10-C14 linear alkyl, C10-C13 linear alkyl, C10-C12 linear alkyl, or C10-C11 linear alkyl, for example, $R_4$ is C1alkyl, $R_4$ is C2alkyl, $R_4$ is C3 linear alkyl, $R_4$ is C4 linear alkyl, $R_4$ is linear C5alkyl, $R_4$ is C6 linear alkyl, $R_4$ is C7 linear alkyl, $R_4$ is C8 linear alkyl, $R_4$ is C9 linear alkyl, $R_4$ is C10 linear alkyl, $R_4$ is C11 linear alkyl, $R_4$ is C12 linear alkyl, $R_4$ is C13 linear alkyl, or $R_4$ is C14 linear alkyl. In further preferred embodiments, $R_4$ is C10 linear alkyl; in further preferred embodiments, $R_4$ is C11 linear alkyl.

In a specific embodiment, the compound of formula (I) is as shown in formula (IA-1),

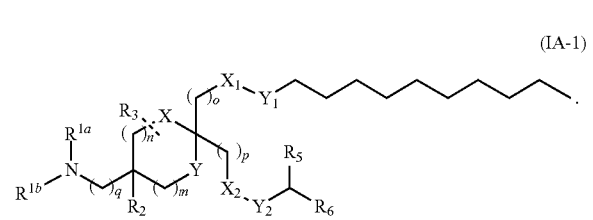

(IA-1)

In a specific embodiment, the compound of formula (I) is as shown in formula (IA-2),

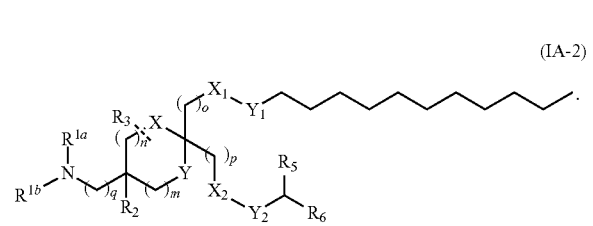

(IA-2)

In a specific embodiment, the compound of formula (I) is as shown in formula (IB-1),

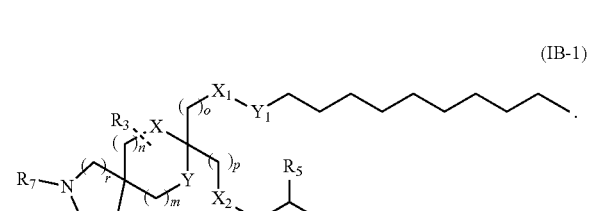

(IB-1)

In a specific embodiment, the compound of formula (I) is as shown in formula (IB-2),

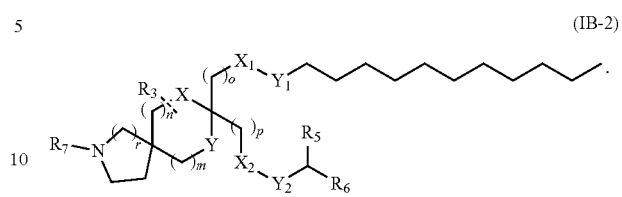

(IB-2)

In a specific embodiment, the compound of formula (I) is as shown in formula (IC-6),

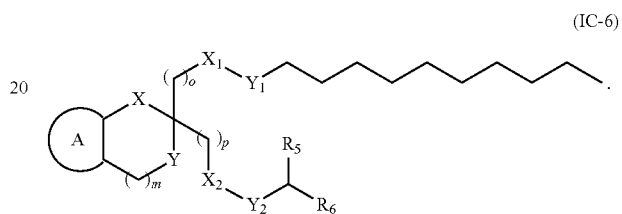

(IC-6)

In a specific embodiment, the compound of formula (I) is as shown in formula (IC-7),

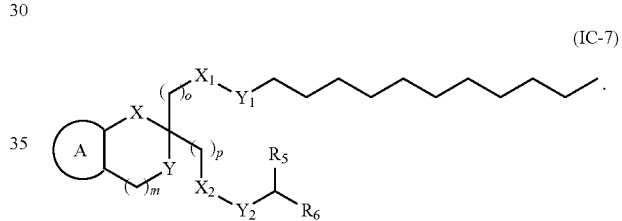

(IC-7)

In a specific embodiment, the compound of formula (I) is as shown in formula (ID-6),

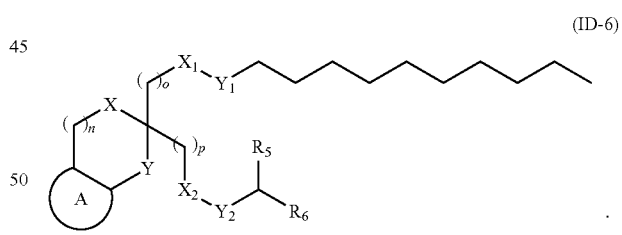

(ID-6)

In a specific embodiment, the compound of formula (I) is as shown in formula (ID-7),

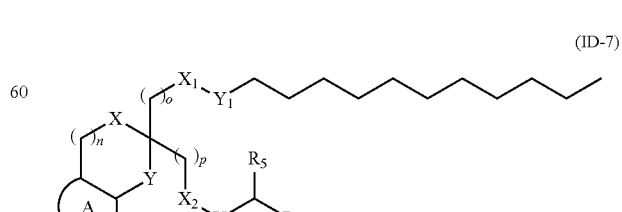

(ID-7)

In a preferred embodiment, in the above formula (I), (IA), (IA-1), (IA-2), (IIA), (IIA-A), (IIA-B), (IIA-C), (IIA-D), (IIA-E), (IIA-F), (IIA-G), (IIA-H), (IB), (IB-1), (IB-2), (IC), (IC-1), (IC-2), (IC-3), (IC-4), (IC-5), (IC-6), (IC-7), (ID), (ID-1), (ID-2), (ID-3), (ID-4), (ID-5), (ID-6), (ID-7), said $R_5$ is selected from C1-C14alkyl, for example, $R_5$ is selected from C2-C14alkyl, $R_5$ is selected from C3-C14alkyl, $R_5$ is selected from C4-C14alkyl, $R_5$ is selected from C5-C14alkyl, $R_5$ is selected from C6-C14alkyl, $R_5$ is selected from C7-C14alkyl, $R_5$ is selected from C8-C14alkyl, $R_5$ is selected from C8-C13alkyl, $R_5$ is selected from C8-C12alkyl, $R_5$ is selected from C8-C11alkyl, $R_5$ is selected from C8-C10alkyl, or $R_5$ is selected from C8-C9alkyl, for example, $R_5$ is C1alkyl, $R_5$ is C2alkyl, $R_5$ is C3alkyl, $R_5$ is C4alkyl, $R_5$ is C5alkyl, $R_5$ is C6alkyl, $R_5$ is C7alkyl, $R_5$ is C8alkyl, $R_5$ is C9alkyl, $R_5$ is C10alkyl, $R_5$ is C11alkyl, $R_5$ is C12alkyl, $R_5$ is C13alkyl, or $R_5$ is C14alkyl. In a preferred embodiment, said $R_5$ is C8alkyl.

In a preferred embodiment, said $R_5$ is selected from C1-C14 linear alkyl, for example, $R_5$ is selected from C2-C14 linear alkyl, $R_5$ is selected from C3-C14 linear alkyl, $R_5$ is selected from C4-C14 linear alkyl, $R_5$ is selected from C5-C14 linear alkyl, $R_5$ is selected from C6-C14 linear alkyl, $R_5$ is selected from C7-C14 linear alkyl, $R_5$ is selected from C8-C14 linear alkyl, $R_5$ is selected from C8-C13 linear alkyl, $R_5$ is selected from C8-C12 linear alkyl, $R_5$ is selected from C8-C11 linear alkyl, $R_5$ is selected from C8-C10 linear alkyl, or $R_5$ is selected from C8-C9 linear alkyl, for example, $R_5$ is C1alkyl, $R_5$ is C2alkyl, $R_5$ is C3 linear alkyl, $R_5$ is C4 linear alkyl, $R_5$ is linear C5alkyl, $R_5$ is C6 linear alkyl, $R_5$ is C7 linear alkyl, $R_5$ is C8 linear alkyl, $R_5$ is C9 linear alkyl, $R_5$ is C10 linear alkyl, $R_5$ is C11 linear alkyl, $R_5$ is C12 linear alkyl, $R_5$ is C13 linear alkyl, or $R_5$ is C14 linear alkyl. In a preferred embodiment, said $R_5$ is C8 linear alkyl.

In a preferred embodiment, in the above formula (I), (IA), (IA-1), (IA-2), (IIA), (IIA-A), (IIA-B), (IIA-C), (IIA-D), (IIA-E), (IIA-F), (IIA-G), (IIA-H), (IB), (IB-1), (IB-2), (IC), (IC-1), (IC-2), (IC-3), (IC-4), (IC-5), (IC-6), (IC-7), (ID), (ID-1), (ID-2), (ID-3), (ID-4), (ID-5), (ID-6), (ID-7), said $R_6$ is selected from C1-C14alkyl, for example, $R_6$ is selected from C2-C14alkyl, $R_6$ is selected from C3-C14alkyl, $R_6$ is selected from C4-C14alkyl, $R_6$ is selected from C5-C14alkyl, $R_6$ is selected from C6-C14alkyl, $R_6$ is selected from C7-C14alkyl, $R_6$ is selected from C8-C14alkyl, $R_6$ is selected from C8-C13alkyl, $R_6$ is selected from C8-C12alkyl, $R_6$ is selected from C8-C11alkyl, $R_6$ is selected from C8-C10alkyl, or $R_6$ is selected from C8-C9alkyl, for example, $R_6$ is C1alkyl, $R_6$ is C2alkyl, $R_6$ is C3alkyl, $R_6$ is C4alkyl, $R_6$ is C5alkyl, $R_6$ is C6alkyl, $R_6$ is C7alkyl, $R_6$ is C8alkyl, $R_6$ is C9alkyl, $R_6$ is C16alkyl, $R_6$ is C11alkyl, $R_6$ is C12alkyl, $R_6$ is C13alkyl, or $R_6$ is C14alkyl. In a preferred embodiment, said $R_6$ is C8alkyl.

In a preferred embodiment, said $R_6$ is selected from C1-C14 linear alkyl, for example, $R_6$ is selected from C2-C14 linear alkyl, $R_6$ is selected from C3-C14 linear alkyl, $R_6$ is selected from C4-C14 linear alkyl, $R_6$ is selected from C5-C14 linear alkyl, $R_6$ is selected from C6-C14 linear alkyl, $R_6$ is selected from C7-C14 linear alkyl, $R_6$ is selected from C8-C14 linear alkyl, $R_6$ is selected from C8-C13 linear alkyl, $R_6$ is selected from C8-C12 linear alkyl, $R_6$ is selected from C8-C11 linear alkyl, $R_6$ is selected from C8-C10 linear alkyl, or $R_6$ is selected from C8-C9 linear alkyl, for example, $R_6$ is C1alkyl, $R_6$ is C2alkyl, $R_6$ is C3 linear alkyl, $R_6$ is C4 linear alkyl, $R_6$ is linear C5alkyl, $R_6$ is C6 linear alkyl, $R_6$ is C7 linear alkyl, $R_6$ is C8 linear alkyl, $R_6$ is C9 linear alkyl, $R_6$ is C10 linear alkyl, $R_6$ is C11 linear alkyl, $R_6$ is C12 linear alkyl, $R_6$ is C13 linear alkyl, or $R_6$ is C14 linear alkyl. In a preferred embodiment, said $R_6$ is C8 linear alkyl.

In a preferred embodiment, said $R_5$ is C8alkyl, said $R_6$ is C8alkyl.

In a preferred embodiment, said $R_5$ is C8 linear alkyl, said $R_6$ is C8 linear alkyl.

In a specific embodiment, the compound of formula (I) is as shown in formula (IA-3),

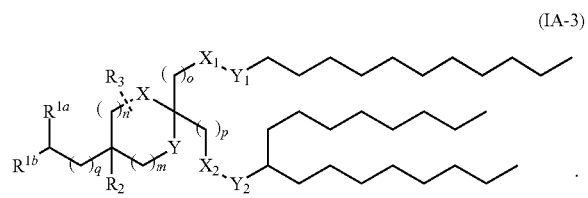

(IA-3)

In a specific embodiment, the compound of formula (I) is as shown in formula (IB-3),

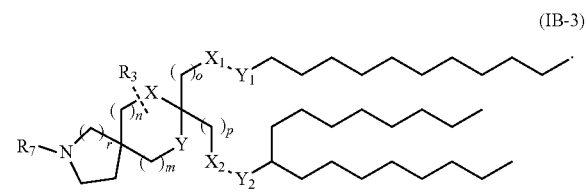

(IB-3)

In a specific embodiment, the compound of formula (I) is as shown in formula (IC-8),

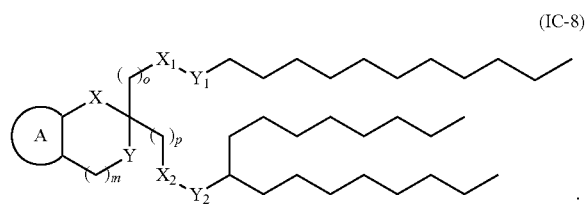

(IC-8)

In a specific embodiment, the compound of formula (I) is as shown in formula (ID-8),

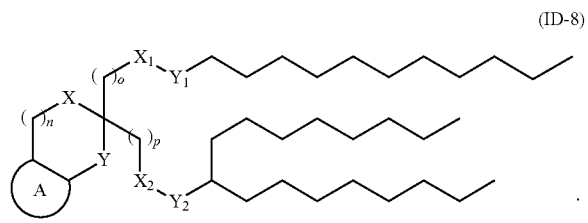

(ID-8)

In a preferred embodiment, said o is 5:
in a specific embodiment, the compound of formula (I) is as shown in formula (IA-4),

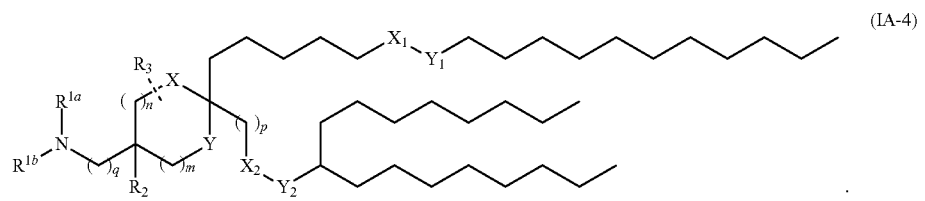

(IA-4)

In a specific embodiment, the compound of formula (I) is as shown in formula (IB-4),

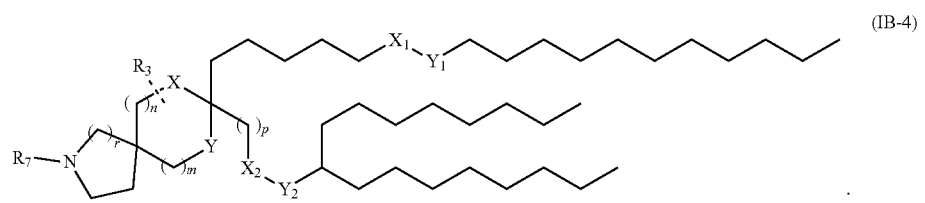

(IB-4)

In a specific embodiment, the compound of formula (I) is as shown in formula (IC-9), In a specific embodiment, the compound of formula (I) is as shown in formula (ID-9),

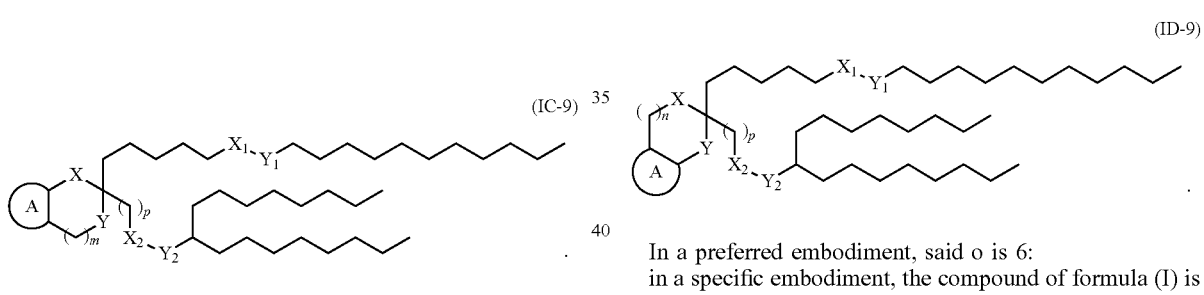

(IC-9)

(ID-9)

In a preferred embodiment, said o is 6:
in a specific embodiment, the compound of formula (I) is as shown in formula (IA-5),

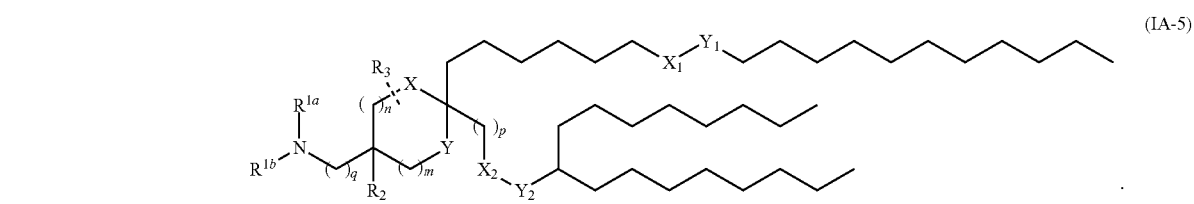

(IA-5)

In a specific embodiment, the compound of formula (I) is as shown in formula (IB-5),

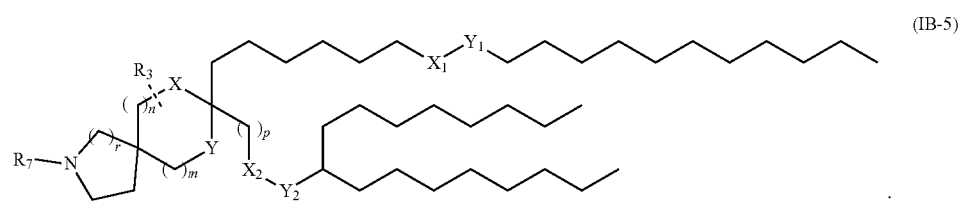

(IB-5)

In a specific embodiment, the compound of formula (I) is as shown in formula (IC-10),

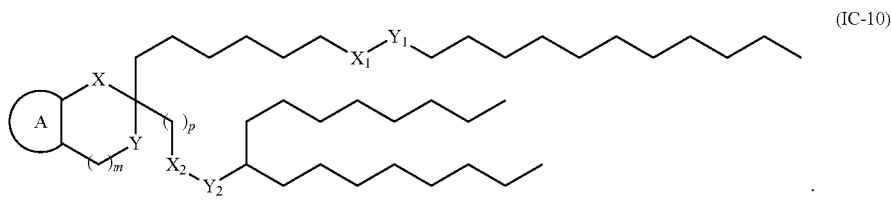
(IC-10)

In a specific embodiment, the compound of formula (I) is as shown in formula (ID-10),

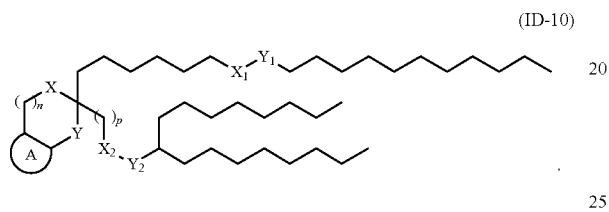
(ID-10)

In a preferred embodiment, said p is 7:
in a specific embodiment, the compound of formula (I) is as shown in formula (IA-6),

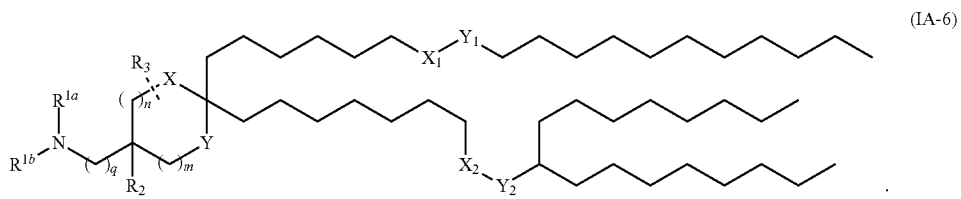
(IA-6)

In a specific embodiment, the compound of formula (I) is as shown in formula (IB-6),

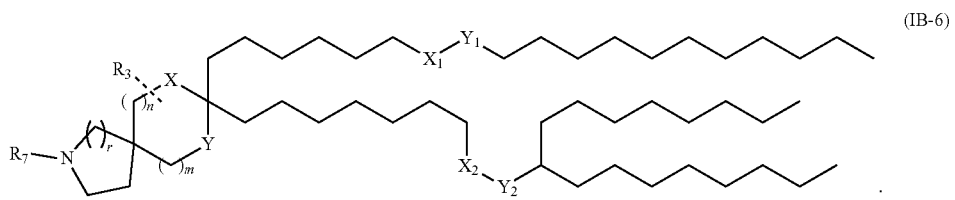
(IB-6)

In a specific embodiment, the compound of formula (I) is as shown in formula (IC-11),

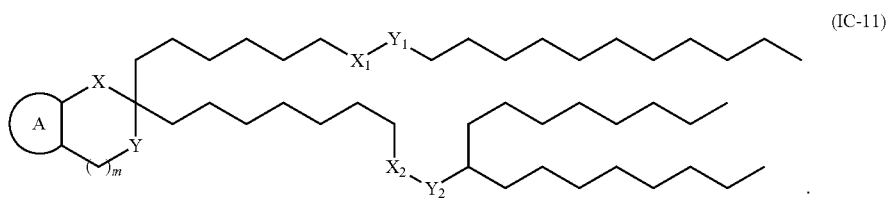
(IC-11)

In a specific embodiment, the compound of formula (I) is as shown in formula (ID-11), (ID-11)

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $X_1$ and $X_2$ are C=O, and said $Y_1$ and $Y_2$ are O.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $X_1$ is O, $Y_1$ is C=O, said $X_2$ is C=O, and $Y_2$ is O.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $X_1$ is C=O, $Y_1$ is O, said $X_2$ is O, and $Y_2$ is C=O.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $X_1$, $X_2$ are O, said $Y_1$ and $Y_2$ are C=O.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), and said X and Y are both O.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said n is 0, and m is 1.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said n is 1, and m is 0.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said n is 1, and m is 1.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said o is 1, 2, 3, 4, 5, 6, 7, 8, 9 or 10.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said p is 1, 2, 3, 4, 5, 6, 7, 8, 9 or 10.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said q is 0, 1, 2, 3, 4, 5 or 6.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said o is 5 or 6.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said p is 7 or 8.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said q is 2 or 3.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $R^2$ is H.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $R^3$ is H.

In a preferred embodiment, in the above formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), said $R^{1a}$ and $R^{1b}$ are —$CH_3$.

In a preferred embodiment, wherein the compound of formula (I) is Compound 1

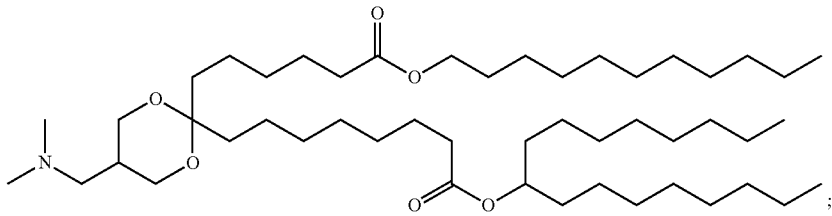 [SMILES: CCCCCCCCCCCOC(=O)CCCCCC1(CCCCCCCC(=O)OC(CCCCCCCC)CCCCCCCC)OCC(CN(C)C)CO1]

In a preferred embodiment, wherein the compound of formula (I) is Compound 2

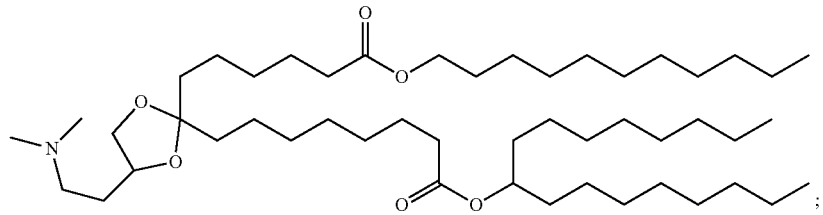 [SMILES: CCCCCCCCCCCOC(=O)CCCCCC1(CCCCCCCC(=O)OC(CCCCCCCC)CCCCCCCC)OCC(CCN(C)C)O1]

In a preferred embodiment, wherein the compound of formula (I) is Compound 3

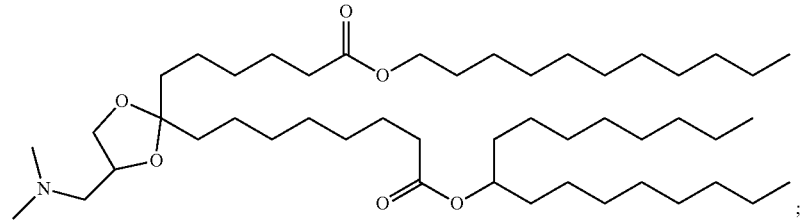 [SMILES: CCCCCCCCCCCOC(=O)CCCCCC1(CCCCCCCC(=O)OC(CCCCCCCC)CCCCCCCC)OCC(CN(C)C)O1]

In a preferred embodiment, wherein the compound of formula (I) is Compound 4
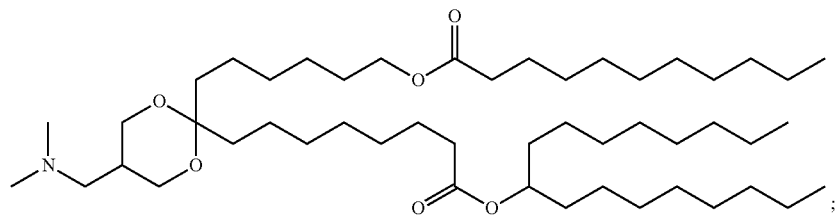 [SMILES: CCCCCCCCCCC(=O)OCCCCCCC1(CCCCCCCC(=O)OC(CCCCCCCC)CCCCCCCC)OCC(CN(C)C)CO1]
In a preferred embodiment, wherein the compound of formula (I) is Compound 5
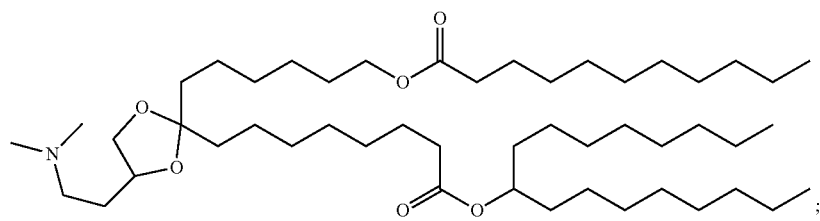 [SMILES: CCCCCCCCCCC(=O)OCCCCCCC1(CCCCCCCC(=O)OC(CCCCCCCC)CCCCCCCC)OCC(CCN(C)C)O1]
In a preferred embodiment, wherein the compound of formula (I) is Compound 6
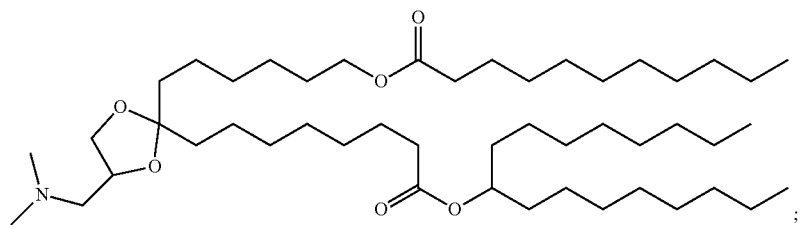 [SMILES: CCCCCCCCCCC(=O)OCCCCCCC1(CCCCCCCC(=O)OC(CCCCCCCC)CCCCCCCC)OCC(CN(C)C)O1]
In a preferred embodiment, wherein the compound of formula (I) is Compound 7
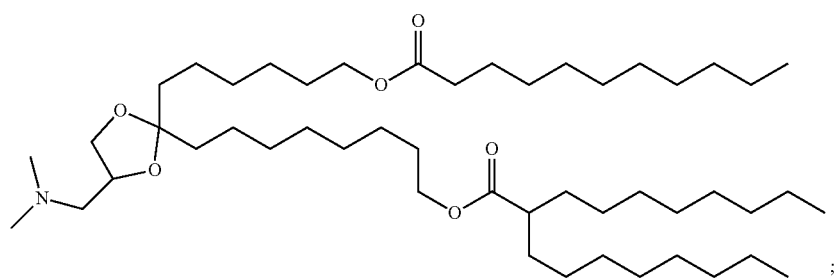 [SMILES: CCCCCCCCCCC(=O)OCCCCCCC1(CCCCCCCCOC(=O)C(CCCCCCCC)CCCCCCCC)OCC(CN(C)C)O1]

In a preferred embodiment, wherein the compound of formula (I) is Compound 8
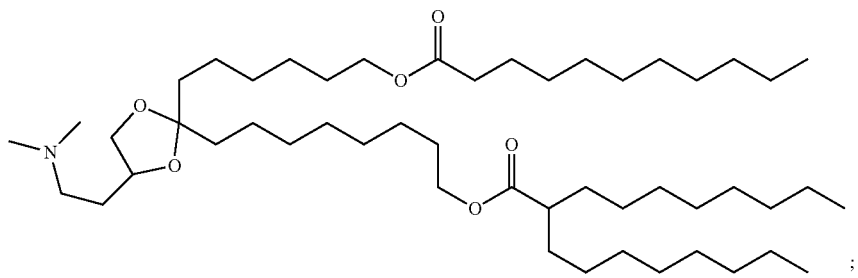 [SMILES: CCCCCCCCCCC(=O)OCCCCCCC1(CCCCCCCCOC(=O)C(CCCCCCCC)CCCCCCCC)OCC(CCN(C)C)O1]
In a preferred embodiment, wherein the compound of formula (I) is Compound 9
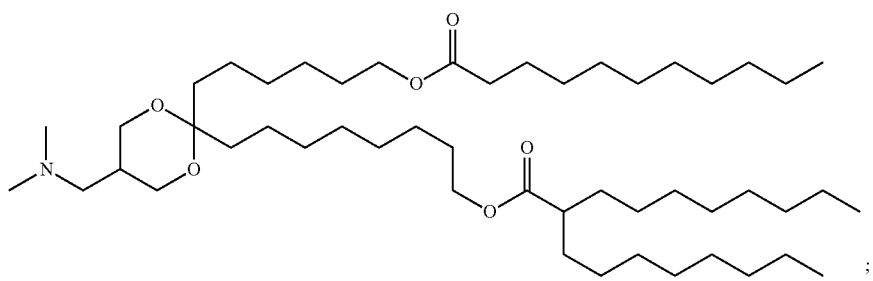 [SMILES: CCCCCCCCCCC(=O)OCCCCCCC1(CCCCCCCCOC(=O)C(CCCCCCCC)CCCCCCCC)OCC(CN(C)C)CO1]
In a preferred embodiment, wherein the compound of formula (I) is Compound 10
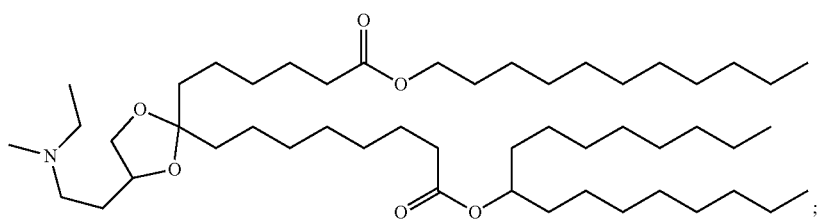 [SMILES: CCCCCCCCCCCOC(=O)CCCCCC1(CCCCCCCC(=O)OC(CCCCCCCC)CCCCCCCC)OCC(CCN(C)CC)O1]
In a preferred embodiment, wherein the compound of formula (I) is Compound 11
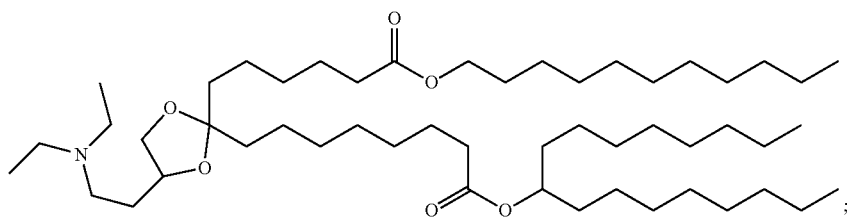 [SMILES: CCCCCCCCCCCOC(=O)CCCCCC1(CCCCCCCC(=O)OC(CCCCCCCC)CCCCCCCC)OCC(CCN(CC)CC)O1]

In a preferred embodiment, wherein the compound of formula (I) is Compound 12
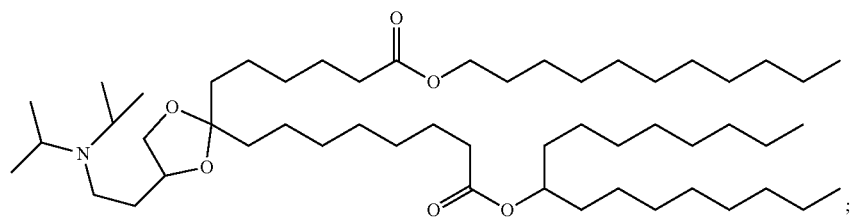 [SMILES: CCCCCCCCCCCOC(=O)CCCCCC1(CCCCCCCC(=O)OC(CCCCCCCC)CCCCCCCC)OCC(CCN(C(C)C)C(C)C)O1]
In a preferred embodiment, wherein the compound of formula (I) is Compound 13
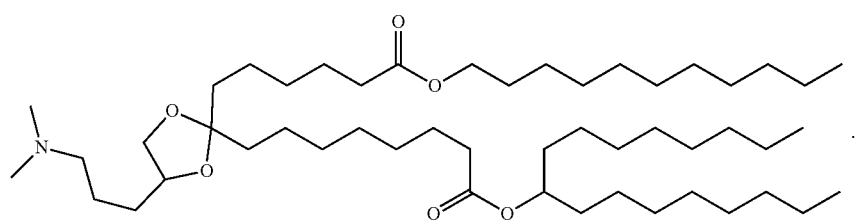 [SMILES: CCCCCCCCCCCOC(=O)CCCCCC1(CCCCCCCC(=O)OC(CCCCCCCC)CCCCCCCC)OCC(CCCN(C)C)O1]
The present application also relates to optical isomers of the compounds:
| Chiral isomers of Compound 2 |
|---|
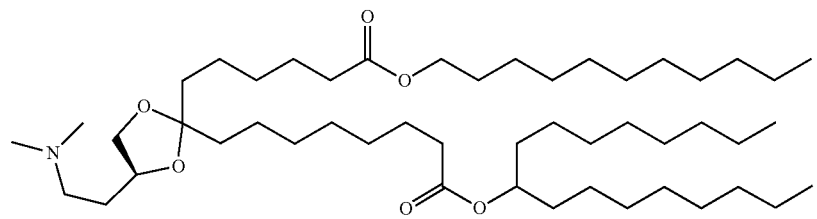
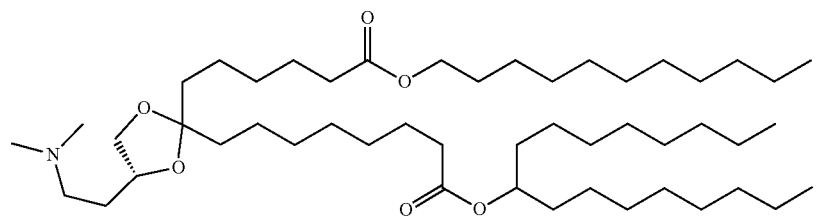
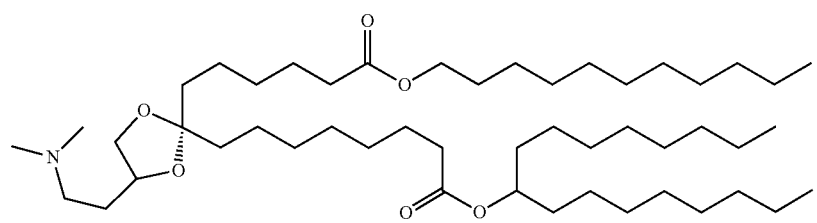

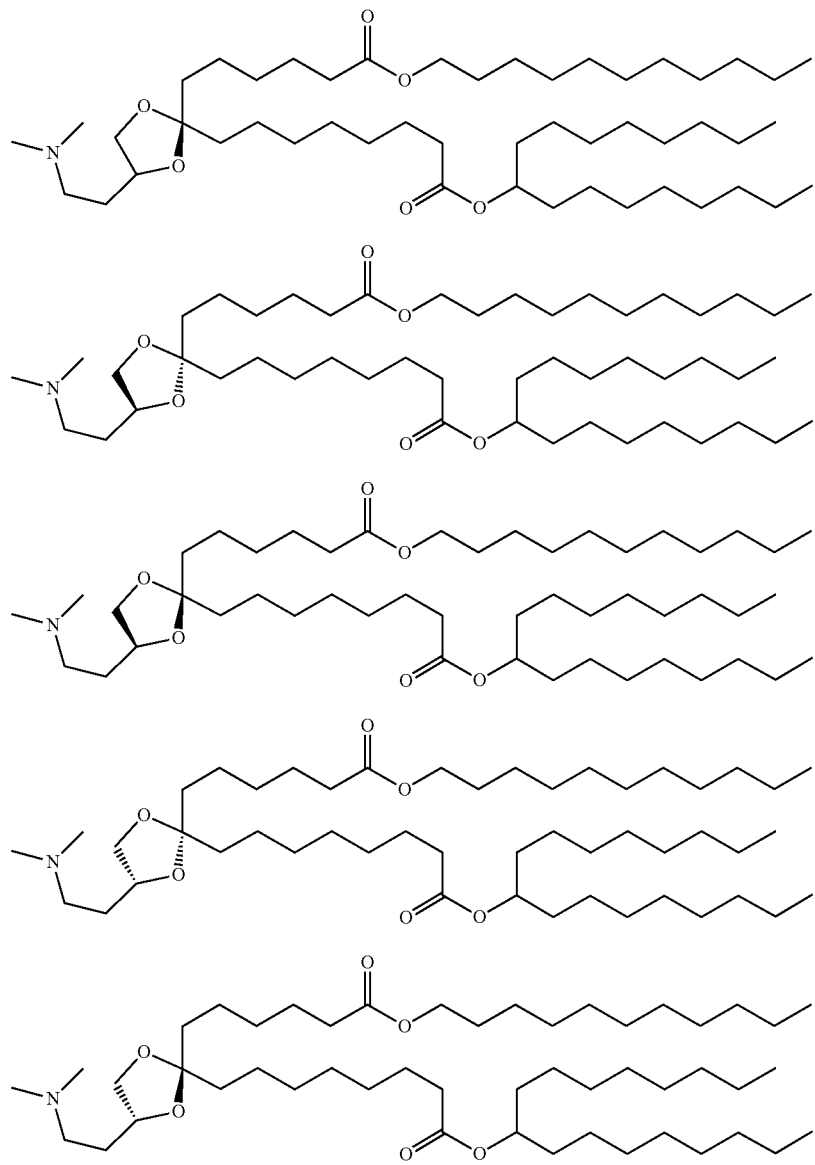
Chiral isomers of Compound 5
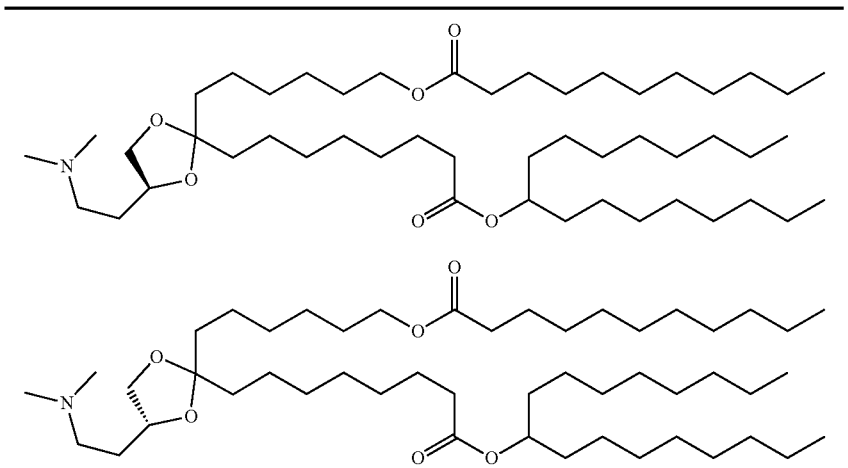

-continued
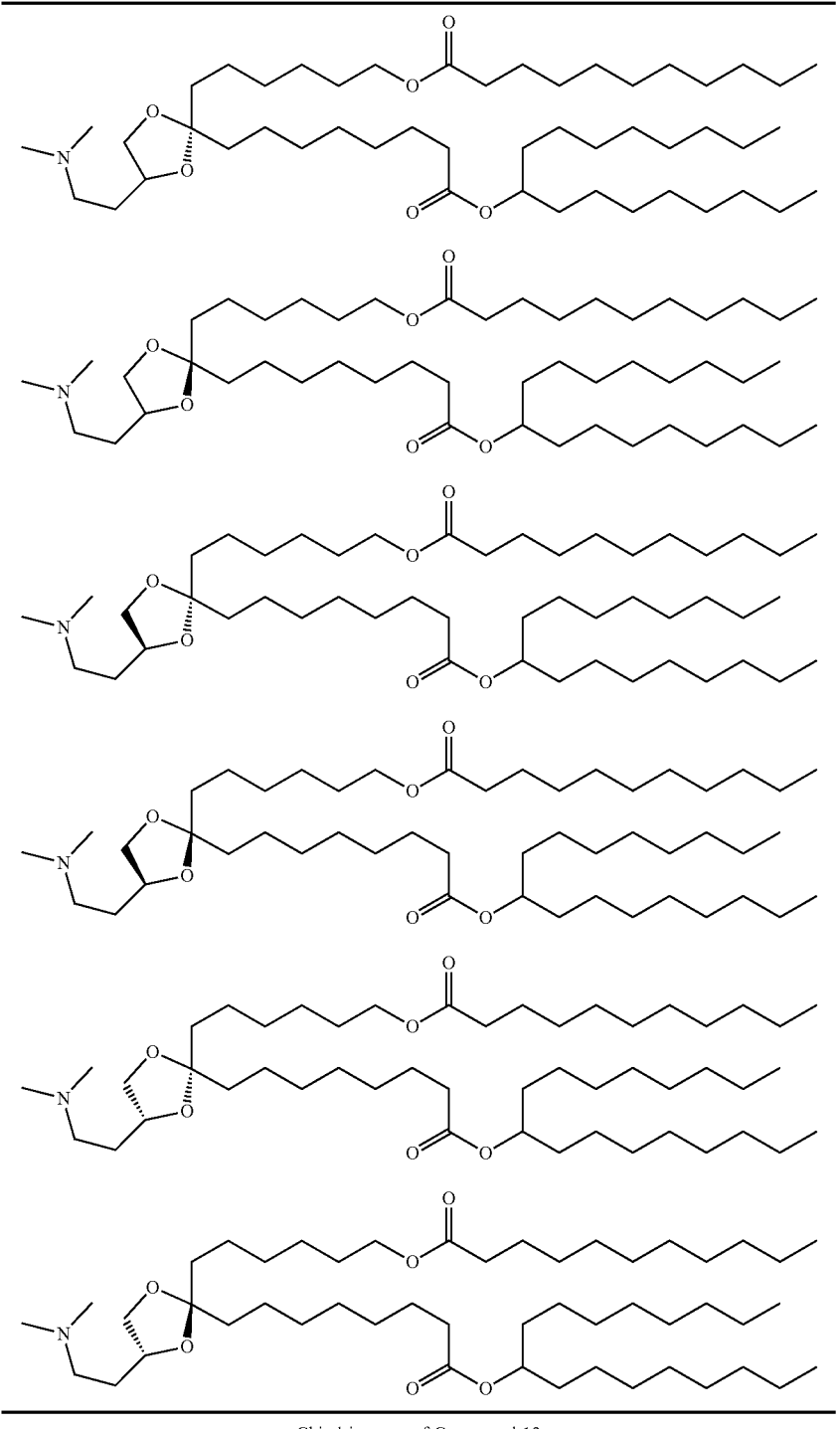
Chiral isomers of Compound 13
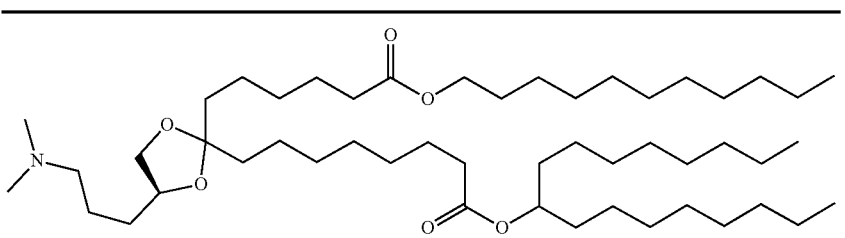

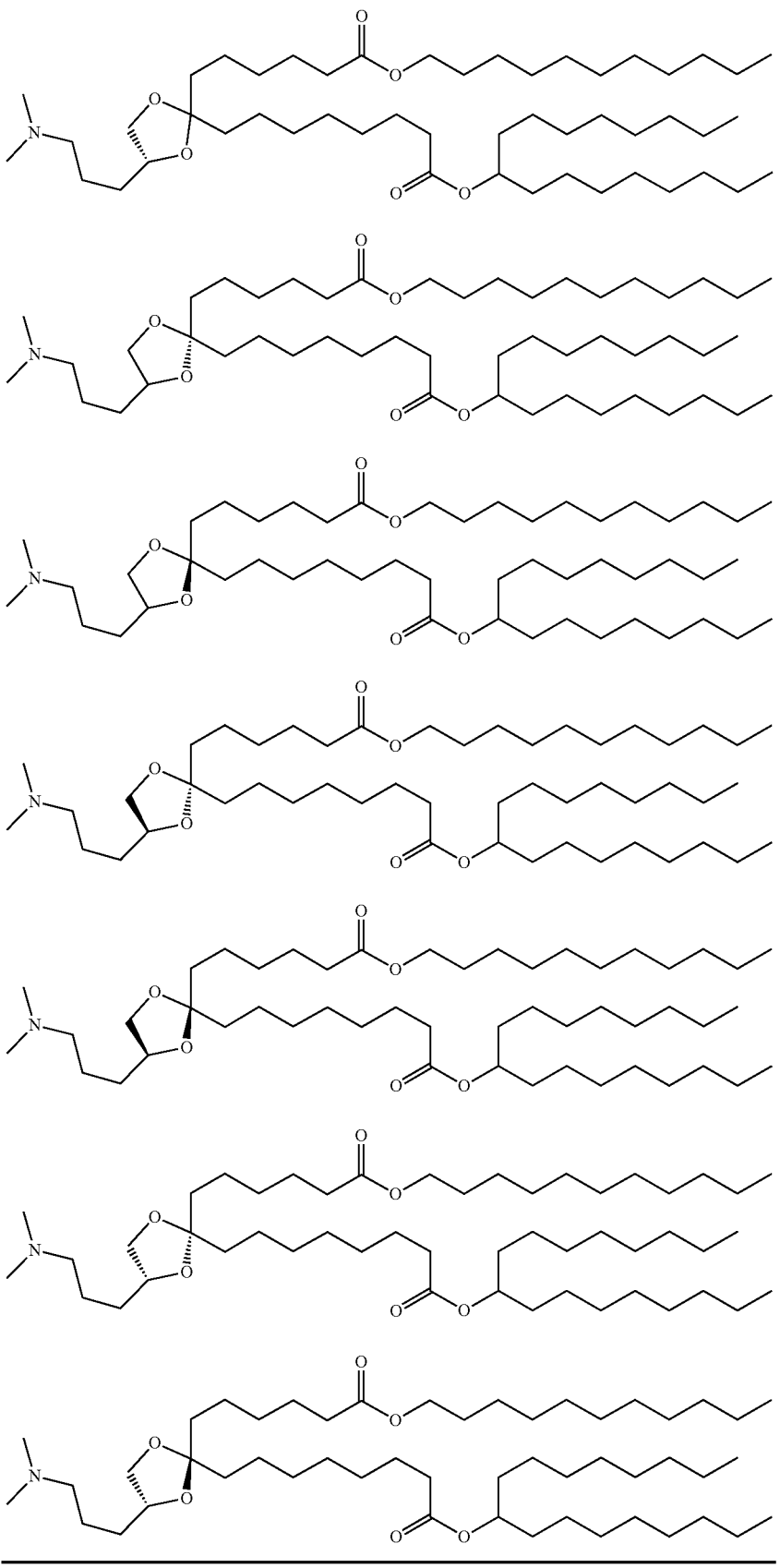

The present application further provides a method for compound (IA) comprising,

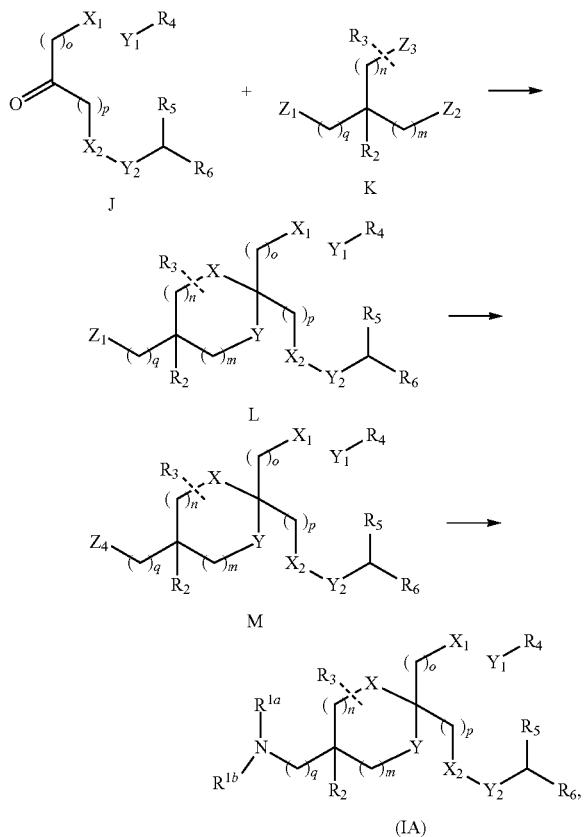

(IA)

wherein $Z_1$ is selected from OH, $Z_2$ and $Z_3$ are independently selected from OH or SH, respectively, and $Z_4$ is selected from OMs;

X and Y are independently selected from O or S;

$X_1$ and $X_2$ are independently selected from C=O or O, $Y_1$ and $Y_2$ are independently selected from C=O or O, with the proviso that $X_1$ and $Y_1$ are not both C=O or O, and $X_2$ and $Y_2$ are not both C=O or O;

$R^{1a}$, $R^{1b}$ are independently selected from H or C1-C6alkyl;

$R_2$, $R_3$ are independently selected from H or C1-C6alkyl;

$R_4$, $R_5$ and $R_6$ are independently selected from C1-C14alkyl;

m and n are independently selected from 0, 1 or 2, with the proviso that m and n are not both 0;

o and p are independently selected from 1, 2, 3, 4, 5, 6, 7, 8, 9 or 10;

q is selected from 0, 1, 2, 3, 4, 5 or 6;

wherein said Compound J is reacted with Compound K to form Compound L in a benzene-based solution of pyridinium 4-methylbenzenesulfonate (Tso-Py), a benzene-based solvent used in said benzene-based solution may be toluene, xylene, trimethylbenzene and tetramethylbenzene, etc., and in a preferred embodiment of the present application, said benzene-based solvent is toluene;

said Compound L is reacted in a halogenated alkane solution of $(CH_3SO_2)_2O$ to provide Compound M, wherein the halogenated alkane, abbreviated as haloalkane or alkyl halide, refers to an organic compound in which one or more hydrogen atoms in the alkane molecule are replaced by halogen atom (fluorine, chlorine, bromine, iodine), and said haloalkane of the present application is not limited, and in a preferred embodiment, the chlorinated alkane is preferably DCM, dichloroethane or chloroform;

the Compound M is reacted in a polar aprotic solvent to form Compound IA, the polar aprotic solvent may be dimethylsulfoxide (DMSO), acetone, acetonitrile, dimethylformamide, dimethylacetamide, hexamethylphosphoramide, tetrahydrofuran (THF), N,N-dimethylformamide (DMF), dimethylacetamide (DMA), preferably tetrahydrofuran (THF).

In the above synthesis method, the source of Compound J is not limited and may be commercially available or may be synthesized internally, and in a specific embodiment, Compound J is synthesized by the following synthesis method,

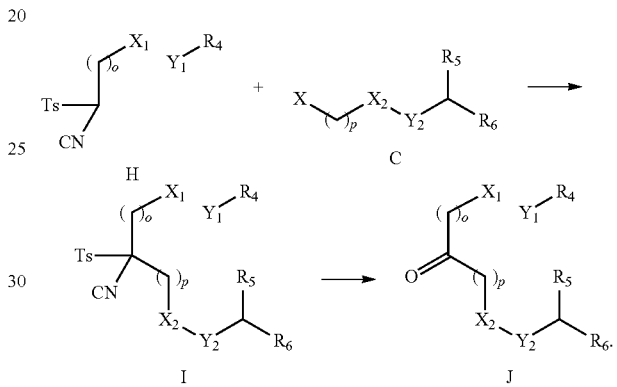

wherein $X_1$ and $X_2$ are independently selected from C=O or O, $Y_1$ and $Y_2$ are independently selected from C=O or O, with the proviso that $X_1$ and $Y_1$ are not both C=O or O, and $X_2$ and $Y_2$ are not both C=O or O;

X is selected from halogen;

$R_4$, $R_5$ and $R_6$ are independently selected from C1-C14alkyl;

o and p are independently selected from 1, 2, 3, 4, 5, 6, 7, 8, 9 or 10;

wherein said Compound H is reacted with Compound C in the presence of a carbonate salt, $NBu_4I$ and a polar aprotic solvent to produce Compound I (Ts represents p-toluenesulfonyl); in a preferred embodiment, the carbonate salt is an alkali metal carbonate, and preferably $Cs_2CO_3$ or $K_2CO_3$;

said polar aprotic solvent may be dimethyl sulfoxide (DMSO), acetone, acetonitrile, dimethylformamide, dimethylacetamide, hexamethylphosphoramide, tetrahydrofuran (THF), N,N-dimethylformamide (DMF), dimethylacetamide (DMA), and preferably DMF or DMA;

said Compound I is reacted at pH 1-5 to provide Compound J, preferably, the pH value is adjusted by hydrochloric acid solution, the concentration of the hydrochloric acid is preferably 12M, said reaction solvent is haloalkane, and preferably DCM, dichloroethane or chloroform.

In the above synthesis method, the source of Compound H is not limited and may be commercially available or may be synthesized internally, and in a specific embodiment, Compound H is synthesized by the following synthesis method,

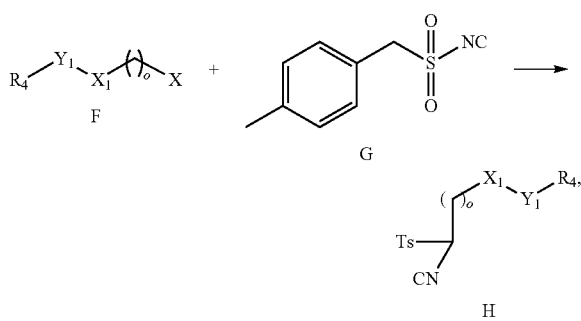

wherein $X_1$ and $Y_1$ are independently selected from C=O or O;

X is selected from halogen;

$R_4$ is selected from C1-C14alkyl;

o is selected from 1, 2, 3, 4, 5, 6, 7, 8, 9 or 10;

wherein said Compound F is reacted with Compound G in the presence of a carbonate salt, $NBu_4I$ and a polar aprotic solvent to provide Compound H; in a preferred embodiment, the carbonate salt is an alkali metal carbonate, and preferably $Cs_2CO_3$ or $K_2CO_3$;

said polar aprotic solvent may be dimethyl sulfoxide (DMSO), acetone, acetonitrile, dimethylformamide, dimethylacetamide, hexamethylphosphoramide, tetrahydrofuran (THF), N,N-dimethylformamide (DMF), dimethylacetamide (DMA), and preferably DMF or DMA.

The present application further provides a nanoparticle composition comprising a lipid component, which comprises the compound of formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11) as provided by the present application.

In some embodiments, said nanoparticle composition has an average particle size of 50 nm-110 nm, such as 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, 101 nm, 102 nm, 103 nm, 104 nm, 105 nm, 106 nm, 107 nm, 108 nm or 109 nm.

Said nanoparticle composition may include, for example, lipid nanoparticles (LNPs), liposomes, lipid vesicles and lipid complexes. In some embodiments, the nanoparticle composition is a vesicle comprising one or more lipid bilayers. In some embodiments, the nanoparticle composition comprises two or more concentric bilayers separated by two or more aqueous compartments. The lipid bilayers may be functionalized and/or cross-linked to each other. The lipid bilayer may include one or more ligands, proteins or channels.

The nanoparticle composition of the present application comprises a lipid component comprising at least one compound according to formula (I), (IA), (IIA), (IB), (IC) or (ID). For example, the lipid component of the nanoparticle composition may include one or more of compounds 1-32. The nanoparticle composition may also include a variety of other components. For example, in addition to a compound according to formula (I), (IA), (IIA), (IB), (IC) or (ID), the lipid component of the nanoparticle composition may also include one or more other lipids.

The lipid component of the nanoparticle composition may include one or more PEG lipids or PEG-modified lipids. Such materials may alternatively be referred to as pegylated lipids. PEG lipids are lipids modified with polyethylene glycol. The PEG lipid may be selected from a non-limiting group consisting of PEG-modified phosphatidylethanolamine, PEG-modified phosphatidic acid, PEG-modified ceramide, PEG-modified dialkylamine, PEG-modified diacylglycerol, PEG-modified dialkylglycerol, and mixtures thereof. For example, the PEG lipid may be PEG-c-DOMG, PEG-DMG, PEG-DLPE, PEG-DMPE, PEG-DPPC or PEG-DSPE lipid.

The lipid component of said nanoparticle composition may comprise one or more structural lipids. The structural lipid may be selected from, but not limited to cholesterol, coprosterol, sitosterol, ergosterol, stigmasterol, and mixtures thereof. In some embodiments, the structural lipid is cholesterol. In some embodiments, the structural lipid comprises cholesterol and corticosteroid (e.g., prednisolone, dexamethasone, prednisone, and hydrocortisone), or a combination thereof.

The lipid component of said nanoparticle compositions may comprise one or more phospholipids, and the phospholipids used in said nanoparticle compositions and methods may be selected from Dilauroyl lecithin (DLPC),
Dimyristoyl phosphatidylcholine (DMPC),
Dioleoyl lecithin (DOPC),
Dipalmitoyl phosphatidylcholine (DPPC),
Distearoyl phosphatidylcholine (DSPC),
Dioleoyl phosphatidylcholine (DUPC),
Palmitoyl oleoyl phosphatidylcholine (POPC),
1,2-Di-O-octadecyl-sn-glycero-3-phosphocholine (18:0 Diether PC),
1-Oleoyl-2-cholesteryldimethylsuccinoyl-sn-glycero-3-phosphocholine (OChemsPC),
1-Hexadecyl-sn-glycero-3-phosphocholine (C16 Lyso PC),
1,2-Divinyl-sn-glycero-3-phosphocholine,
1,2-Diarylacyl-sn-glycero-3-phosphocholine,
1,2-Dioleoyl-sn-glycero-3phosphorylethanolamine (DOPE),
1,2-Di-phytanoyl-sn-glycero-3-phosphoethanolamine (ME 16.0 PE),
1,2-Distearoyl-sn-glycero-3-phosphoethanolamine,
1,2-Diethenol-sn-glycero-3-phosphoethanolamine,
1,2-Divinyl-sn-glycero-3-phosphoethanolamine,
1,2-Diaryl-sn-glycero-3-phosphoethanolamine,
1,2-Dithiohexaenoate-sn-glycero-3-phosphoethanolamine,
1,2-dioleoyl-sn-glycero-3-phosphate-(1-glycerol) sodium salt (DOPG) or sphingomyelin.

In some embodiments, the nanoparticle composition comprises DSPC. In some embodiments, the nanoparticle composition comprises DOPE. In some embodiments, the nanoparticle composition comprises DSPC and DOPE.

In some embodiments, a nanoparticle composition comprising one or more lipids described herein may further comprise one or more adjuvants, for example, glucopyranosyl lipid adjuvant (GLA), CpG oligodeoxynucleotides (e.g., class A or class B), poly(I:C), aluminum hydroxide, and Pam3CSK 4.

The nanoparticle compositions may comprise one or more therapeutic and/or prophylactic agents.

The present application provides methods of delivering a therapeutic and/or prophylactic agent to a mammalian cell or organ, producing a polypeptide of interest in the mammalian cell, and treating a disease or disorder in a mammal in need thereof, comprising administering to the mammal and/or contacting the mammalian cell with the composition comprising therapeutic and or prophylactic nanoparticles.

The therapeutic and/or prophylactic agent includes a biologically active substance, and may alternatively be referred to as an "active agent". The therapeutic and/or prophylactic agent may be a substance that, once delivered to a cell or organ, produces a desired change in the cell, organ or other body tissue or system. Such substance may be used to treat one or more diseases, disorders or conditions. In some embodiments, the therapeutic and/or prophylactic agent is a small molecule drug that may be used to treat a particular disease, disorder, or condition. Examples of a drug that may be used in the nanoparticle composition include, but are not limited to, antineoplastic agents (e.g., vincristine, adriamycin, mitoxantrone, camptothecin, cisplatin, bleomycin, cyclophosphamide, methotrexate, and streptozotocin), antineoplastic agents (e.g., actinomycin D, vincristine), vinblastine, arabinoside cystine, anthracyclines, alkylating agents, platinum compounds, antimetabolites and nucleoside analogs (e.g., methotrexate, purine, and pyrimidine analogs), anti-infective agents, local anesthetics (e.g., dibucaine and chlorpromazine), beta-adrenergic blockers (e.g., propranolol, timolol, and labetalol), antihypertensive agents (e.g., clonidine and hydralazine), antidepressants (e.g., imipramine, amitriptyline, and doxepin), anti-conversion agents (e.g., phenytoin), antihistamines (e.g., diphenhydramine, chlorphenamine and promethazine), antibiotics/antibacterials (e.g., gentamicin, ciprofloxacin and cefoxitin), antifungals (e.g., miconazole, terconazole, econazole, isoconazole, butoconazole, clotrimazole, itraconazole, nystatin and naftifine), antiparasitics, hormones, hormone antagonists, immunomodulators, neurotransmitter antagonists, antiglaucoma agents, vitamins, anesthetics and imaging agents.

In some embodiments, the therapeutic and/or prophylactic agent is a cytotoxin, a radioactive ion, a chemotherapeutic agent, a vaccine, a compound that elicits an immune response, and/or another therapeutic and/or prophylactic agent. The cytotoxin or cytotoxic agent includes any agent that may be harmful to a cell. Examples include, but are not limited to, paclitaxel, cytochalasin B, gramicidin D, ethidium bromide, emetine, mitomycin, etoposide, teniposide, vincristine, vinblastine, colchicine, adriamycin, daunorubicin, dihydroxyanthraquinone, synmethasone, 1-nortestosterone, *Aspergillus oryzae*, glucocorticoids, procaine, tetracaine, lidocaine, propranolol, puromycin, maytansinoids, e.g., maytansinol, rachelmycin (CC-1065), and analogs or homologs thereof. Radioactive ions include, but are not limited to, iodine (e.g., iodine 125 or iodine 131), strontium 89, phosphorus, palladium, cesium, iridium, phosphate, cobalt, yttrium 90, and sa 153. Vaccines include compounds and formulations capable of providing immunity to one or more conditions associated with infectious diseases (e.g., influenza, measles, Human Papilloma Virus (HPV), rabies, meningitis, pertussis, tetanus, plague, hepatitis and tuberculosis), including mRNA encoding infectious disease-derived antigens and/or epitopes. Vaccines also include compounds and preparations that direct an immune response against cancer cells, and may include mRNA encoding tumor cell-derived antigens, epitopes, and/or neoepitopes. Compounds that elicit an immune response may include vaccines, corticosteroids (e.g., dexamethasone), and other species.

Other therapeutic and/or prophylactic agents include, but are not limited to, antimetabolites (e.g., methotrexate, 6-mercaptopurine, 6-thioguanine, cytarabine, 5-fluorouracil decarboxylase), alkylating agents (e.g., methyclothiazide, thiotepa-chloramphenicol, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin and anthramycin (AMC)), and antimitotic agents (e.g., vincristine, vinblastine, paclitaxel, and zeatin glycosides)

In some embodiments, the vaccine and/or compound capable of eliciting an immune response is administered intramuscularly in a composition comprising a compound of formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), e.g., one or more of compounds 1-32. Other therapeutic and/or prophylactic measures include, but are not limited to, antimetabolites (e.g., methotrexate, 6-mercaptopurine, 6-thioguanine, cytarabine, 5-fluorouracil, decarbazine), alkylating agents (e.g., methoxyethylamine, metsulfovax, chlorobutyric acid, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and adriamycin), antibiotics (e.g., actinomycin, mithramycin, adriamycin, actinomycin), anthramycin (AMC)) and antimitotics (e.g., vincristine, vinblastine, paclitaxel, and maytansinoids).

In other embodiments, the therapeutic and/or prophylactic agent is a protein. Therapeutic proteins that may be used in the nanoparticle compositions described in the present application include, but are not limited to, gentamicin, amikacin, insulin, erythropoietin (EPO), granulocyte colony-stimulating factor (G-CSF), granulocyte-macrophage colony-stimulating factor (GM-CSF), factor VIR, luteinizing hormone-releasing hormone (LHRH)-analogs, interferon, eparin, hepatitis b surface antigen, typhoid vaccine and cholera vaccine.

In some embodiments, the therapeutic agent is a polynucleotide or nucleic acid (e.g., ribonucleic acid or deoxyribonucleic acid). The term "polynucleotide" in its broadest sense includes any compound and/or substance that is bound or may be bound to an oligonucleotide chain. Exemplary polynucleotides for use according to the present invention include, but are not limited to, one or more of deoxyribonucleic acid (DNA), ribonucleic acid (RNA) including messenger mRNA (mRNA), hybrids thereof, RNAi-inducing agents, RN-Ai agents, siRNA, shRNA, miRNA, antisense RNA, ribozymes, catalytic DNA, RNA that induces triple helix formation, aptamers, vectors, and the like. In some embodiments, the therapeutic and/or prophylactic agent is RNA. RNA that may be used in the compositions and methods described herein may be selected from, but is not limited to, shortmers, anti-gametophytes, antisense, ribozymes, small interfering RNA (siRNA), asymmetric interfering RNA (aiRNA), microRNA (miRNA), double-stranded RNA (dsRNA), small hairpin RNA (shRNA), transfer RNA (tRNA), messenger RNA (mRNA), and mixtures thereof. In certain embodiments, the RNA is mRNA.

In certain embodiments, the therapeutic and/or prophylactic agent is mRNA. The mRNA may encode any polypeptide of interest, including any naturally or non-naturally occurring or otherwise modified polypeptide. The polypeptide encoded by the mRNA may be of any size and may have any secondary structure or activity. In some embodiments, the polypeptide encoded by the mRNA may have a therapeutic effect when expressed in a cell.

In other embodiments, the therapeutic and/or prophylactic agent is siRNA. The siRNA may be capable of selectively knocking down or downregulating the expression of the gene of interest. For example, a siRNA may be selected to silence a gene associated with a particular disease, disorder, or condition when a nanoparticle composition including the siRNA is administered to a subject in need thereof. The siRNA may comprise a sequence complementary to an mRNA sequence encoding a gene or protein of interest. In some embodiments, the siRNA may be an immunomodulatory siRNA.

In some embodiments, the therapeutic and/or prophylactic agent is an shRNA or a vector or plasmid encoding the shRNA. Upon delivery of the appropriate construct to the nucleus, the shRNA may be produced inside the target cell. Constructs and mechanisms associated with shRNA are well known in the relevant art.

The nanoparticle compositions of the present application may comprise one or more components in addition to those described above. For example, said nanoparticle compositions may comprise one or more small hydrophobic molecules, such as vitamins (e.g., vitamin A or vitamin E) or sterols.

The nanoparticle compositions may also comprise one or more permeability enhancer molecules, carbohydrates, polymers, surface modifiers or other components. Said permeability enhancer molecule may be a molecule described in U.S. Patent Application 2005/0222064. Said carbohydrates may include monosaccharides (e.g., glucose) and polysaccharides (e.g., glycogen and its derivatives and analogs).

Said nanoparticle composition may further comprise one or more polymers, which may be biodegradable and/or biocompatible. Said polymers may be selected from, but are not limited to, polyamines, polyethers, polyamides, polyesters, polyurethanes, polyurea, polycarbonates, polystyrene, polyimides, polysulfones, polyurethanes, polyacetylene, polyethylene, polyethyleneimine, polyisocyanates, polyacrylates, polymethacrylates, polyacrylonitrile, and polyarylesters. For example, the polymer may include polycaprolactone (PCL), ethylene vinyl acetate polymer (EVA), polylactic acid (PLA), poly L-lactic acid (PLLA), polyglycolic acid (PGA), poly(lactic-co-glycolic acid) (PLGA), poly(L-lactic-co-glycolic acid) (PLLGA), poly(D,L-lactide) (PDLA), poly(L-lactide (PLLA), poly(D,L-lactide-co-caprolactone), poly(D,L-lactide-caprolactone-glycolide), poly(D,L-lactide-PEO-co-D,L-lactide), poly(D,L-lactide-co-PPO-co-D,L-lactide), polyalkylcyanoacrylate, polyurethane, poly-L-lysine (PLL), hydroxypropyl methacrylate (HPMA), polyethylene glycol, poly-L-glutamic acid, polyhydroxy acids, polyanhydrides, polyorthoesters, poly(ester amides), polyamides, poly(ester ethers), polycarbonates, polyalkylenes such as polyethylene and polypropylene; polyalkylene glycols such as poly(ethylene glycol) (PEG); polyalkylene oxide (PEO); polyalkylene terephthalates, such as polyethylene glycol terephthalate; polyvinyl alcohol (PVA); polyvinyl ethers, polyvinyl esters, such as poly(vinyl acetate), polyvinyl halides, such as polyvinyl chloride (PVC), polyvinylpyrrolidone (PVP), polysiloxanes, polystyrene (PS), polyurethanes, derivatized celluloses, such as alkylcelluloses, hydroxyalkylcelluloses, cellulose ethers, cellulose esters, nitrocellulose, hydroxypropylcellulose, carboxymethylcellulose, acrylic polymers, such as poly(methyl methacrylate) (PMMA), poly(ethyl methacrylate), poly (butyl methacrylate), poly(isobutyl methacrylate), poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) and copolymers and mixtures thereof, polydioxanone and copolymers thereof, polyhydroxyalkanoates, polypropylene fumarate, polyoxymethylene, poloxamers, polyethylene diamine, poly(orthoesters), poly(butyric acid), poly(valeric acid), poly(lactide-caprolactone), trimethylene carbonate, poly(N-acryloylmorpholine) (PAcM), poly(2-methyl-2-oxazoline (PMOX), poly(2-ethyl-2-oxazoline) (PEOZ) and polyglycerol.

The nanoparticle composition may further comprise one or more surface modifying agents, which may include, but are not limited to, anionic proteins (e.g., bovine serum albumin), surfactants (e.g., cationic surfactants such as cationic surfactants such as dimethyl octacosyl-ammonium bromide), sugars or sugar derivatives (e.g., cyclodextrins), nucleic acids, polymers (e.g., heparin, polyethylene glycol, and poloxamers), mucolytics (e.g., acetylcysteine, mugwort, bromelain, papain, turfgrass, caprolactone bromide, carbocisteine, eprinodone, mesna, ambroxol, sobrerol, domiodol, letosteine, stepronin, tiopronin, gelsolin, nucleosin β4, dornase alfa, neltenexine and erdosteine) and DNase (e.g. rhDNase). Surface modifiers may be set within the nanoparticles and/or on the surface of the nanoparticle composition (e.g., by coating, adsorption, covalent bonding, or other methods).

The nanoparticle composition may further comprise one or more functionalized lipids. For example, a lipid may be functionalized with an alkynyl group which may undergo a cycloaddition reaction when exposed to an azide under appropriate reaction conditions. In particular, the lipid bilayer may be functionalized in this way with one or more groups for facilitating membrane penetration, cell recognition or imaging. The surface of the nanoparticle composition may also be conjugated with one or more useful antibodies. Functional groups and conjugates useful for targeted cell delivery, imaging and membrane penetration are well known in the art.

In addition to the components described above, the nanoparticle composition may include any substance useful in pharmaceutical compositions. For example, the nanoparticle composition may comprise one or more pharmaceutically acceptable excipients or auxiliary ingredients such as, but are not limited to, one or more solvents, dispersion media, diluents, dispersion aids, suspending agents, granulation aids, disintegrants, fillers, glidants, liquid carriers, binders, surfactants, isotonicity agents, thickening or emulsifying agents, buffers, lubricants, oils, preservatives and other materials. Excipients, such as waxes, butters, colorants, coatings, flavors, and flavorants, may also be included. Pharmaceutically acceptable excipients are well known in the art.

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn starch, sugar powder, and/or combinations thereof. The granulating and dispersing agents may be selected from potato starch, corn starch, tapioca starch, sodium starch glycolate, clays, alginic acid, guar gum, citrus pulp, agar, bentonite, cellulose and wood products, cation exchange resins, calcium carbonate, silicates, sodium carbonate, cross-linked poly (vinyl-pyrrolidone), sodium carboxymethyl starch (sodium starch glycolate), carboxymethyl cellulose, cross-linked sodium carboxymethyl cellulose (croscarmellose), methyl cellulose, pregelatinized starch (starch 1500), microcrystalline starch, water-insoluble starch, calcium carboxymethyl cellulose, aluminum magnesium silicate, sodium lauryl sulfate, quaternary ammonium compounds and/or combinations thereof.

Surfactants and/or emulsifiers may include, but are not limited to, natural emulsifiers (e.g., acacia, agar, alginic acid, sodium alginate, chondroitin, cholesterol, xanthan gum, pectin, gelatin, egg yolk, casein, lanolin, cholesterol, waxes, and lecithin), colloidal clays (e.g., bentonite [aluminum silicate] and VEEGUM® [aluminum magnesium silicate]), long chain amino acid derivatives, high molecular weight alcohols (e.g., stearyl alcohol, cetyl alcohol, oleyl alcohol), triacetin monostearate, ethylene glycol distearate, glycerol monostearate and propylene glycol monostearate, polyvinyl alcohol), carbomers (e.g., carboxypolymethylene, polyacrylic acid, acrylic acid polymers and carboxyvinyl polymers), carrageenan, cellulose derivatives (e.g., sodium carboxymethylcellulose, powdered cellulose, hydroxymethyl cellulose, hydroxypropyl cellulose, hydroxypropyl methyl cellulose, methylcellulose), a sorbitan fatty acid ester (e.g., polyoxyethylene sorbitan monolaurate [TWEEN®20], polyoxyethylene sorbitan [TWEEN®60], polyoxyethylene sorbitan monooleate [TWEEN®80], Sorbitan monopalmitate [SPAN®40], sorbitan monostearate [SPAN®60], sorbitan tristearate [SPAN®65], glycerol monooleate, sorbitan monooleate [SPAN®80], polyoxyethylene esters (e.g. polyoxyethylene monostearate [MYRJ®45], polyoxyethylene hydrogenated castor oil, polyethoxylated castor oil, polyoxymethylene stearate and SOLUTOL®], sucrose fatty acid esters, polyethylene glycol fatty acid esters (e.g. CREMOPHOR®), polyoxyethylene ethers (e.g. polyoxyethylene lauryl ether [BRIJ®30]), poly(vinyl-pyrrolidone), diethylene glycol monolaurate, triethanolamine oleate, sodium oleate, potassium oleate, ethyl oleate, oleic acid, ethyl laurate, sodium dodecyl sulfate, PLURONIC® F68, POLOXAMER®188, cetrimonium bromide, cetyl pyridinium chloride, benzalkonium chloride, docusate sodium, and/or combinations thereof.

Binders may be starches (e.g. corn starch and starch paste), gelatin, sugars (e.g. sucrose, glucose, dextrose, dextrin, molasses, lactose, lactitol, mannitol), natural and synthetic gums (e.g. acacia, sodium alginate, Irish moss extract, panwar gum, ghatti gum, mucilages of Isabel hulls, carboxymethyl cellulose, methyl cellulose, ethyl cellulose, hydroxyethyl cellulose, hydroxypropyl cellulose, hydroxypropyl methyl cellulose, microcrystalline cellulose, cellulose acetate, poly (vinyl pyrrolidone), magnesium aluminium silicate (VEEGUM®) and larch arabinogalactan), alginates, polyethylene oxide, polyethylene glycol, inorganic calcium salts; silicic acid, polymethacrylate, wax, water, alcohols, combinations thereof or any other suitable binder.

Examples of preservatives may include, but are not limited to, antioxidants, chelating agents, antimicrobial preservatives, antifungal preservatives, alcoholic preservatives, acidic preservatives, and/or other preservatives. Examples of antioxidants include, but are not limited to, alpha-tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid and/or trisodium edetate. Examples of antimicrobial preservatives include, but are not limited to, benzalkonium chloride, benzethonium chloride, benzyl alcohol, bromophenol, cetrimide, cetyl pyridinium chloride, chlorhexidine, chlorobutanol, chlorocresol, chloroxylenol, cresol, ethanol, glycerol, hexyloxybutanol, imidurea, phenethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcoholic preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deoxyoxime mesylate, cetrimide, Butyl Hydroxyanisole (BHA), Butyl Hydroxytoluene (BHT), ethylenediamine, Sodium Lauryl Sulfate (SLS), Sodium Lauryl Ether Sulfate (SLES), sodium bisulfite, sodium metabisulfite, potassium sulfite, potassium metabisulfite, GLYDANTPLUS®, PHENONIP®, methyl p-hydroxybenzoate, GERMALL®115, GERMABEN® II, NEOLONE™ KATHON™ and/or EUXYL®.

Examples of buffering agents include, but are not limited to, citrate buffer solution, acetate buffer solution, phosphate buffer solution, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propionic acid, calcium levulinate, pentanoic acid, dibasic calcium phosphate, phosphoric acid, tricalcium phosphate, calcium hydrogen phosphate, potassium acetate, potassium chloride, potassium gluconate, potassium mixtures, dipotassium hydrogen phosphate, potassium dihydrogen phosphate, potassium phosphate mixtures, sodium acetate, sodium bicarbonate, sodium chloride, sodium citrate, sodium lactate, disodium hydrogen phosphate, sodium dihydrogen phosphate, sodium phosphate mixtures, tromethamine, sulfamate buffers, magnesium hydroxide, aluminum hydroxide, alginic acid, pyrogen-free water, isotonic saline, Ringer's solution, ethanol, and/or combinations thereof. The lubricant is selected from magnesium stearate, calcium stearate, stearic acid, silicon dioxide, talc, malt, hydrogenated vegetable oil, polyethylene glycol, sodium benzoate, sodium acetate, sodium chloride, leucine, and magnesium laurate, sulfates, sodium lauryl sulfate, and combinations thereof.

Examples of oils include, but are not limited to, almond, apricot kernel, avocado, babassu, bergamot, black currant seed, borage, chamomile, canola, caraway, carnauba, castor, cinnamon, cocoa butter, coconut, cod liver, coffee, corn, cottonseed, eucalyptus, evening primrose, fish, linseed, geraniol, gourd, grape seed, hazelnut, hyssop, isopropyl myristate, jojoba oil, lavender, lavandin, lemon, macadamia nut, mallow, mango seed, mink skin, nutmeg, olive, orange, palm, palm kernel, peach kernel, peanut, poppy seed, pumpkin seed, rapeseed, rice bran, rosemary, safflower, sandalwood, essence, sea buckthorn, sesame, shea butter, silicone, soybean, sunflower, tea tree, thistle, *Ailanthus altissima*, vetiver, walnut and wheat germ oil and butyl stearate, caprylic triglyceride, capric triglyceride, cyclomethicone, diethyl sebacate, dimethicone, isopropyl myristate, mineral oil, octyldodecanol, oleyl alcohol, silicone oil and/or combinations thereof.

The nanoparticle composition as described in the present application may comprise a lipid component and one or more other components, such as a therapeutic and/or prophylactic agent. The nanoparticle composition may be designed for one or more particular use or target. The elements of the nanoparticle compositions may be selected based on a particular use or target and/or based on efficacy, toxicity, cost, ease of use, availability, or other characteristics of one or more elements. Similarly, the particular formulation of the nanoparticle composition may be selected for a particular use or target based on, for example, the efficacy and toxicity of a particular combination of elements.

The lipid component of said nanoparticle composition may comprises, for example, the compound according to formula (I), (IA), (IA-1), (IA-2), (IA-3), (IA-4), (IA-5), (IA-6), (IIA), (IIA-A), (IIA-B), (IIA-C), (IIA-D), (IIA-E), (IIA-F), (IIA-G), (IIA-H), (IB), (IB-1), (IB-2), (IB-3), (IB-4), (IB-5), (IB-6), (IC), (IC-1), (IC-2), (IC-3), (IC-4), (IC-5), (IC-6), (IC-7), (IC-8), (IC-9), (IC-10), (IC-11), (ID), (ID-1), (ID-2), (ID-3), (ID-4), (ID-5), (ID-6), (ID-7), (ID-8), (ID-9), (ID-10), (ID-11), a phospholipid (for example unsaturated lipids, such as DOPE or DSPC), a PEG lipid and a structural lipid.

The nanoparticle compositions may be designed for one or more specific uses or targets. For example, nanoparticle compositions may be designed for delivering a therapeutic and/or prophylactic agent, such as RNA, to a particular cell, tissue, organ or system or group thereof within a mammalian body. The physicochemical properties of the nanoparticle composition may be altered to increase selectivity for specific body targets. For example, the particle size may be adjusted based on the window size of different organs. The therapeutic and/or prophylactic agents included in the nanoparticle compositions may also be selected based on the desired one or more delivery targets. For example, a therapeutic and/or prophylactic agent may be selected for a particular indication, condition, disease or disorder and/or delivery (e.g., local or specific delivery) to a particular cell, tissue, organ or system or group thereof. In certain embodiments, the nanoparticle composition may include mRNA encoding a polypeptide of interest that may be translated within a cell to produce the polypeptide of interest. Such compositions may be designed for specific delivery to a particular organ. In some embodiments, the composition may be designed to specifically deliver to the liver of a mammal.

The amount of therapeutic and/or prophylactic agent in the nanoparticle composition may depend on: the size, composition of the nanoparticle composition, desired target and/or application or other properties, and the nature of the therapeutic and/or prophylactic agent; for example, the amount of RNA that may be used in the nanoparticle composition may depend on the size, sequence and other characteristics of the RNA. The relative amounts of therapeutic and/or prophylactic agent and other elements (e.g., lipids) in the nanoparticle compositions may also vary.

The properties of the nanoparticle composition may depend on its components. For example, a nanoparticle composition comprising cholesterol as a structural lipid may have different properties from a nanoparticle composition comprising a different structural lipid. Similarly, the properties of the nanoparticle composition may depend on the absolute or relative amounts of its components. For example, a nanoparticle composition comprising a phospholipid with relatively high mole fraction may have different properties from a nanoparticle composition comprising a phospholipid with relatively low mole fraction. The properties may also vary depending on the method and conditions of preparation of the nanoparticle composition.

The nanoparticle compositions may be characterized by a variety of methods. For example, a microscope (e.g., transmission electron microscope or scanning electron microscope) may be used to examine the morphology and size distribution of the nanoparticle composition. Dynamic light scattering or potentiometry (e.g., potentiometric titration) may be used to measure zeta potential. Dynamic light scattering may also be used to determine particle size.

The nanoparticle composition has an average particle size of 50 nm to 110 nm.

The nanoparticle composition may be relatively homogeneous. The polydispersity index may be used to indicate the homogeneity of the nanoparticle composition, e.g., the particle size distribution of the nanoparticle composition. A small (e.g., less than 0.3) polydispersity index generally indicates a narrow particle size distribution. The nanoparticle composition has a polydispersity index of 0.04 to 0.20. For example, it may be 0.05, 0.06, 0.07, 0.08, 0.09, 0.10, 0.11, 0.12, 0.13, 0.14, 0.15, 0.16, 0.17, 0.18 or 0.19.

The encapsulation efficiency of a therapeutic and/or prophylactic agent describes the amount of the therapeutic and/or prophylactic agent that is encapsulated or otherwise associated with the nanoparticle composition after preparation, relative to the initial amount provided. The encapsulation efficiency is expected to be as high as possible (e.g., close to 100%). Encapsulation efficiency may be measured, for example, by comparing the amount of the therapeutic and/or prophylactic agent in a solution containing the nanoparticle composition before and after the nanoparticle composition is decomposed with one or more organic solvents or detergents. Fluorescence may be used to measure the amount of the free therapeutic and/or prophylactic agent (e.g., RNA) in a solution. For the nanoparticle compositions described herein, the encapsulation efficiency of a therapeutic and/or prophylactic agent may be at least 50%, e.g., 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

The nanoparticle composition may optionally comprise one or more coatings. For example, the nanoparticle composition may be formulated into capsules, films or tablets with coating. Capsules, films, or tablets containing the compositions described herein may be of any useful size, tensile strength, hardness, or density.

The nanoparticle compositions of the present application may be formulated in whole or in part as pharmaceutical compositions. The pharmaceutical composition may comprise one or more nanoparticle components. For example, the pharmaceutical composition may include one or more nanoparticle compositions comprising one or more different therapeutic and/or prophylactic agents. The pharmaceutical composition may further comprise one or more pharmaceutically acceptable excipients or auxiliary ingredients, such as those described herein, unless any conventional excipient or auxiliary ingredient may be incompatible with one or more components of the nanoparticle composition. If the excipient or adjunct ingredient is not compatible with a component of the nanoparticle composition, its combination with that component may result in any undesirable biological or other deleterious effects.

In some embodiments, the one or more excipients or auxiliary ingredients may constitute greater than 50% of the total mass or volume of the pharmaceutical composition comprising the nanoparticle composition. For example, one or more excipients or auxiliary ingredients may constitute 50%, 60%, 70%, 80%, 90% or more of the pharmaceutically customary. In some embodiments, the pharmaceutically acceptable excipient is at least 95%, at least 96%, at least 97%, at least 98%, at least 99%, or 100% pure. In some embodiments, the excipient is approved for human and veterinary use.

The relative amounts of one or more nanoparticle compositions, one or more pharmaceutically acceptable excipients and/or any other ingredients in the pharmaceutical compositions according to the present application will vary depending on the identity, size and/or disease condition of the subject to be treated, and further depending on the administration route of the composition. By way of example, the pharmaceutical composition may comprise one or more nanoparticle compositions ranging from 0.1% to 100% (wt/wt).

The nanoparticle compositions and/or the pharmaceutical compositions comprising one or more of said nanoparticle compositions may be administered to any patient or subject, including those who may benefit from a therapeutic effect provided by delivering the therapeutic and/or prophylactic agent to one or more specific cells, tissues, organs, or systems or groups thereof (e.g., the renal system). Although the descriptions of nanoparticle compositions and pharmaceutical compositions comprising nanoparticle compositions provided herein are primarily directed to compositions suitable for administration to a human, it will be understood by those skilled in the art that such compositions are generally suitable for administration to any other mammal. Modifications to compositions suitable for administration to humans are well known in order to make the compositions suitable for administration to various animals, and such modifications may often be designed and/or carried out by skilled veterinary pharmacologists through ordinary (if any) experimentation only, including, but not limited to, humans, other primates, and other manmade animals, including commercially relevant mammals such as cows, pigs, hoses, sheep, cats, dogs, rats and/or mice.

The pharmaceutical composition comprising one or more nanoparticle compositions may be prepared by any method known or hereafter developed in the field of pharmacology. Generally, such methods of preparation involve combining the active ingredient with excipients and/or one or more other auxiliary ingredients and then, if desired or necessary, dividing, shaping and/or packaging the product into the desired single or multiple dosage units.

The pharmaceutical compositions according to the present application may be manufactured, packaged and/or sold in bulk in a single unit dose and/or in a plurality of single unit doses. As used herein, a "unit dose" is the precise amount of a pharmaceutical composition that contains a predetermined amount of active ingredient (e.g., a nanoparticle composition). The amount of active ingredient is generally equal to the dose of active ingredient to be administered to the subject and/or a convenient fraction of that dose, for example half or one third of that dose.

The pharmaceutical compositions may be prepared in a variety of forms suitable for a variety of routes and methods of administration. For example, the pharmaceutical compositions may be prepared in liquid dosage forms (e.g., emulsions, microemulsions, nanoemulsions, solutions, suspensions, syrups, and medicaments), injectable forms, solid dosage forms (e.g., capsules, tablets, troche etc.), liquids, powders, and granules), formulations for topical and/or transdermal administration (e.g., ointments, pastes, creams, lotions, gels, powders, solutions, sprays, inhalants and patches), suspensions, powders, and other forms. Liquid dosage forms for oral and parenteral administration include, but are not limited to, pharmaceutically acceptable emulsions, microemulsions, nanoemulsions, solutions, suspensions, syrups and/or drugs.

In addition to the active ingredients, the liquid dosage forms may include inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed oil, groundnut oil, corn oil, germ oil, olive oil, castor oil, and sesame oil), glycerol, tetrahydrofurfuryl alcohol, polyethylene glycols and fatty acid esters of sorbitol and mixtures thereof. In addition to inert diluents, the oral compositions may also include other therapeutic and/or prophylactic agents, other agents, such as wetting agents, emulsifying and suspending agents, sweeteners, flavors, and/or fragrances. In certain embodiments for parenteral administration, the composition is mixed with a solubilizing agent (e.g., an alcohol, oil, modified oil, glycol, polysorbate, cyclodextrin, polymer, and/or combinations thereof).

Injectable preparations, for example, sterile injectable aqueous or oleaginous suspensions may be formulated according to the known techniques using suitable dispersing, wetting and/or suspending agents. The sterile injectable preparation may be a sterile injectable solution, suspension and/or emulsion in a non-toxic parenterally-acceptable diluent and/or solvent, for example as a solution in 1,3-butanediol. Acceptable vehicles and solvents, including water may be used. Sterile, nonvolatile oils are conventionally employed as a solvent or suspending medium. For this purpose, any mild nonvolatile oils, including synthetic mono- or diglycerides may be employed. Fatty acids such as oleic acid may be used in the preparation of injectables.

The injectable formulations may be sterilized, for example, by filtration through a bacterial-retaining filter and/or by incorporating sterilizing agents in the form of sterile solid compositions which may be dissolved or dispersed in sterile water or other sterile injectable medium prior touse.

In order to prolong the effect of the active ingredient, it is often desirable to slow the absorption of the active ingredient from subcutaneous or intramuscular injection. This may be achieved by using a liquid suspension of crystalline or amorphous material which is poorly water soluble. The rate of absorption of the drug then depends on its rate of dissolution, which in turn depends on the crystal size and crystal form. Alternatively, delayed absorption of a parenterally administered drug form is achieved by dissolving or suspending the drug in an oil carrier. Injectable depot forms are made by forming microencapsule matrices of the drug in biodegradable polymers (such as polylactic acid-polyethylene glycol). The rate of drug release may be controlled depending on the ratio of drug to polymer and the nature of the used particular polymer. Examples of other biodegradable polymers include poly(ortho-esters) and poly(anhydrides). Stock injection formulations are prepared by embedding the drug in liposomes or microemulsions that are compatible with body tissues.

Compositions for rectal or vaginal administration are typically suppositories which may be prepared by mixing the composition with suitable non-irritating excipients such as cocoa butter, polyethylene glycol or a suppository wax. Said excipients are solid at ambient temperature but liquid at body temperature and therefore melt in the rectum or vaginal cavity and release the active ingredient.

Solid dosage forms for oral administration include capsules, tablets, pills, films, powders and granules. In such solid dosage forms, the active ingredient is mixed with at least one inert pharmaceutically acceptable excipient, such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidone, sucrose, and acacia), humectants (e.g., glycerol), disintegrating agents (e.g., agar, calcium carbonate, potato starch or tapioca starch, alginic acid, certain silicates, and sodium carbonate), retarding agents (e.g., paraffin), absorption enhancers (e.g., quaternary ammonium compounds), wetting agents (e.g., cetyl alcohol and glyceryl monostearate), absorbents (e.g., kaolin and bentonite, silicates), and lubricants (e.g., talc), calcium stearate, magnesium stearate, solid polyethylene glycols, sodium lauryl sulfate), and mixtures thereof. In the case of capsules, tablets and pills, the dosage forms may comprise buffering agents.

Solid compositions of a similar type may be employed as fillers in soft and hard-filled gelatin capsules, which use excipients such as lactose or milk sugars, as well as high molecular weight polyethylene glycols and the like. Solid dosage forms such as tablets, dragees, capsules, pills, and granules may be prepared with coatings and shells such as enteric coatings and other coatings well known in the pharmaceutical formulating art. They may optionally contain opacifying agents and may have a composition that they release the active ingredient only, or preferably, in a certain part of the intestinal tract, optionally, in a delayed manner. Examples of embedding compositions that may be used include polymeric substances and waxes. Solid compositions of a similar type may be employed excipients such as lactose or milk sugars, as well as high molecular weight polyethylene glycols and the like as fillers in soft and hard-filled gelatin capsules.

Dosage forms for topical and/or transdermal administration of the compositions may include ointments, pastes, creams, lotions, gels, powders, solutions, sprays, inhalants and/or patches. Typically, the active ingredient is mixed under sterile conditions with pharmaceutically acceptable excipients and/or any preservatives and/or buffers that may be required. In addition, the present application contemplates the use of transdermal patches, which generally have the added advantage of providing controlled delivery of the compound to the body. Such dosage forms may be prepared, for example, by dissolving and/or dispensing the compound in the appropriate medium. Alternatively or additionally, the rate may be controlled by either providing a rate controlling membrane and/or by dispersing the compound in a polymer matrix and/or gel.

Formulations suitable for topical administration include, but are not limited to, liquid and/or semi-liquid formulations such as liniments, lotions, oil-in-water and/or water-in-oil emulsions such as creams, ointments and/or pastes, and/or solutions and/or suspensions, although the concentration of the active ingredient may be as high as the solubility limit of the active ingredient in the solvent. Formulations for topical administration may further comprise one or more of the other ingredients described herein.

The pharmaceutical compositions may be prepared, packaged and/or sold in a formulation suitable for pulmonary administration via the oral cavity. Such formulations may comprise dry particles of the active ingredient. Such compositions are conveniently in dry powder form for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Powder compositions may comprise a solid fine powder diluent, such as a sugar, and are conveniently provided in unit dose form.

Low boiling point propellants typically include liquid propellants having a boiling point below 65° F. at atmospheric pressure. Typically, the propellant may constitute 50% to 99.9% (wt/wt) of the composition, while the active ingredient may constitute 0.1% to 20% (wt/wt) of the composition. The propellant may further comprise other ingredients such as liquid nonionic and/or solid anionic surfactants and/or solid diluents (the particle size of which may be of the same order as the particles comprising the active ingredient).

Pharmaceutical compositions formulated for pulmonary delivery may provide the active ingredient in the form of droplets of solution and/or suspension. Such formulations may be prepared, packaged and/or sold as aqueous and/or diluted alcoholic solutions and/or suspensions, optionally sterile, containing the active ingredient and may conveniently be administered using any atomizing and/or nebulizing device. Such formulations may further comprise one or more other ingredients including, but not limited to, flavors such as sodium saccharin, volatile oils, buffering agents, surfactants, and/or preservatives such as methyl hydroxybenzoate. The average diameter of the droplets provided by this route of administration may be in the range of 1 nm to 200 nm.

The formulations useful for pulmonary delivery described herein may be used for intranasal delivery of pharmaceutical compositions. Another formulation suitable for intranasal administration is a coarse powder comprising the active ingredient and having an average particle size of 0.2 to 500 m. Such formulations are administered in the form of snuff by rapid inhalation through the nasal passage from a powder container held near the nose.

Formulations suitable for nasal administration may, for example, contain from 0.1% (wt/wt) to 100% (wt/wt) of the active ingredient, and may contain one or more of the other active ingredients described herein. The pharmaceutical compositions may be prepared, packaged and/or sold in formulations suitable for buccal administration. Such formulations may, for example, be in the form of tablets and/or lozenges prepared using conventional methods and may, for example, be 0.1% to 20% (wt/wt) of the active ingredient, the remaining part comprising an orally dissolvable and/or degradable composition, and optionally, one or more other ingredients described herein. Alternatively, formulations suitable for oral administration may comprise powders and/or aerosolized and/or atomized solutions and/or suspensions containing the active ingredient. Such powdered, aerosolized and/or aerosolized formulations, when dispersed, may have an average particle and/or droplet size in the range of 0.1 nm to 200 nm, and may further comprise one or more other ingredients described herein.

The pharmaceutical compositions may be prepared, packaged and/or sold in a formulation suitable for ophthalmic administration. Such formulations may be in the form of, for example, drops comprising, for example, a 0.1/1.0% (wt/wt) solution and/or suspension of the active ingredient in an aqueous or oleaginous liquid excipient. Such drops may further comprise a buffer, a salt and/or one or more of any other additive ingredients described herein. Other formulations useful for ophthalmic administration include those comprising the active ingredient in microcrystalline and/or liposomal form. Ear drops and/or eye drops are contemplated as being within the scope of the present disclosure.

Method of Producing a Polypeptide in a Cell

The present application further provides methods for producing a polypeptide of interest in a mammalian cell. Methods of producing a polypeptide include contacting a cell with a nanoparticle composition comprising an mRNA encoding a polypeptide of interest. After contacting the cell with the nanoparticle composition, the mRNA may be taken up and translated in the cell to produce the polypeptide of interest.

Generally, the step of contacting the mammalian cell with the nanoparticle composition comprising mRNA encoding the polypeptide of interest may be performed in vivo, ex vivo, in culture, or in vitro. The amount of nanoparticle composition contacted with the cell and/or the amount of mRNA therein may depend on the type of cell or tissue being contacted, the mode of administration, the physicochemical properties of the nanoparticle composition and the mRNA (e.g., size, charge, and chemical composition), and other factors. Generally, an effective amount of the nanoparticle composition will allow for efficient production of the polypeptide in the cell. Measures of efficiency may include polypeptide translation (as indicated by polypeptide expression), mRNA degradation levels, and immune response indicators.

The step of contacting the nanoparticle composition comprising mRNA with the cell may involve or cause transfection. The phospholipid included in the lipid component of the nanoparticle composition may facilitate transfection and/or increase the efficiency of transfection, for example, by interacting and/or fusing with cells or intracellular membranes. Transfection may allow translation of mRNA in the cell.

In some embodiments, the nanoparticle compositions described herein may be used in therapy. For example, the mRNA contained in the nanoparticle composition may encode a therapeutic polypeptide (e.g., in a translatable region) and produce the therapeutic polypeptide upon contacting with and/or entry (e.g., transfection) into a cell. In other embodiments, the mRNA contained in the nanoparticle composition may encode a polypeptide that may improve or increase immunity in a subject. For example, the mRNA may encode granulocyte colony stimulating factor or trastuzumab.

In certain embodiments, the mRNA included in the nanoparticle composition may encode a recombinant polypeptide that may replace one or more polypeptides that may be substantially not present in the cell contacted with the nanoparticle composition. One or more substantially absent polypeptides may be absent due to genetic mutations in the encoding gene or regulatory pathways thereof. Alternatively, a recombinant polypeptide produced by translation of an mRNA may antagonize the activity of an endogenous protein present in, on the surface of, or secreted from the cell. Antagonistic recombinant polypeptides may be desirable to combat deleterious effects caused by the activity of the endogenous protein, such as localization caused by altered activity or mutations.

In another alternative, a recombinant polypeptide produced by translation of an mRNA may indirectly or directly antagonize the activity of a biological moiety present in, on the surface of, or secreted from the cell. Antagonistic biological moieties may include, but are not limited to, lipids (e.g., cholesterol), lipoproteins (e.g., low density lipoproteins), nucleic acids, carbohydrates, and small molecule toxins. Recombinant polypeptides produced by translation of mRNA may be engineered to be localized within a cell, e.g., within a particular compartment such as the nucleus, or may be engineered to be secreted from the cell or transported to the plasma membrane of the cell.

In some embodiments, contacting a cell with a nanoparticle composition comprising mRNA may reduce the innate immune response of the cell to the exogenous nucleic acid. The cell may be contacted with a first nanoparticle composition comprising a first amount of a first exogenous mRNA including a translatable region, and a level of an innate immune response of the cell to the first exogenous mRNA may be determined. Subsequently, the cell may be contacted with a second composition comprising a second amount of the first exogenous mRNA, the second amount being a lesser amount of the first exogenous mRNA compared to the first amount. Alternatively, the second composition may comprise a first amount of a second exogenous mRNA that is different from the first exogenous mRNA. The step of contacting the cell with the first and second compositions may be repeated one or more times. In addition, the efficiency of polypeptide production (e.g., translation) in the cell may optionally be determined, and the cell may be repeatedly re-contacted with the first and/or second composition until the production efficiency of target protein is achieved.

The present application further provides a method of treating a disease or disorder in a mammal, comprising administering to the mammal a therapeutically effective amount of the nanoparticle composition of any one of the preceding items, in particular, the nanoparticle composition is useful for treating a disease, disorder or condition characterized by a loss or abnormality in protein or polypeptide activity. For example, a nanoparticle composition comprising mRNA encoding a deleted or aberrant polypeptide may be administered or delivered to a cell. Subsequent translation of the mRNA may produce the polypeptide, thereby reducing or eliminating problems caused by lack of or aberrant activity by the polypeptide. Because translation may occur rapidly, these methods and compositions may be useful for treating acute diseases, disorders or conditions such as sepsis, stroke, and myocardial infarction. The therapeutic and/or prophylactic agents included in the nanoparticle compositions may also be capable of altering the transcription rate of a given species, thereby affecting gene expression.

Diseases, disorders and/or conditions characterized by a dysfunctional or abnormal protein or polypeptide activity include, but are not limited to, rare diseases, infectious diseases (e.g., vaccines and therapeutics), cancer and proliferative diseases, genetic diseases (e.g., cystic fibrosis), autoimmune diseases, diabetes, neurodegenerative diseases, cardiovascular and renal vascular diseases, and metabolic diseases.

The present application provides methods involving administering nanoparticle compositions comprising one or more therapeutic and/or prophylactic agents and pharmaceutical compositions comprising the nanoparticle compositions. The terms therapeutic and prophylactic are used interchangeably herein with respect to the features and embodiments of the present application. The therapeutic composition or imaging, diagnostic, or prophylactic composition thereof may be administered to a subject using any reasonable amount and any route of administration effective to prevent, treat, diagnose, or image a disease, disorder, and/or condition and/or any other purpose. The specific amount administered to a particular subject may vary depending on the species, age, and general condition of the subject; administration purposes; specific ingredients; administration mode; and so on. The compositions according to the present application may be formulated in unit dosage form for ease of administration and uniformity of dosage. It will be understood, however, that the total daily amount of the composition of the present application will be determined by the attending physician within the scope of rational medical judgment. The specific therapeutically effective, prophylactically effective, or other appropriate dosage level (e.g., for imaging) for any particular patient will depend upon a variety of factors, including the severity and identification (if any) of the disease being treated; one or more therapeutic and/or prophylactic agents used; the specific ingredients used; the age, body weight, general health, sex, and diet of the patient; the time of administration, route of administration and rate of excretion of the particular pharmaceutical ingredient employed; the duration of the treatment; drugs used in combination or concomitantly with the specific pharmaceutical ingredients as used; and factors well known in the medical field.

The present application further provides a method of specifically delivering a therapeutic and/or prophylactic agent to a mammalian organ, comprising administering the nanoparticle composition of any one of the preceding items to the mammal, said administering comprising contacting the mammalian organ with the nanoparticle composition, thereby delivering the therapeutic and/or prophylactic agent to the organ. The therapeutic and/or prophylactic agent, such as proteins, cytotoxic agents, radioactive ions, chemotherapeutic agents, or nucleic acids (e.g., RNA, for example mRNA) may be delivered to the cell or organ. In the case where the therapeutic and/or prophylactic is mRNA, the translatable mRNA may be translated in the cell to produce the polypeptide of interest when the cell is contacted with the nanoparticle composition. However, substantially untranslatable mRNAs may also be delivered to the cell. The substantially untranslatable mRNA may be used as a vaccine and/or may sequester translation components of the cell to reduce expression of other species in the cell.

In some embodiments, the nanoparticle composition may target a particular type or class of cell (e.g., a cell of a particular organ or system thereof). For example, a nanoparticle composition comprising a therapeutic and/or prophylactic agent of interest may be specifically delivered to the liver, kidney, spleen, femur, gastrointestinal tract, or lung of a mammal. Specific delivery to a particular class of cells, organs or systems or groups thereof means that a higher proportion of the nanoparticle composition including a therapeutic and/or prophylactic agent is delivered to the target destination (e.g., a tissue) relative to other destinations, for example, when the nanoparticle composition is administered to a mammal. In some embodiments, the target tissue is selected from liver, kidney, lung, spleen, femur, eye, gastrointestinal tract tissue (e.g., by intraocular, subretinal, or intravitreal injection), vascular endothelium in blood vessels (e.g., intra-coronary or intra-femoral) or kidney, and tumor tissue (e.g., by intratumoral injection).

As another example of targeted or specific delivery, an mRNA encoding a protein binding partner (e.g., an antibody or functional fragment thereof, a scaffold protein or peptide) or receptor on the surface of a cell may be included in the nanoparticle composition. The mRNA may be increased alternatively or alternatively for directing the synthesis and extracellular localization of lipids, carbohydrates or other biological moieties. Alternatively, other therapeutic and/or prophylactic agents or elements (e.g., lipids or ligands) of the nanoparticle composition may be selected based on their affinity for a particular receptor (e.g., low density lipoprotein receptor) such that the nanoparticle composition may more readily interact with a target cell population that includes the receptor.

In some embodiments, the ligand may be a surface-bound antibody, which may allow for modulation of cell targeting specificity. This is particularly useful because highly specific antibodies can be raised against the epitope of interest at the desired target site. In one embodiment, multiple antibodies are expressed on the cell surface, and each antibody may have a different specificity for a desired target. Such approach may improve the affinity and specificity of the targeted interaction.

The targeted cells may include, but are not limited to, hepatocytes, epithelial cells, hematopoietic cells, epithelial cells, endothelial cells, lung cells, bone cells, stem cells, mesenchymal cells, neural cells, heart cells, adipocytes, vascular smooth muscle cells, cardiac muscle cells, skeletal muscle cells, beta cells, pituitary cells, synovial lining cells, ovarian cells, testicular cells, fibroblasts, B cells, T cells, reticulocytes, leukocytes, granulocytes, and tumor cells.

In some embodiments, the nanoparticle composition may target hepatocytes.

In some embodiments, the nanoparticle composition may target extrahepatic cells.

In some preferred embodiments, the nanoparticle composition may target spleen, stomach, or intestinal tract.

The nanoparticle composition of the present application may be administrated by any route. In some embodiments, a composition comprising a prophylactic, diagnostic or imaging composition comprising one or more nanoparticle compositions of the present application is administered by one or more of a variety of routes, including orally, intravenously, intramuscularly, intra-arterially, intramedullary, intrathecally, subcutaneously, intraventricularly, transdermally or intradermally, rectally, intravaginally, intraperitoneally, intraocularly, subretinally, intravitreally, topically (e.g., by powders, ointments, creams, gels, lotions, and/or drops), mucosally, nasally, buccally, enterally, vitreally, intratumorally, sublingually, intranasally, by intratracheal instillation, bronchial instillation, and/or inhalation; as an oral spray and/or powder, nasal spray and/or aerosol, and/or via a portal vein catheter. In some embodiments, the composition may be administered intravenously, intramuscularly, intradermally, intraarterially, intratumorally, subcutaneously, intraocularly, subretinally, intravitreally, or by inhalation. However, in view of the possible advances in the science of drug delivery, the present application contemplates delivery or description of the compositions described herein by any suitable route. In general, the most suitable route of administration depends on a variety of factors, including the nature of the nanoparticle composition, including one or more therapeutic and/or prophylactic measures (e.g., its stability in various body environments (e.g., blood and gastrointestinal tract)), the condition of the patient (e.g., whether the patient is able to tolerate a particular route) management), and so forth.

In certain embodiments, wherein a therapeutic and/or prophylactic agent is administered to the mammal at a dose of 0.0001 mg/kg to 10 mg/kg. For example, it may be 0.0001 mg/kg to 10 mg/kg, 0.001 mg/kg to 10 mg/kg, 0.005 mg/kg to 10 mg/kg, 0.01 mg/kg to 10 mg/kg, 0.05 mg/kg to 10 mg/kg, 0.1 mg/kg to 10 mg/kg 1 mg/kg to 10 mg/kg, 2 mg/kg to 10 mg/kg, 5 mg/kg to 10 mg/kg, 0.0001 mg/kg to 5 mg/kg, 0.001 mg/kg to 5 mg/kg, 0.005 mg/kg to 5 mg/kg, 0.01 mg/kg to 5 mg/kg, 0.05 mg/kg to 5 mg/kg, 0.1 mg/kg to 5 mg/kg, 1 mg/kg to 5 mg/kg, 2 mg/kg to 5 mg/kg, 0.0001 mg/kg to 2.5 mg/kg, 0.001 mg/kg to 2.5 mg/kg, 0.005 mg/kg to 2.5 mg/kg, 0.01 mg/kg to 2.5 mg/kg 0.05 mg/kg to 2.5 mg/kg, 0.1 mg/kg to 2.5 mg/kg, 1 mg/kg to 2.5 mg/kg, 2 mg/kg to 2.5 mg/kg, 0.0001 mg/kg to 1 mg/kg, 0.001 mg/kg to 1 mg/kg, 0.005 mg/kg to 1 mg/kg, 0.01 mg/kg to 1 mg/kg, 0.05 mg/kg to 1 mg/kg, 0.1 mg/kg to 1 mg/kg, 0.0001 mg/kg to 0.25 mg/kg, 0.001 mg/kg to 0.25 mg/kg, 0.005 mg/kg to 0.25 mg/kg, 0.01 mg/kg to 0.25 mg/kg, 0.05 mg/kg to 0.25 mg/kg or 0.1 mg/kg to 0.25 mg/kg. In some embodiments, a therapeutic and/or prophylactic (e.g., mRNA) dose of the nanoparticle composition may be administered in a range from about 0.001 mg/kg to about 10 mg/kg. In other embodiments, a therapeutic and/or prophylactic dose of about 0.005 mg/kg to about 2.5 mg/kg may be administered. In certain embodiments, a dose of about 0.1 mg/kg to about 1 mg/kg may be administered. In other embodiments, a dose of about 0.05 mg/kg to about 0.25 mg/kg may be administered. The dose may be administered one or more times per day in the same or different amounts to achieve the desired level of mRNA expression and/or therapeutic, diagnostic, prophylactic or imaging effect. The desired dose may be delivered, for example, three times daily, twice daily, once daily, every other day, every third day, weekly, every two weeks, every three weeks, or every four weeks. In certain embodiments, multiple administrations (e.g., two, three, four, five, six, seven, eight, nine, ten, eleven, twelve, thirteen, fourteen or more administrations) may be used to deliver the desired dose. In some embodiments, for example, before or after surgery, or in the case of an acute disease, disorder, or condition, a single dose may be administered.

Nanoparticle compositions comprising one or more therapeutic and/or prophylactic agents may be used in combination with one or more other therapeutic, prophylactic, diagnostic or imaging agents. "In combination with" does not mean that the agents must be administered simultaneously and/or formulated for delivery together, although such delivery methods are within the scope of the present application. For example, one or more nanoparticle compositions comprising one or more different therapeutic and/or prophylactic agents may be administered in combination. The composition may be administered concurrently with, prior to, or subsequent to one or more other desired therapeutic or medical procedures. Typically, each agent will be administered at a dose and/or on a schedule determined for that agent. In some embodiments, the present application includes the delivery of the composition or an imaging, diagnostic or prophylactic composition thereof in combination with an agent that increases its bioavailability, reduces and/or alters its metabolism, inhibits its excretion and/or modulates contractions in vivo.

It is understood that the therapeutically, prophylactically, diagnostically or imaging active agents used in combination may be administered together in a single composition or separately in different compositions. In general, it is desirable that the agents used in combination are used at levels not exceeding the levels at which they are used individually. In some embodiments, the level of combined use may be lower than the level used individually.

The particular combination of treatments (treatments or procedures) used in a combination regimen will take into account the compatibility of the desired treatments and/or procedures as well as the desired therapeutic effect to be achieved. It will also be appreciated that the treatments employed may achieve the desired effect on the same condition (e.g., the composition used to treat cancer may be administered concurrently with the chemotherapeutic agent), or they may achieve different effects (e.g., control of any side effects, such as infusion-related reactions).

In some embodiments, a method of treating a subject in need thereof or delivering a therapeutic and/or prophylactic drug to a subject (e.g., a mammal) may comprise pretreating the subject with one or more agents prior to administering the nanoparticle composition. For example, the subject may be pretreated with an effective amount (e.g., 10 mg, 20 mg, 30 mg, 40 mg, 50 mg, 60 mg, 70 mg, 80 mg, 90 mg, 100 mg, or any other effective amount) of dexamethasone, methotrexate, acetaminophen, H1 receptor blockers, or H2 receptor blockers. The pre-treatment may occur 24 hours or less (e.g., 24 hours, 20 hours, 16 hours, 12 hours, 8 hours, 4 hours, 2 hours, 1 hour, 50 minutes, 40 minutes, 30 minutes, 20 minutes, or 10 minutes) prior to administration of the nanoparticle composition, and may occur, for example, once, twice, or more with increasing doses.

The various embodiments described herein (including the Examples below) and the features in the various embodiments should be understood as be able to arbitrarily combine with each other, and the various embodiments resulting from these combinations are included within the scope of the present application as if the embodiments resulting from these combinations were specifically and individually set forth herein, unless the context clearly indicates otherwise.

EXAMPLES

Figure 1:
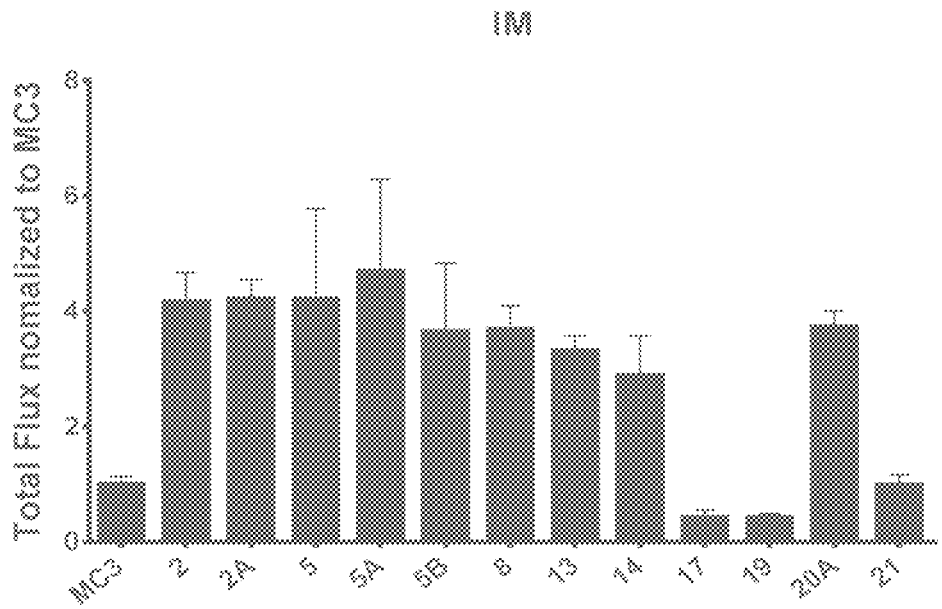
FIG. 1 shows the luciferase expression results of LNPs prepared based on the compounds of the present invention 24 h after intramuscular injection.
Figure 2A:
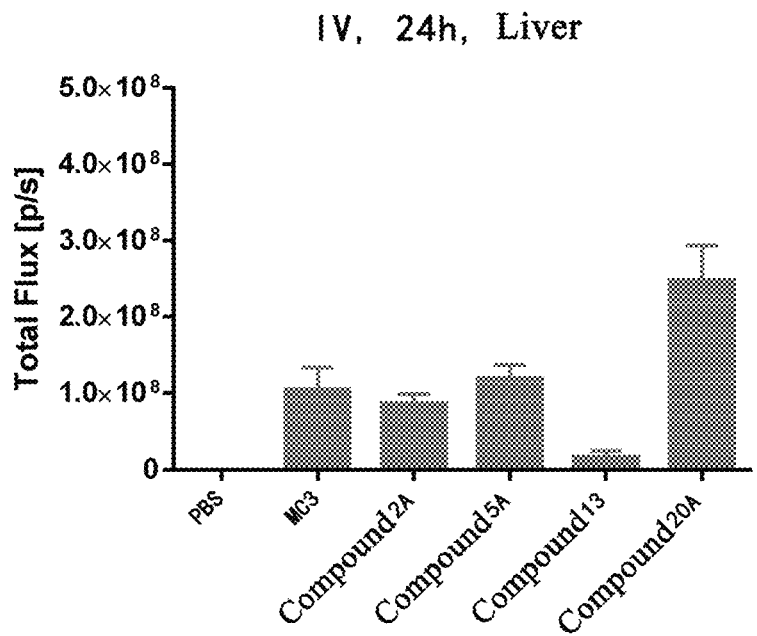
FIGS. 2A-2D show the luciferase tissue organ distribution of LNPs prepared based on the compounds of the present invention 24 h after intravenous injection.
Figure 2B:
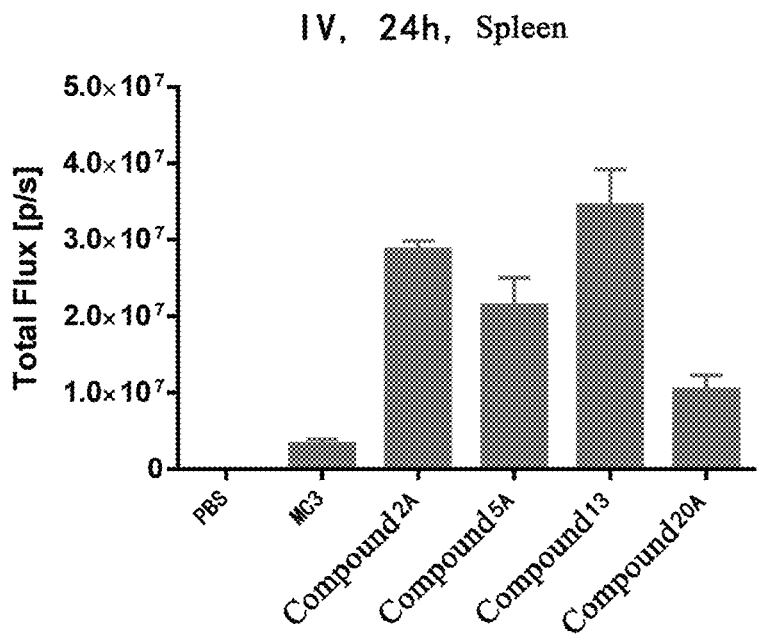
Figure 2C:
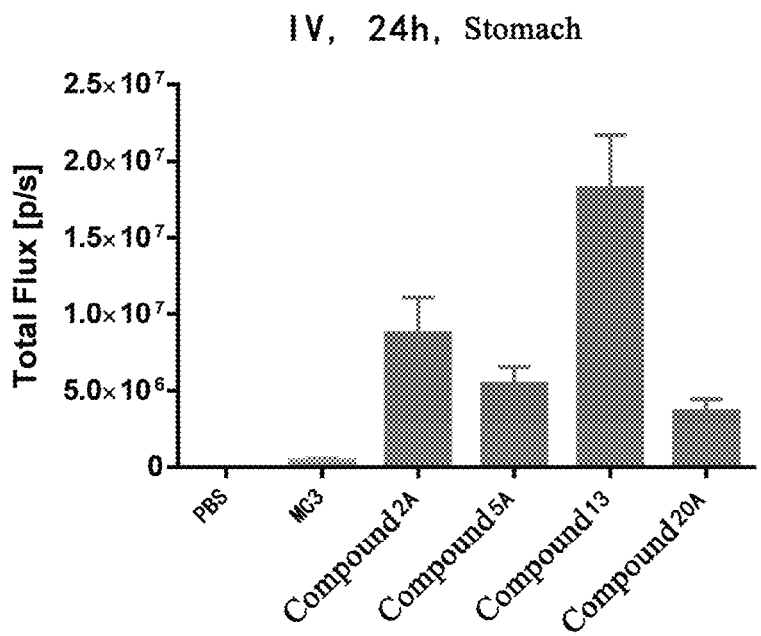
Figure 2D:
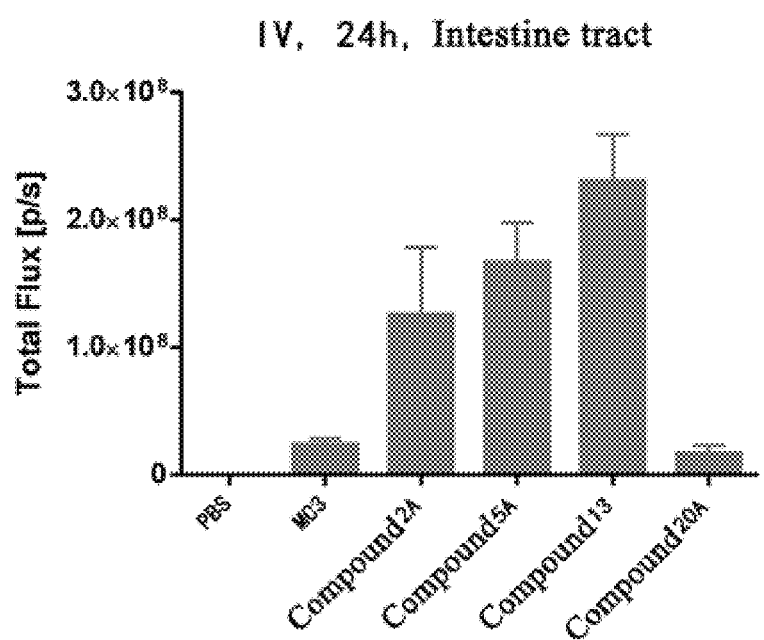

The following examples are illustrative of the present application and are not intended to limit the present application in any way. Unless otherwise indicated, all temperatures are in degrees Celsius and the pressure is at or near atmospheric. All reagents and starting materials used in the present application are commercially available except as synthetic intermediates or where otherwise indicated.

Example 1 Synthesis of Compound 1
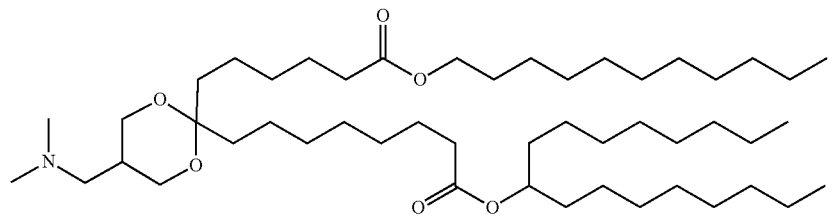
Compound 1
The synthetic route is shown as follows:
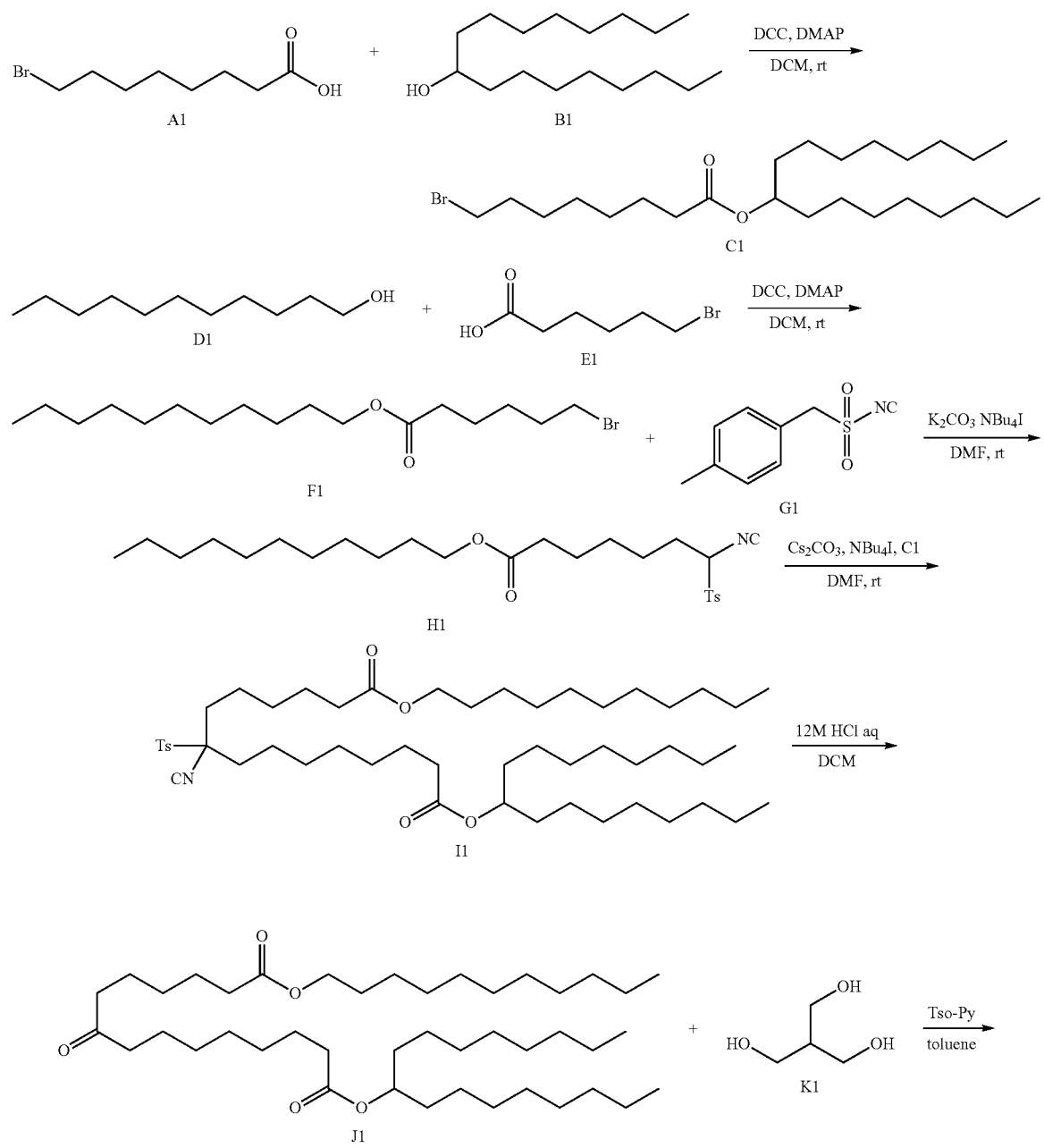

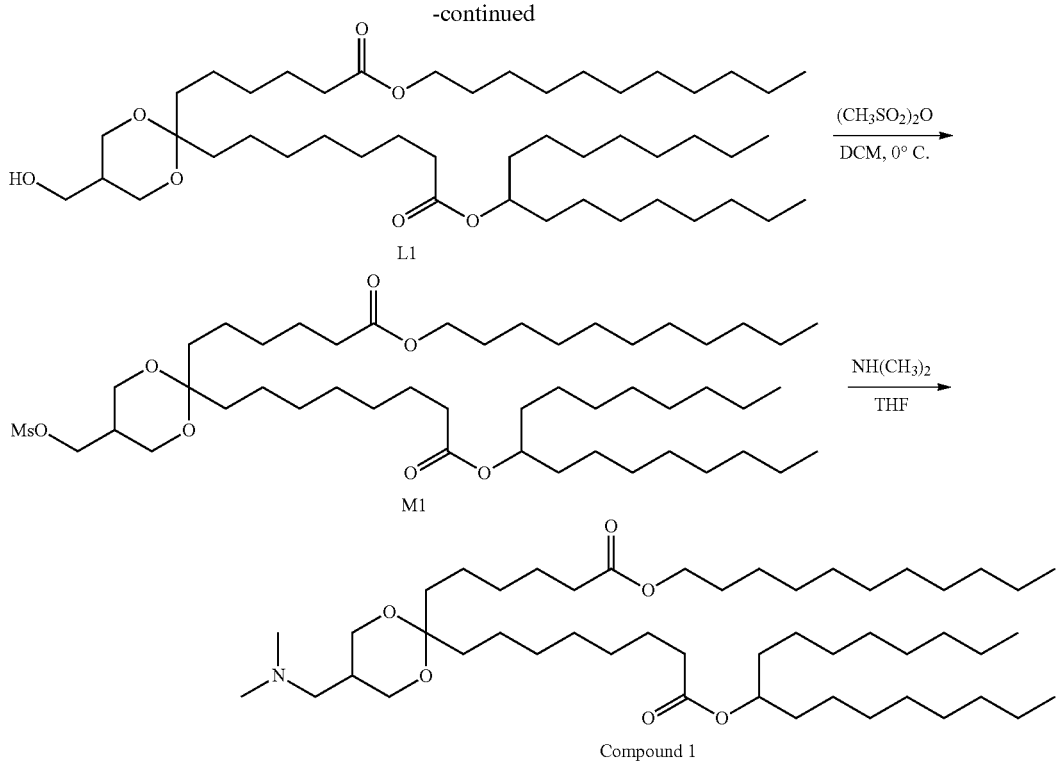

Specifically, to a solution of Compound A1 (2.0 g, 8.96 mmol) in dichloromethane (30 ml) were added Compound B1 (1.9 g, 7.47 mmol), DCC (1.8 g, 8.96 mmol) and DMAP (437 mg, 3.58 mmol), and the reaction mixture was stirred for 7 hours at room temperature and monitored by TLC. After completion of the reaction, the reaction mixture was diluted by adding an equal volume of saturated sodium bicarbonate solution, and separated. The organic layer was dried over anhydrous magnesium sulfate, and filtered. The filtrate was concentrated, and purified on silicagel column chromatography (petroleum ether:ethyl acetate=30:1) to obtain Compound C1 (2.9 g, 85.00%).

To a solution of Compound E1 (5.0 g, 25.63 mmol) in dichloromethane (60 ml) were added Compound D1 (3.7 g, 21.36 mmol), DCC (5.29 g, 25.63 mmol) and DMAP (1.2 g, 10.25 mmol), and the reaction mixture was stirred for 7 hours at room temperature and monitored by TLC. After completion of the reaction, the reaction mixture was diluted by adding an equal volume of saturated sodium bicarbonate solution, and separated. The organic layer was dried over anhydrous magnesium sulfate, and filtered. The filtrate was concentrated, and purified on silica gel column chromatography (petroleum ether:ethyl acetate=30:1) to obtain Compound F1 (6.5 g, 88.00%).

To a solution of Compound F1 (500 mg, 1.44 mmol) in DMF (15 ml) were added Compound G (562 mg, 2.88 mmol), NBu$_4$I (795 mg, 2.15 mmol) and K$_2$CO$_3$ (597 mg, 4.32 mmol), and the reaction mixture was stirred for 12 hours at room temperature and monitored by TLC. After completion of the reaction, the reaction mixture was diluted by adding an equal volume of water, extracted with ethyl acetate (10 ml×3), concentrated, and purified on silica gel column chromatography (petroleum ether:ethyl acetate=10:1) to obtain Compound H1 (580 mg, 87% yield).

To a solution of Compound H1 (500 mg, 1.08 mmol) in DMF (15 ml) were added Compound C1 (745 mg, 1.62 mmol), NBu$_4$I (598 mg, 1.62 mmol) and Cs$_2$CO$_3$ (1.4 g, 4.32 mmol), and the reaction mixture was stirred for 15 hours at room temperature and monitored by TLC. After completion of the reaction, the reaction mixture was diluted by adding an equal volume of water, extracted with ethyl acetate (10 ml×3), concentrated, and purified on silica gel column chromatography (petroleum ether:ethyl acetate=10:1) to obtain Compound 11 (811 mg, yield 89%).

To a solution of Compound 11 (10 g, 11.85 mmol) in dichloromethane (100 ml) was added concentrated hydrochloric acid (60 ml), and the reaction mixture was stirred for 3 hours at room temperature and monitored by TLC. After completion of the reaction, the layers were separated. The organic layer was washed with saturated sodium bicarbonate solution, dried over anhydrous magnesium sulfate, concentrated, and purified on silica gel column chromatography (petroleum ether:ethyl acetate=30:1) to obtain Compound J1 (6.5 g, 81.00%).

To a solution of Compound J1 (1 g, 1.48 mmol) in toluene (25 ml) were added Compound K1 (470 mg, 4.44 mmol) and pyridinium 4-methylbenzenesulfonate (744 mg, 2.96 mmol), heated to reflux for 20 h with Dean-Stark apparatus, and the reaction was monitored by TLC. After completion of the reaction, the reaction mixture was cooled to room temperature, diluted by adding an equal volume of water, extracted with ethyl acetate (10 ml×3), concentrated, and purified on silica gel column chromatography (petroleum ether:ethyl acetate=5:1) to obtain Compound L1 (648 mg, 57% yield).

To a solution of Compound L1 (750 mg, 0.98 mmol) in ultra dry dichloromethane (10 ml) were added methanesulfonic anhydride (340 mg, 1.96 mmol) and anhydrous triethylamine (0.45 ml) at 0° C., stirred for 12 hours, and the reaction was monitored by TLC. After completion of the reaction, the reaction solution is cooled to room temperature, diluted by adding an equal volume of water, and separated. The organic layer was dried over anhydrous magnesium sulfate, and filtered. The filtrate was concentrated, and purified on silica gel column chromatography (petroleum ether:ethyl acetate=5:1) to obtain Compound M1 (800 mg, yield 97%).

To Compound M1 (750 mg, 0.89 mmol) was added a solution of dimethylamine (2M in THF) (30 ml), sealed, and stirred at room temperature for 6 days, and the reaction was monitored by TLC. After completion of the reaction, concentrated, and purified on silica gel column chromatography (dichloromethane:methanol=30:1) to obtain Compound 1 (212 mg, yield 30%) as an oil. $^1$H NMR (600 MHz, CDCl$_3$) δ 4.87-4.82 (m, 1H), 4.05-4.02 (m, 2H), 3.90-3.85 (m, 2H), 3.59-3.56 (m, 2H), 2.31-2.23 (m, 4H), 2.21-2.19 (m, 8H), 1.94-1.87 (brs, 1H), 1.68-1.56 (m, 10H), 1.52-1.42 (m, 4H), 1.36-1.21 (m, 52H), 0.87-0.84 (m, 9H); $^{13}$C NMR (151 MHz, CDCl$_3$) δ 173.98, 173.77, 100.76, 74.22, 64.55, 62.87, 62.81, 59.34, 59.31, 45.97, 35.37, 35.28, 34.86, 34.49, 34.46, 34.28, 32.47, 32.39, 32.03, 31.99, 29.99 29.72, 29.65, 29.46, 29.36, 28.80, 26.06, 25.44, 25.29, 25.16, 23.49, 23.26, 23.16, 22.92, 22.79, 14.22; MS-ESI (m/z): 794.6 (M+H)$^+$.

Example 2 Synthesis of Compound 2

Compound 2

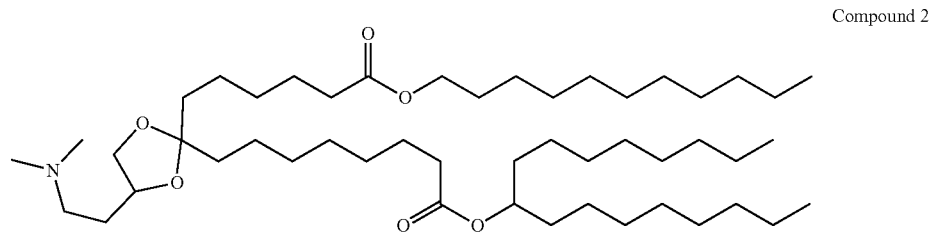 [SMILES: CCCCCCCCCCCOC(=O)CCCCCC1(CCCCCCCC(=O)OC(CCCCCCCC)CCCCCCCC)OCC(CCN(C)C)O1]

The method of preparation is the same as Compound 1, and 1,2,4-butanetriol was used to replace Compound K1 as raw material to produce Compound 2 as an oil. $^1$H NMR (600 MHz, CDCl$_3$) δ 4.82-4.78 (m, 1H), 4.04-3.96 (m, 4H), 3.42-3.39 (m, 1H), 2.39-2.34 (brs, 1H), 2.29-2.25 (brs, 1H), 2.23-2.18 (m, 10H), 1.77-1.71 (brs, 1H), 1.66-1.65 (brs, 1H), 1.58-1.39 (m, 13H), 1.33-1.16 (m, 53H), 0.82-0.80 (m, 9H); $^{13}$C NMR (151 MHz, CDCl$_3$) δ 173.62, 173.41, 111.82, 74.63, 74.61, 73.88, 69.89, 64.25, 56.18, 45.28, 37.73, 37.48, 37.40, 37.20, 34.59, 34.19, 34.18, 34.09, 31.83, 31.78, 31.60, 29.70, 29.68, 29.52, 29.50, 29.45, 29.34, 29.32, 29.25, 29.20, 29.15, 29.09, 29.07, 28.59, 25.86, 25.23, 25.07, 24.89, 23.88, 23.58, 23.56, 23.24, 22.60, 22.58, 14.01; MS-ESI (m/z): 794.6 (M+H)$^+$.

Example 2A Synthesis of Compound 2A

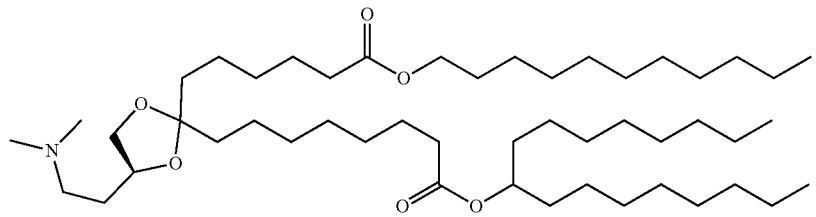

The method of preparation is the same as Compound 1, and (S)-1,2,4-butanetriol was used to replace Compound K1 as raw material to produce Compound 2A as an oil. $^1$H NMR (400 MHz, CDCl$_3$) δ 4.97-4.83 (m, 1H), 4.17-4.05 (m, 4H), 3.52 (t, J=8.0 Hz, 1H), 2.58-2.37 (m, 2H), 2.35-2.23 (m, 10H), 1.91-1.70 (m, 2H), 1.69-1.50 (m, 14H), 1.48-1.24 (m, 52H), 0.92 (t, J=8.0 Hz, 9H); $^{13}$C NMR (100 MHz, CDCl$_3$) δ 174.04, 173.69, 112.10, 74.59, 74.12, 69.94, 64.34, 56.22, 45.21, 37.79, 37.70, 37.44, 37.38, 34.74, 34.42, 34.16, 31.91, 31.88, 31.43, 31.41, 29.80, 29.57, 29.55, 29.52, 29.49, 29.32, 29.28, 29.25, 29.19, 28.63, 28.61, 25.95, 25.33, 25.17, 25.00, 23.89, 23.71, 23.59, 22.68, 14.12; MS-ESI (m/z): 795.0 (M+H)$^+$.

Example 3 Synthesis of Compound 3

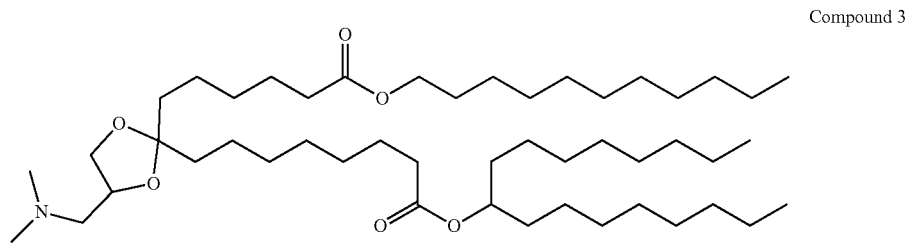 [SMILES: CCCCCCCCCCCOC(=O)CCCCCC1(CCCCCCCC(=O)OC(CCCCCCCC)CCCCCCCC)OCC(CN(C)C)O1]

Compound 3

The method of preparation is the same as Compound 1, and 3-dimethylamino-1,2-propanediol and p-toluenesulfonic acid monohydrate were used to replace Compound K1 and pyridinium 4-methylbenzenesulfonate as raw materials to produce Compound 3 as an oil. $^1$H NMR (600 MHz, CDCl$_3$) δ 4.85-4.81 (m, 1H), 4.20-4.16 (m, 1H), 4.06-4.01 (m, 3H), 3.49-3.46 (m, 1H), 2.48-2.44 (m, 1H), 2.35-2.32 (m, 1H), 2.27-2.22 (m, 10H), 1.60-1.54 (m, 8H), 1.48-1.47 (m, 4H), 1.31-1.20 (m, 54H), 0.86-0.83 (m, 9H); $^{13}$C NMR (151 MHz, CDCl$_3$) δ 173.90, 173.69, 112.58, 74.40, 74.36, 74.13, 69.06, 64.48, 62.62, 62.59, 46.22, 37.80, 37.55, 37.51, 37.30, 34.79, 34.40, 34.38, 34.24, 31.99, 31.94, 29.88, 29.83, 29.68, 29.66, 29.61, 29.58, 29.52, 29.47, 29.41, 29.38, 29.33, 29.31, 29.27, 29.25, 28.74, 26.01, 25.39, 25.24, 25.06, 25.06, 24.03, 23.70, 23.35, 22.74, 14.17; MS-ESI (m/z): 780.6 (M+H)$^+$.

Example 4 Synthesis of Compound 4

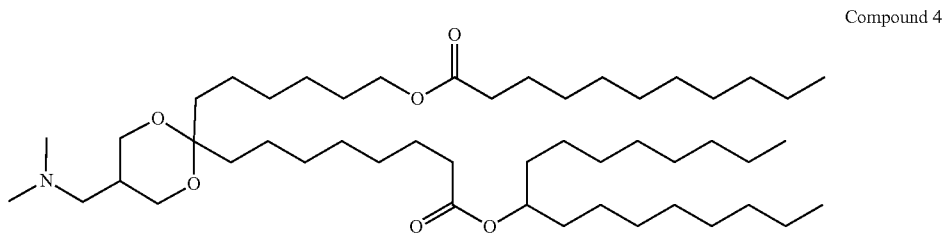 [SMILES: CCCCCCCCCCC(=O)OCCCCCCC1(CCCCCCCC(=O)OC(CCCCCCCC)CCCCCCCC)OCC(CN(C)C)CO1]

Compound 4

The method of preparation is the same as Compound 1, and undecanoic acid and 6-bromo-1-hexanol were used to replace Compound D1 and Compound E1 as raw materials to produce Compound 4 as an oil. $^1$H NMR (600 MHz, CDCl$_3$) δ 4.86-4.81 (m, 1H), 4.04-4.01 (m, 2H), 3.90-3.84 (m, 2H), 3.59-3.55 (m, 2H), 2.27-2.22 (m, 4H), 2.20-2.17 (m, 8H), 1.94-1.85 (brs, 1H), 1.67-1.55 (m, 10H), 1.48-1.45 (m, 4H), 1.36-1.22 (m, 52H), 0.86-0.83 (m, 9H); $^{13}$C NMR (151 MHz, CDCl$_3$) δ 174.01, 173.70, 100.73, 74.14, 64.40, 64.36, 62.83, 62.75, 59.31, 59.28, 45.98, 35.50, 35.25, 34.79, 34.47, 34.24, 32.45, 32.43, 32.22, 31.98, 31.95, 29.94, 29.70, 29.64, 29.61, 29.59, 29.55, 29.42, 29.39, 29.35, 29.32, 29.29, 29.25, 28.73, 26.05, 25.40, 25.24, 25.10, 23.45, 23.32, 23.21, 23.08, 22.75, 14.18; MS-ESI (m/z): 794.6 (M+H)$^+$.

Example 5 Synthesis of Compound 5

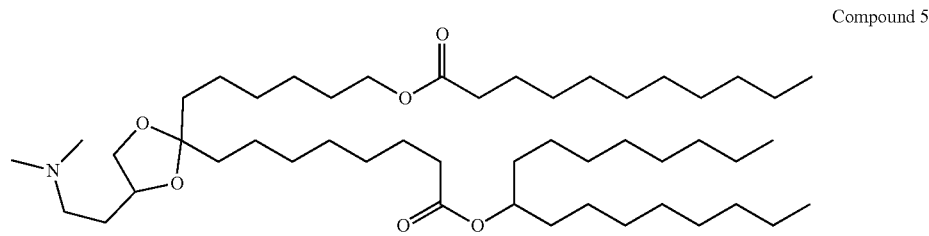 [SMILES: CCCCCCCCCCC(=O)OCCCCCCC1(CCCCCCCC(=O)OC(CCCCCCCC)CCCCCCCC)OCC(CCN(C)C)O1]

Compound 5

The method of preparation is the same as Compound 1, and undecanoic acid, 6-bromo-1-hexanol and 1,2,4-butanetriol were used to replace Compound D1, Compound E1 and Compound K1 as raw materials to produce Compound 5 as an oil. $^1$H NMR (600 MHz, CDCl$_3$) δ 4.81 (p, J=6.2 Hz, 1H), 4.03 (t, J=6.6 Hz, 1H), 3.99 (t, J=6.6 Hz, 3H), 3.42 (t, J=7.6 Hz, 1H), 2.41-2.36 (brs, 1H), 2.31-2.26 (brs, 1H), 2.23-2.20 (m, 10H), 1.78-1.73 (brs, 1H), 1.66-1.60 (brs, 1H), 1.58-1.43 (m, 12H), 1.31-1.20 (m, 54H), 0.82 (t, J=7.0 Hz, 9H); $^{13}$C NMR (151 MHz, CDCl$_3$) δ 173.92, 173.60, 112.00, 74.75, 74.73, 74.05, 70.00, 64.31, 56.29, 45.41, 37.83, 37.73, 37.50, 37.42, 34.73, 34.40, 34.20, 31.93, 31.90, 31.73, 31.71, 29.82, 29.80, 29.58, 29.56, 29.53, 29.50, 29.33, 29.30, 29.26, 29.20, 28.67, 28.65, 25.96, 25.35, 25.19, 25.05, 23.90, 23.71, 23.59, 22.69, 14.13; MS-ESI (m/z): 794.6 (M+H)$^+$.

Example 5A Synthesis of Compound 5A

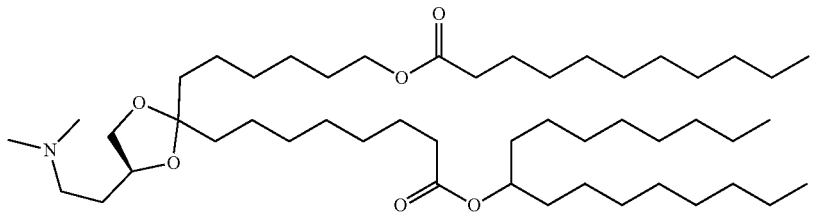

The method of preparation is the same as Compound 1, and undecanoic acid, 6-bromo-1-hexanol and (S)-1,2,4-butanetriol were used to replace Compound D1, Compound E1 and Compound K1 as raw materials to produce Compound 5A as an oil. $^1$H NMR (400 MHz, CDCl$_3$) δ 4.97-4.83 (m, 1H), 4.17-4.06 (m, 4H), 3.51 (t, J=4.0 Hz, 1H), 2.51-2.45 (m, 1H), 2.44-2.32 (m, 1H), 2.31-2.23 (m, 10H), 1.87-1.80 (m, 1H), 1.74-1.67 (m, 1H), 1.66-1.50 (m, 14H), 1.48-1.24 (m, 52H), 0.92 (t, J=8.0 Hz, 9H); $^{13}$C NMR (100 Hz, CDCl$_3$) δ 173.96, 173.62, 111.98, 74.71, 74.08, 69.96, 64.30, 56.24, 45.36, 37.60, 37.53, 37.50, 37.43, 34.71, 34.39, 34.13, 31.87, 31.84, 31.67, 31.61, 29.78, 29.70, 29.51, 29.48, 29.30, 29.28, 29.24, 29.18, 28.64, 28.61, 25.94, 25.32, 25.17, 25.03, 23.89, 23.70, 23.59, 22.67, 14.11; MS-ESI (m/z): 795.0 (M+H)$^+$.

Example 5B Synthesis of Compound Compound 5B

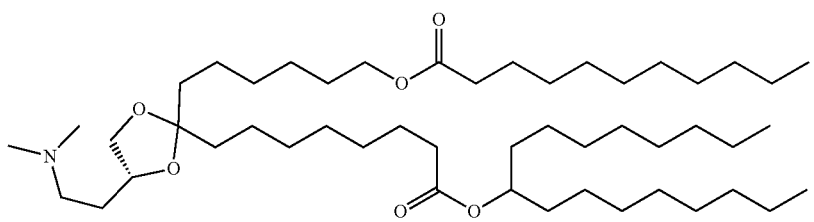

The method of preparation is the same as Compound 1, and undecanoic acid, 6-bromo-1-hexanol and (R)-1,2,4-butanetriol were used to replace Compound D1, Compound E1 and Compound K1 as raw materials to produce Compound 5B as an oil. $^1$H NMR (400 MHz, CDCl$_3$) δ 4.97-4.83 (m, 1H), 4.17-4.05 (m, 4H), 3.51 (t, J=4.0 Hz, 1H), 2.51-2.45 (m, 1H), 2.44-2.32 (m, 1H), 2.31-2.23 (m, 10H), 1.86-1.80 (m, 1H), 1.74-1.67 (m, 1H), 1.66-1.51 (m, 14H), 1.48-1.24 (m, 52H), 0.92 (t, J=8.0 Hz, 9H); $^{13}$C NMR (100 MHz, CDCl$_3$) δ 173.97, 173.62, 111.98, 74.71, 74.08, 69.96, 64.30, 56.24, 45.36, 37.60, 37.43, 37.50, 37.44, 34.71, 34.39, 34.13, 31.87, 31.84, 31.67, 31.61, 29.79, 29.70, 29.51, 29.48, 29.30, 29.28, 29.24, 29.18, 28.64, 28.61, 25.94, 25.32, 25.18, 25.03, 23.89, 23.70, 23.59, 22.67, 14.11; MS-ESI (m/z): 795.0 (M+H)$^+$.

Example 6 Synthesis of Compound 6

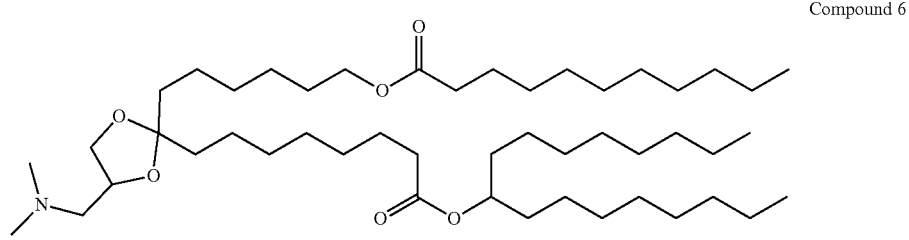 [SMILES: CCCCCCCCCCC(=O)OCCCCCCC1(CCCCCCCC(=O)OC(CCCCCCCC)CCCCCCCC)OCC(CN(C)C)O1]

Compound 6

The method of preparation is the same as Compound 1, and undecanoic acid, 6-bromo-1-hexanol and 3-dimethylamino-1,2-propanediol were used to replace Compound D1, Compound E1 and Compound K1 as raw materials to produce Compound 6 as an oil. $^1$H NMR (500 MHz, CDCl$_3$) δ 4.84 (p, J=6.2 Hz, 1H), 4.19 (p, J=6.5 Hz, 1H), 4.06-4.01 (m, 3H), 3.49 (t, J=7.8 Hz, 1H), 2.48 (dd, J=12.6, 6.8 Hz, 1H), 2.35 (dd, J=12.6, 5.0 Hz, 1H), 2.27-2.23 (m, 10H), 1.62-1.53 (m, 10H), 1.49-1.46 (m, 4H), 1.33-1.24 (m, 52H), 0.85 (t, J=6.8 Hz, 9H); $^{13}$C NMR (126 MHz, CDCl$_3$) δ 174.05, 173.72, 112.66, 74.44, 74.18, 69.08, 64.40, 62.65, 46.25, 37.82, 37.71, 37.49, 37.44, 34.83, 34.50, 34.26, 32.00, 31.97, 29.91, 29.86, 29.63, 29.61, 29.40, 29.37, 29.33, 29.27, 28.73, 26.04, 25.42, 25.26, 25.12, 24.06, 23.95, 23.73, 23.61, 22.77, 14.19; MS-ESI (m/z): 780.6 (M+H)$^+$.

Example 7 Synthesis of Compound 7

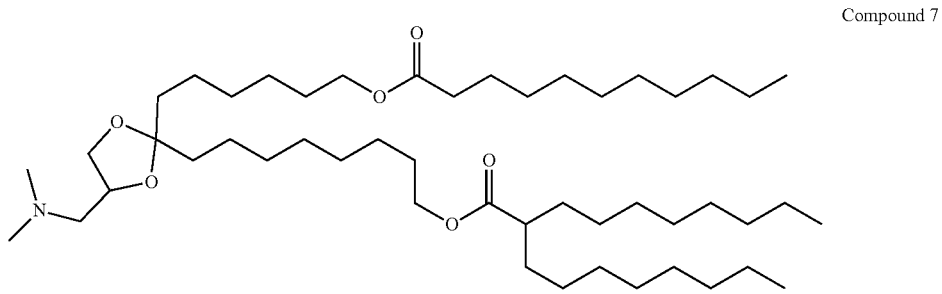 [SMILES: CCCCCCCCCCC(=O)OCCCCCCC1(CCCCCCCCOC(=O)C(CCCCCCCC)CCCCCCCC)OCC(CN(C)C)O1]

Compound 7

The method of preparation is the same as Compound 1, and 8-bromo-1-octanol, 2-octyl-decanoic acid and 3-dimethylamino-1,2-propanediol were used to replace Compound A1, Compound B1 and Compound K1 as raw materials to produce Compound 7 as an oil. $^1$H NMR (500 MHz, CDCl$_3$) δ 4.22-4.17 (m, 1H), 4.06-4.01 (m, 5H), 3.48 (t, J=7.8 Hz, 1H), 2.50-2.46 (m, 1H), 2.39-2.36 (m, 1H), 2.28-2.24 (m, 9H), 1.60-1.53 (m, 13H), 1.42-1.37 (m, 2H), 1.30-1.22 (m, 53H), 0.85 (t, J=6.8 Hz, 9H); $^{13}$C NMR (126 MHz, CDCl$_3$) δ 176.64, 173.92, 112.62, 74.26, 74.21, 68.96, 64.29, 64.10, 62.48, 46.07, 45.85, 37.75, 37.60, 37.42, 37.32, 34.40, 32.56, 31.90, 31.87, 29.91, 29.86, 29.57, 29.46, 29.31, 29.25, 29.18, 28.75, 28.64, 27.47, 25.99, 25.94, 25.03, 23.98, 23.85, 23.64, 23.51, 22.67, 14.10; MS-ESI (m/z): 794.6 (M+H)$^+$.

Example 8 Preparation of Compound 8

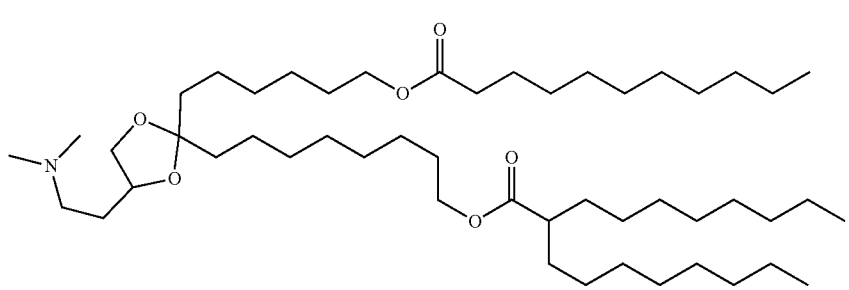

Compound 8

The method of preparation is the same as Compound 1, and 8-bromo-1-octanol, 2-octyl-decanoic acid and 1,2,4-butanetriol were used to replace Compound A1, Compound B1 and Compound K1 as raw materials to produce Compound 8 as an oil. $^1$H NMR (500 MHz, CDCl$_3$) δ 4.07-4.00 (m, 6H), 3.44 (t, J=7.5 Hz, 1H), 2.42-2.36 (brs 1H), 2.32-2.21 (m, 10H), 1.81-1.74 (brs, 1H), 1.68-1.51 (m, 14H), 1.42-1.34 (brs, 2H), 1.26-1.22 (m, 53H), 0.84 (t, J=6.9 Hz, 9H); $^{13}$C NMR (126 MHz, CDCl$_3$) δ 176.69, 173.97, 112.05, 74.81, 70.06, 64.36, 64.16, 56.36, 45.92, 45.50, 37.93, 37.78, 37.59, 37.48, 34.46, 32.63, 31.97, 31.94, 31.82, 29.63, 29.53, 29.37, 29.32, 29.24, 28.81, 28.71, 27.54, 26.06, 26.02, 25.09, 24.07, 23.94, 23.77, 23.64, 22.73, 14.16; MS-ESI (m/z): 808.6 (M+H)$^+$.

Example 9 Preparation of Compound 9

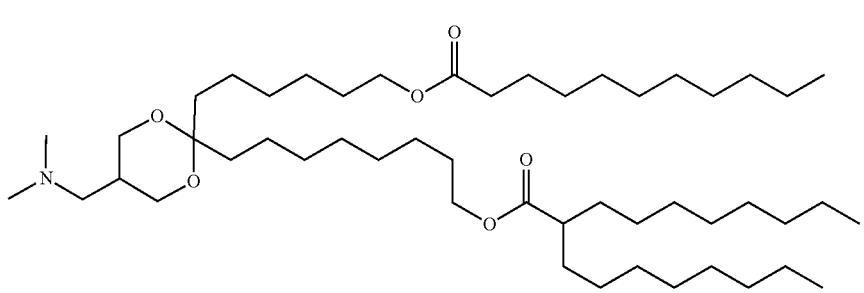

Compound 9

The method of preparation is the same as Compound 1, and 8-bromo-1-octanol, 2-octyl-decanoic acid, undecanoic acid and 6-bromo-1-hexanol were used to replace of Compound A1, Compound B1, Compound D1 and Compound E1 as raw materials to produce Compound 9 as an oil. $^1$H NMR (500 MHz, CDCl$_3$) δ 4.04-4.01 (m, 4H), 3.89-3.85 (m, 2H), 3.59-3.56 (m, 2H), 2.31-2.18 (m, 11H), 1.93-1.86 (brs, 1H), 1.67-1.52 (m, 12H), 1.43-1.23 (m, 56H), 0.85 (t, J=6.9 Hz, 9H); $^{13}$C NMR (126 MHz, CDCl$_3$) δ 176.71, 174.00, 100.75, 64.40, 64.36, 64.18, 62.83, 62.76, 59.34, 59.31F, 45.98, 45.94, 35.46, 35.25, 34.48, 32.64, 32.54, 32.46, 32.34, 31.98, 31.96, 30.06, 29.71, 29.65, 29.55, 29.39, 29.34, 29.26, 28.83, 28.74, 27.56, 26.08, 25.11, 23.46, 23.32, 23.23, 23.09, 22.75, 14.18; MS-ESI (m/z): 808.5 (M+H)$^+$.

Example 10 Preparation of Compound 10

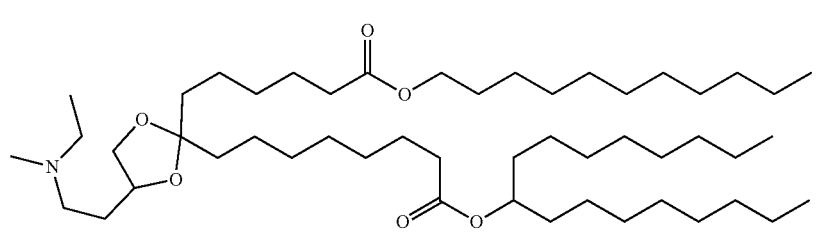

Compound 10

The method of preparation is the same as Compound 1, and 1,2,4-butanetriol and N—N-ethylmethylamine were used to replace Compound K1 and dimethylamine as raw materials to produce Compound 10 as an oil. $^1$H NMR (600 MHz, CDCl3) δ 4.83-4.75 (m, 1H), 4.05-3.93 (m, 4H), 3.42-3.35 (m, 1H), 2.46-2.30 (m, 4H), 2.23-2.15 (m, 7H), 1.79-1.70 (m, 1H), 1.67-1.59 (m, 1H), 1.56-1.51 (m, 6H), 1.43 (d, J=7.2 Hz, 4H), 1.29-1.14 (m, 56H), 0.99 (t, J=7.1 Hz, 3H), 0.80 (t, J=7.0 Hz, 9H); $^{13}$C NMR (151 MHz, CDCl$_3$) δ 173.72, 173.51, 111.83, 74.85, 74.81, 73.96, 69.99, 64.33, 53.70, 51.43, 41.49, 37.80, 37.56, 37.48, 37.28, 34.66, 34.26, 34.25, 34.15, 31.90, 31.85, 31.30, 29.77, 29.59, 29.57, 29.51, 29.49, 29.41, 29.38, 29.32, 29.29, 29.24, 29.22, 29.16, 29.13, 28.65, 25.92, 25.30, 25.13, 24.97, 23.96, 23.66, 23.31, 22.65, 14.08, 12.09; MS-ESI (m/z): 808.7 (M+H)$^+$.

Example 11 Preparation of Compound 11

Compound 11

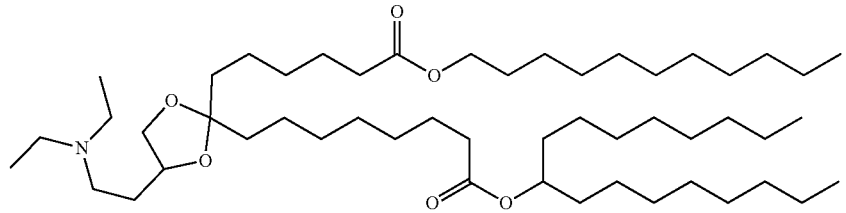

The method of preparation is the same as Compound 1, and 1,2,4-butanetriol and diethylamine were used to replace Compound K1 and dimethylamine as raw materials to produce Compound 11 as an oil. $^1$H NMR (600 MHz, CDCl3) δ 4.86-4.80 (m, 1H), 4.08-4.00 (m, 4H), 3.49-3.43 (m, 1H), 2.77-2.62 (m, 7H), 2.25 (dt, J=10.5, 7.5 Hz, 4H), 1.85-1.75 (m, 2H), 1.63-1.56 (m, 6H), 1.50-1.44 (m, 4H), 1.37-1.19 (m, 56H), 1.12 (t, J=7.2 Hz, 6H), 0.85 (td, J=7.1, 2.4 Hz, 9H); $^{13}$C NMR (151 MHz, CDCl$_3$) δ 173.95, 173.73, 112.22, 74.59, 74.55, 74.17, 69.94, 64.52, 49.36, 46.95, 37.84, 37.59, 37.42, 37.21, 34.80, 34.39, 34.24, 31.99, 31.95, 30.30, 29.87, 29.69, 29.67, 29.62, 29.59, 29.50, 29.47, 29.42, 29.35, 29.32, 29.29, 29.26, 28.74, 26.02, 25.40, 25.24, 25.07, 24.09, 23.82, 23.76, 23.47, 22.75, 14.20, 10.74; MS-ESI (m/z): 822.9 (M+H)$^+$.

Example 12 Preparation of Compound 12

Compound 12

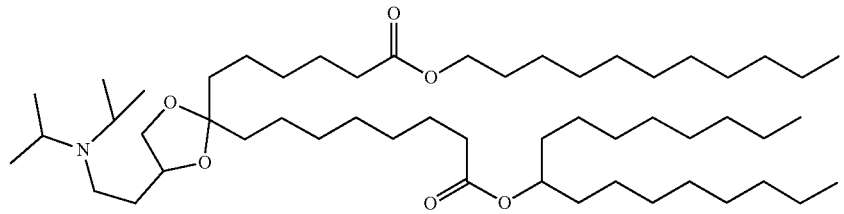

The preparation of Compound 12 is referred to the preparation of Compound 2.

Example 13 Preparation of Compound 13

Compound 13

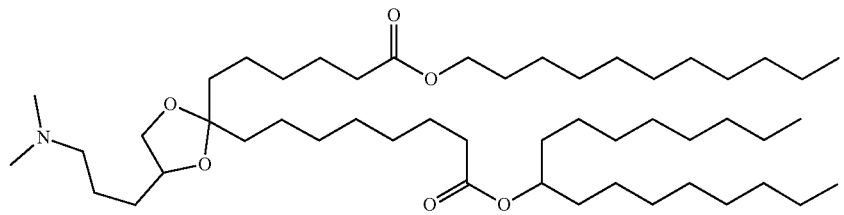

The method of preparation is the same as Compound 1, and 1,2,5-pentanetriol was used to replace Compound K1 as raw material to produce Compound 13 as an oil. $^1$H NMR (600 MHz, CDCl$_3$) δ 4.81-4.74 (m, 1H), 4.00-3.92 (m, 4H), 3.38-3.33 (m, 1H), 2.25-2.17 (m, 6H), 2.15 (s, 6H), 1.59-1.46 (m, 15H), 1.46-1.37 (m, 5H), 1.29-1.12 (m, 50H), 0.79 (td, J=7.1, 2.3 Hz, 9H); $^{13}$C NMR (151 MHz, CDCl$_3$) δ 173.69, 173.47, 111.86, 76.08, 76.05, 73.92, 69.93, 69.91, F64.29, 59.48, 53.38, 45.24, 37.80, 37.56, 37.47, 37.25, 34.64, 34.24, 34.22, 34.13, 31.88, 31.83, 31.20, 29.76, 29.57, 29.55, 29.49, 29.47, 29.39, 29.37, 29.30, 29.27, 29.22, 29.20, 29.14, 29.11, 28.63, 25.90, 25.28, 25.12, 24.95, 23.95, 23.89, 23.64, 23.62, 23.29, 22.64, 22.62, 14.05; MS-ESI (m/z): 808.8 (M+H)$^+$.

Example 14 Preparation of Compound 14

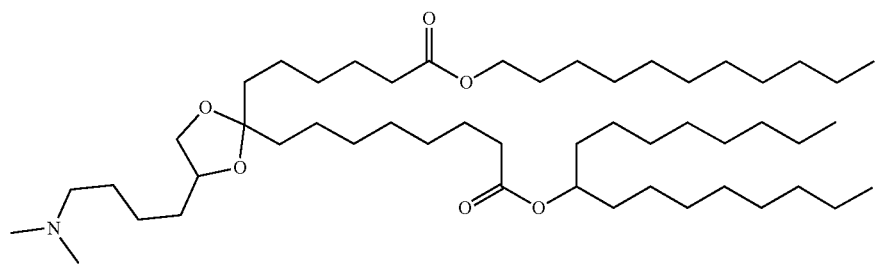 [SMILES: CCCCCCCCCCCOC(=O)CCCCCC1(CCCCCCCC(=O)OC(CCCCCCCC)CCCCCCCC)OCC(CCCCN(C)C)O1]

The method of preparation is the same as Compound 1, and 1,2,6-hexanetriol was used to replace Compound K1 as raw material to produce Compound 14 as an oil. $^1$H NMR (600 MHz, CDCl$_3$) δ 4.91-4.79 (m, 1H), 4.02 (m, 4H), 3.45-3.34 (m, 1H), 2.33 (t, J=6.5 Hz, 2H), 2.27 (m, 10H), 1.60 (m, 9H), 1.53-1.41 (m, 8H), 1.25 (m, 55H), 0.87 (t, J=7.0 Hz, 9H); $^{13}$C NMR (151 MHz, Chloroform-d) δ 111.89, 76.18, 74.09, 70.03, 64.42, 59.48, 45.20, 37.94-37.16 (m), 34.73, 34.33, 34.15, 33.31, 31.88, 29.81, 29.59, 29.51, 29.44, 29.32, 29.24, 28.66, 27.37, 25.92, 25.31, 25.16, 24.99, 23.68, 22.66, 14.09; MS-ESI (m/z): 822.9 (M+H)$^+$.

Example 15 Preparation of Compound 15

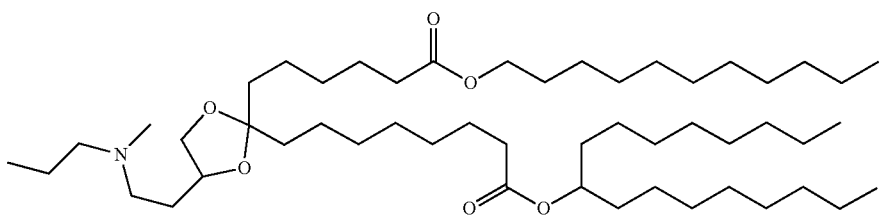 [SMILES: CCCCCCCCCCCOC(=O)CCCCCC1(CCCCCCCC(=O)OC(CCCCCCCC)CCCCCCCC)OCC(CCN(C)CCC)O1]

The method of preparation is the same as Compound 1, and 1,2,4-butanetriol and N-methyl-n-propylamine were used to replace Compound K1 and dimethylamine as raw materials to produce Compound 15 as an oil. $^1$H NMR (600 MHz, CDCl$_3$) δ 4.84-4.78 (m, 1H), 4.07-3.97 (m, 4H), 3.42 (t, J=7.7 Hz, 1H), 2.53-2.39 (m, 2H), 2.33 (t, J=7.6 Hz, 2H), 2.26-2.20 (m, 7H), 1.81-1.74 (m, 1H), 1.74-1.66 (m, 1H), 1.61-1.54 (m, 6H), 1.51-1.41 (m, 5H), 1.35-1.14 (m, 55H), 0.84 (dt, J=15.0, 7.3 Hz, 12H).; $^{13}$C NMR (151 MHz, CDCl$_3$) δ 173.86, 173.64, 111.97, 74.82, 74.78, 74.09, 70.02, 64.45, 59.66, 54.18, 41.99, 37.87, 37.62, 37.52, 37.32, 34.76, 34.35, 34.22, 31.97, 31.92, 31.06, 29.85, 29.83, 29.64, 29.58, 29.56, 29.49, 29.46, 29.39, 29.31, 29.29, 29.25, 29.22, 28.72, 25.99, 25.37, 25.21, 25.04, 24.05, 23.75, 23.72, 23.41, 22.73, 22.71, 20.09, 14.15, 11.84; MS-ESI (m/z): 822.8 (M+H)$^+$.

Example 16 Preparation of Compound 16
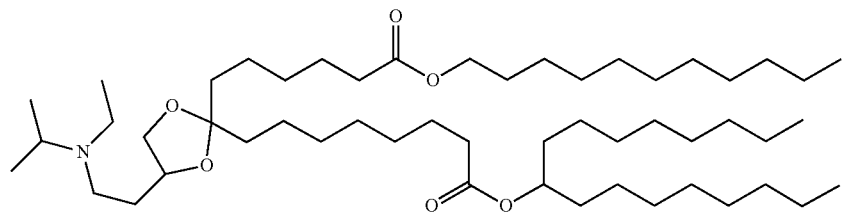 [SMILES: CCCCCCCCCCCOC(=O)CCCCCC1(CCCCCCCC(=O)OC(CCCCCCCC)CCCCCCCC)OCC(CCN(CC)C(C)C)O1]
The method of preparation is the same as Compound 1, and 1,2,4-butanetriol and N—N-ethylisopropylamine were used to replace Compound K1 and dimethylamine as raw materials to produce Compound 16 as an oil. $^1$H NMR (600 MHz, CDCl$_3$) δ 4.84 (p, J=6.3 Hz, 1H), 4.11-4.01 (m, 4H), 3.47 (t, J=7.6 Hz, 1H), 3.34-2.50 (m, 5H), 2.29-2.22 (m, 4H), 1.64-1.44 (m, 14H), 1.40-1.03 (m, 63H), 0.86 (t, 9H); $^{13}$C NMR (151 MHz, CDCl$_3$) δ 173.95, 173.73, 112.18, 74.58, 74.19, 69.97, 64.54, 46.37, 44.49, 37.86, 37.61, 37.44, 37.23, 34.82, 34.41, 34.25, 32.01, 31.97, 29.90, 29.87, 29.80, 29.70, 29.68, 29.63, 29.60, 29.50, 29.43, 29.36, 29.33, 29.28, 28.76, 26.03, 25.42, 25.25, 25.10, 25.08, 24.12, 23.85, 23.79, 23.50, 22.78, 22.76, 18.33, 17.19, 14.20; MS-ESI (m/z): 836.8 (M+H)$^+$
Example 17 Preparation of Compound 17
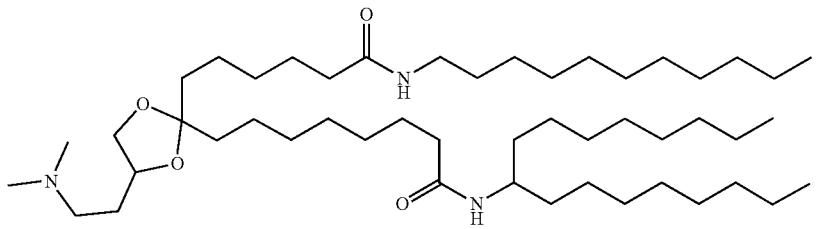 [SMILES: CCCCCCCCCCCNC(=O)CCCCCC1(CCCCCCCC(=O)NC(CCCCCCCC)CCCCCCCC)OCC(CCN(C)C)O1]
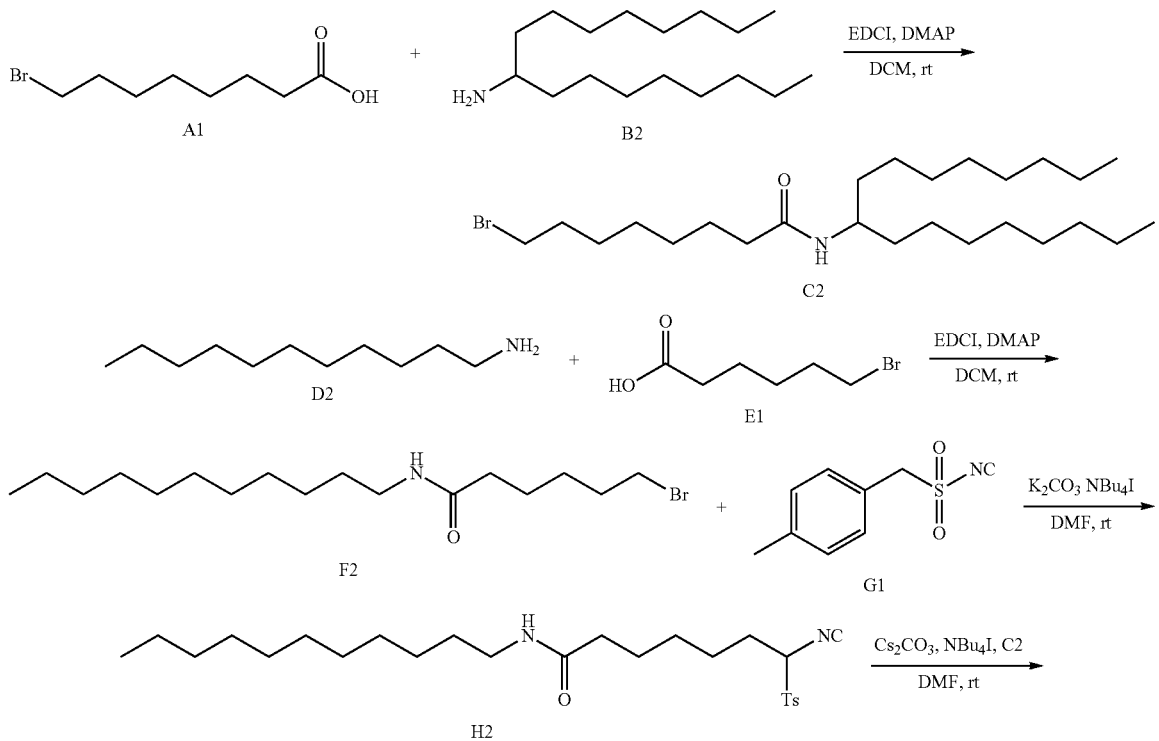

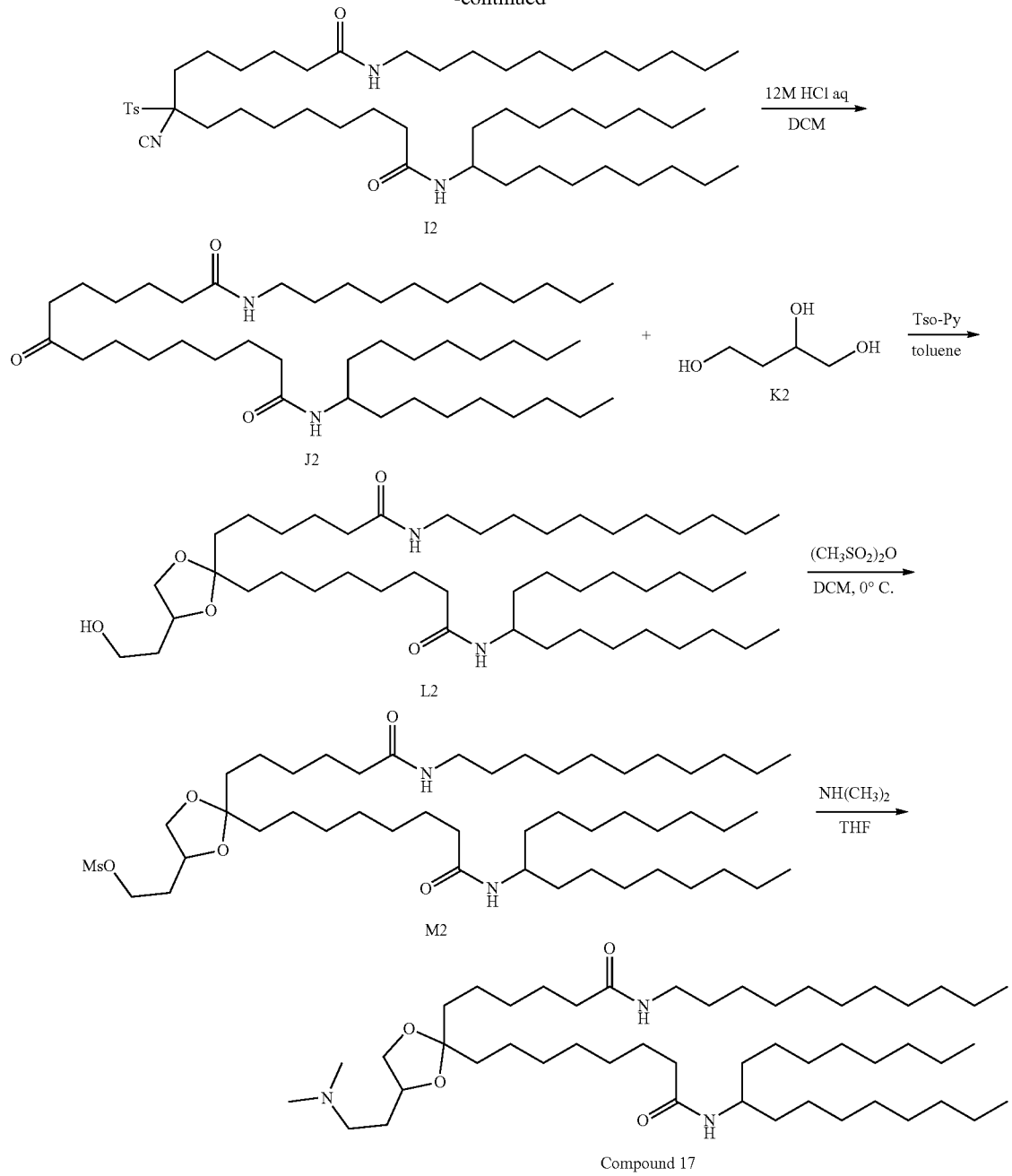

Specifically, To a solution of Compound A1 (5.24 g, 23.49 mmol) in dichloromethane (30 ml) were added Compound B2 (5.0 g, 19.57 mmol), EDCI (4.9 g, 25.44 mmol) and DMAP (0.96, 7.83 mmol), and the reaction mixture was stirred for 7 hours at room temperature and monitored by TLC. After completion of the reaction, the reaction mixture was diluted by adding an equal volume of saturated sodium bicarbonate solution, and separated. The organic layer was dried over anhydrous magnesium sulfate, and filtered. The filtrate was concentrated, and purified on silica gel column chromatography (petroleum ether:ethyl acetate=30:1) to obtain Compound C2 (7.19 g, 80.00%).

To a solution of Compound D2 (7.0 g, 40.8 mmol) in dichloromethane (60 ml) were added Compound E1 (9.6 g, 49.0 mmol), EDCI (10.2 g, 53.1 mmol) and DMAP (2.0 g, 16.4 mmol), and the reaction mixture was stirred for 7 hours at room temperature and monitored by TLC. After completion of the reaction, the reaction mixture was diluted by adding an equal volume of saturated sodium bicarbonate solution, and separated. The organic layer was dried over anhydrous magnesium sulfate, and filtered. The filtrate was concentrated, and purified on silica gel column chromatography (petroleum ether:ethyl acetate=30:1) to obtain Compound F2 (12.20 g, 86.15%).

To a solution of Compound F2 (12.2, 35.14 mmol) in DMF (50 ml) were added Compound G1 (13.72 g, 70.28 mmol), NBu$_4$I (13.0 g, 35.14 mmol) and K2CO3 (14.57 g, 105.43 mmol), and the reaction mixture was stirred for 12 hours at room temperature and monitored by TLC. After completion of the reaction, the reaction mixture was diluted by adding an equal volume of water, extracted with ethyl acetate (50 ml×3), concentrated, and purified on silica gel column chromatography (petroleum ether:ethyl acetate=3:1) to obtain Compound H2 (9.9 g, 61.11% yield).

To a solution of Compound H2 (9.9 g, 21.42 mmol) in DMF (100 ml) were added Compound C2 (11.19 g, 33.12 mmol), NBu$_4$I (8.0 g, 21.24 mmol) and Cs2CO3 (14 g, 42.84 mmol), and the reaction mixture was stirred for 15 hours at room temperature and monitored by TLC. After completion of the reaction, the reaction mixture was diluted by adding an equal volume of water, extracted with ethyl acetate (100 ml×3), concentrated, and purified on silica gel column chromatography (petroleum ether:ethyl acetate=3:1) to obtain Compound 12 (12 g, 66.67% yield).

To a solution of Compound 12 (12 g, 14.26 mmol) in dichloromethane (100 ml) was added concentrated hydrochloric acid (60 ml), and the reaction mixture was stirred for 3 hours at room temperature and monitored by TLC. After completion of the reaction, the layers were separated. The organic layer was washed with saturated sodium bicarbonate solution, dried over anhydrous magnesium sulfate, concentrated, and purified on silica gel column chromatography (petroleum ether:ethyl acetate=1:1) to obtain Compound G2 (7.72 g, 80.00%).

To a solution of Compound G2 (3 g, 4.44 mmol) in toluene (25 ml) were added Compound K2 (1.42 g, 13.32 mmol) and pyridinium 4-methylbenzenesulfonate (1.34 g, 6.65 mmol), and the reaction mixture was heated to reflux for 20 h with Dean-Stark apparatus, and monitored by TLC. After completion of the reaction, the reaction mixture was cooled to room temperature, diluted by adding an equal volume of water, extracted with ethyl acetate (50 ml×3), concentrated, and purified on silica gel column chromatography (dichloromethane:methanol=40:1) to obtain Compound L2 (1.3 g, 43.33% yield).

To a solution of Compound L2 (1.3 g, 1.7 mmol) in ultra dry dichloromethane (10 ml) were added methanesulfonic anhydride (0.59 g, 3.4 mmol) and anhydrous triethylamine (0.7 ml) at 0° C., and the reaction mixture was stirred for 12 hours, and monitored by TLC. After completion of the reaction, the reaction solution is cooled to room temperature, diluted by adding an equal volume of water, and separated. The organic layer was dried over anhydrous magnesium sulfate, and filtered. The filtrate was concentrated, and purified on silica gel column chromatography (dichloromethane:methanol=40:1) to obtain Compound M2 (1.32 g, 92.30% yield).

To Compound M2 (1.32 g, 1.57 mmol) was added a solution of 30 ml dimethylamine (2M in THF), and the reaction mixture was sealed, stirred at room temperature for 6 days, and monitored by TLC. After completion of the reaction, concentrated, and purified on silica gel column chromatography (dichloromethane:methanol=30:1+ ammonia water) to obtain Compound 17 as an oil (300 mg, yield 24%). $^1$H NMR (500 MHz, Chloroform-d) δ 5.84-5.69 (m, 1H), 5.34 (t, J=9.1 Hz, 1H), 4.05-3.96 (m, 2H), 3.88-3.79 (m, 1H), 3.41 (t, J=7.4 Hz, 1H), 3.16 (q, J=6.7 Hz, 2H), 2.44-2.33 (m, 1H), 2.29-2.22 (m, 1H), 2.19 (d, J=3.3 Hz, 6H), 2.09 (t, J=7.6 Hz, 4H), 1.79-1.69 (m, 1H), 1.66-1.47 (m, 8H), 1.45-1.37 (m, 3H), 1.30-1.17 (m, 56H), 0.82 (t, J=6.9, 2.4 Hz, 9H); $^{13}$C NMR (126 MHz, CDCl$_3$) δ 172.97, 172.62, 111.98, 111.94, 74.72, 74.68, 69.97, 56.31, 49.09, 45.48, 45.45, 39.53, 37.71, 37.49, 37.38, 37.25, 37.11, 36.74, 36.72, 35.33, 31.93, 31.90, 31.75, 29.73, 29.63, 29.59, 29.48, 29.36, 29.30, 29.24, 26.99, 25.99, 25.94, 25.80, 25.76, 23.92, 23.77, 23.60, 23.40, 22.69, 14.14; MS-ESI (m/z): 792.9 (M+H)+

Example 18 Compound 18

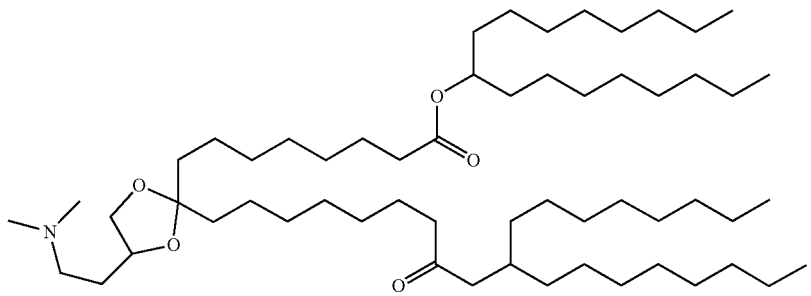 [SMILES: CCCCCCCCC(CCCCCCCC)CC(=O)CCCCCCCC1(CCCCCCCC(=O)OC(CCCCCCCC)CCCCCCCC)OCC(CCN(C)C)O1]

The synthetic route is shown below:

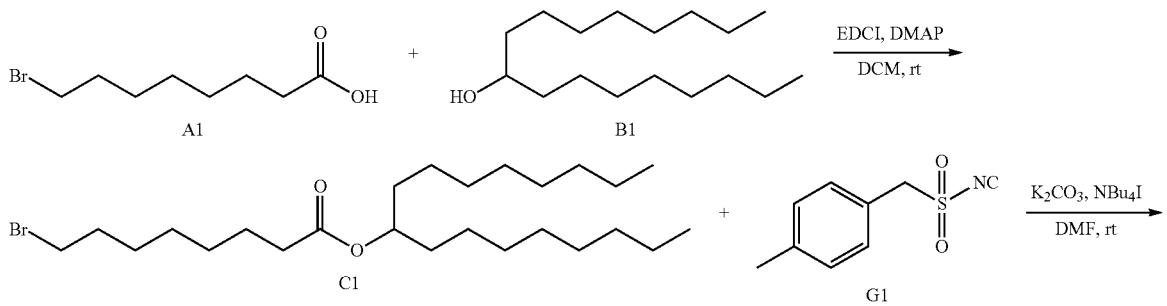

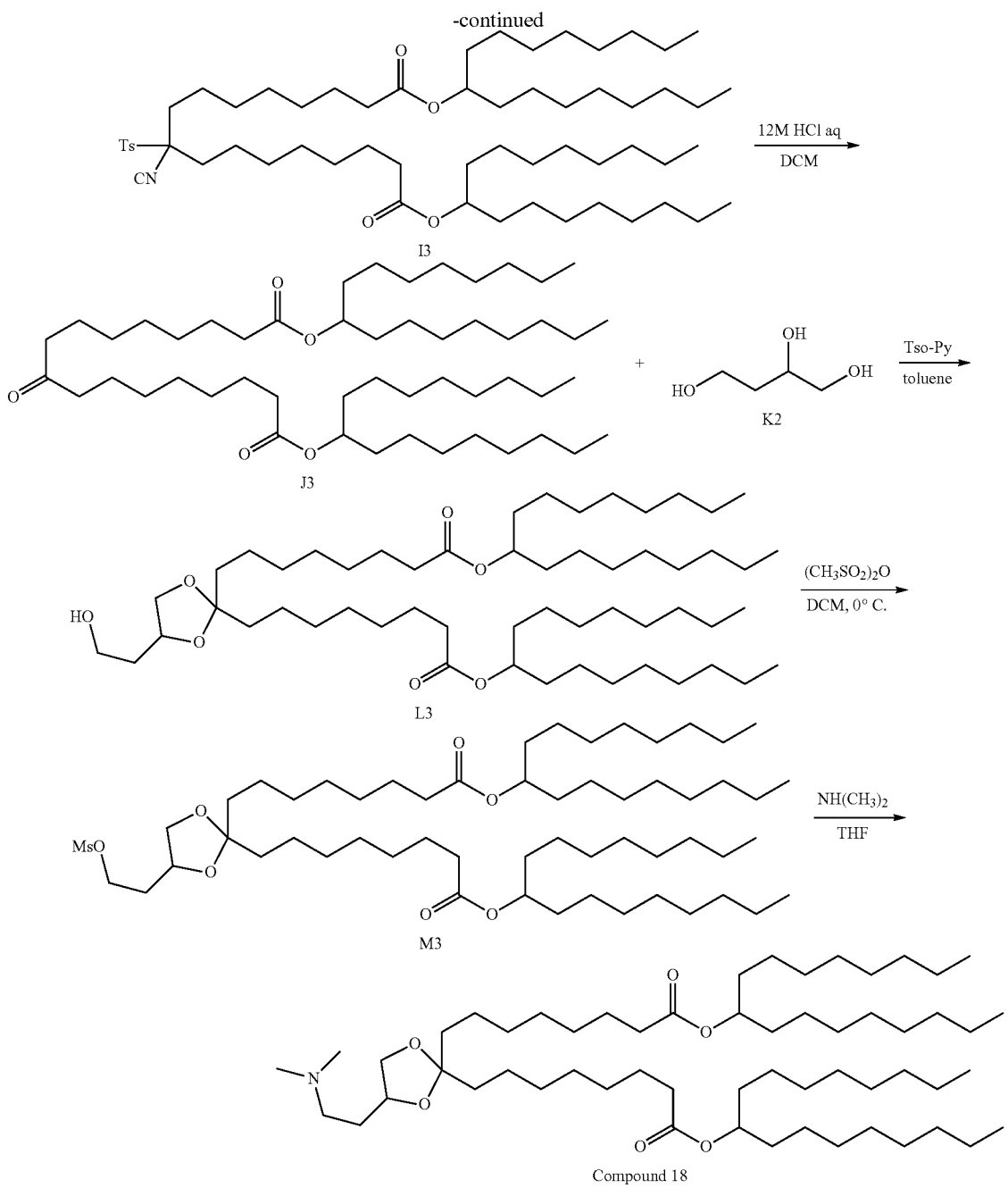

Specifically, to a solution of Compound A1 (10.40 g, 46.82 mmol) in dichloromethane (100 ml) were added Compound B1 (10 g, 39.02 mmol), EDCI (14.96 g, 78.04 mmol) and DMAP (1.90 g, 15.61 mmol), and the reaction mixture was stirred for 7 hours at room temperature and monitored by TLC. After completion of the reaction, the reaction mixture was diluted by adding an equal volume of saturated sodium bicarbonate solution, and separated. The organic layer was dried over anhydrous magnesium sulfate, and filtered. The filtrate was concentrated, and purified on silica gel column chromatography (petroleum ether:ethyl acetate=30:1) to obtain Compound C1 (15 g, 83.52%).

To a solution of Compound C1 (15 g, 32.60 mmol) in DMF (100 ml) were added Compound G1 (2.12 g, 10.86 mmol), NBu₄I (4 g, 10.86 mmol) and Cs2CO3 (10.62 g, 32.6 mmol), and the reaction mixture was stirred for 12 hours at room temperature and monitored by TLC. After completion of the reaction, the reaction mixture was diluted by adding an equal volume of water, extracted with ethyl acetate (100 ml×3), concentrated, and purified on silica gel column chromatography (petroleum ether:ethyl acetate=40:1) to obtain Compound 13 (7.95 g, 76.60% yield).

To a solution of Compound 13 (7.95 g, 8.31 mmol) in dichloromethane (100 ml) was added concentrated hydrochloric acid (60 ml), and the reaction mixture was stirred for 3 hours at room temperature and monitored by TLC. After completion of the reaction, the layers were separated. The organic layer was washed with saturated sodium bicarbonate solution, dried over anhydrous magnesium sulfate, concentrated, and purified on silica gel column chromatography (petroleum ether:ethyl acetate=50:1) to obtain Compound J3 (5.89 g, 89.65%).

To a solution of Compound J3 (5.89 g, 7.45 mmol) in toluene (25 ml) were added Compound K2 (2.4 g, 22.35 mmol) and pyridinium 4-methylbenzenesulfonate (2.95 g, 11.73 mmol), and the reaction mixture was heated to reflux for 20 h with Dean-Stark apparatus, and monitored by TLC. After completion of the reaction, the reaction mixture was cooled to room temperature, diluted by adding an equal volume of water, extracted with ethyl acetate (50 ml×3), concentrated, and purified on silica gel column chromatography (petroleum ether:ethyl acetate=5:1) to obtain Compound L3 (2.94 g, 44.95% yield).

To a solution of Compound L3 (2.94 g, 3.34 mmol) in ultra dry dichloromethane (10 ml) were added methanesulfonic anhydride (1.2 g, 6.68 mmol) and anhydrous triethylamine (0.8 ml) at 0° C., and the reaction mixture was stirred for 12 hours, and monitored by TLC. After completion of the reaction, the reaction solution is cooled to room temperature, diluted by adding an equal volume of water, and separated. The organic layer was dried over anhydrous magnesium sulfate, and filtered. The filtrate was concentrated, and purified on silica gel column chromatography (petroleum ether:ethyl acetate=5:1) to obtain Compound M3 (3.1 g, 97% yield).

To Compound M3 (3.1 g, 3.24 mmol) was added a solution of 30 ml dimethylamine (2M in THF), and the reaction mixture was sealed, stirred at room temperature for 6 days, and monitored by TLC. After completion of the reaction, concentrated, and purified on silica gel column chromatography (dichloromethane:methanol=40:1) to obtain Compound 18 as an oil (439 mg, 14.98% yield). 1H NMR (500 MHz, CDCl3) δ 4.87-4.79 (m, 2H), 4.08-3.98 (m, 2H), 3.44 (t, J=7.4 Hz, 1H), 2.46-2.37 (m, 1H), 2.36-2.27 (m, 1H), 2.22 (t, J=6.7 Hz, 10H), 1.83-1.74 (m, 1H), 1.72-1.62 (m, 1H), 1.58-1.51 (m, 3H), 1.46 (d, J=6.1 Hz, 8H), 1.36-1.14 (m, 69H), 0.84 (t, J=6.9 Hz, 12H); $^{13}$C NMR (126 MHz, CDCl$_3$) δ 173.69, 112.11, 74.73, 74.10, 70.02, 56.33, 45.42, 37.85, 37.53, 34.78, 34.23, 31.94, 31.70, 29.87, 29.60, 29.31, 29.27, 29.24, 25.39, 25.23, 24.05, 23.75, 22.74, 14.18; MS-ESI (m/z): 906.9 (M+H)$^+$.

Example 19 Compound 19

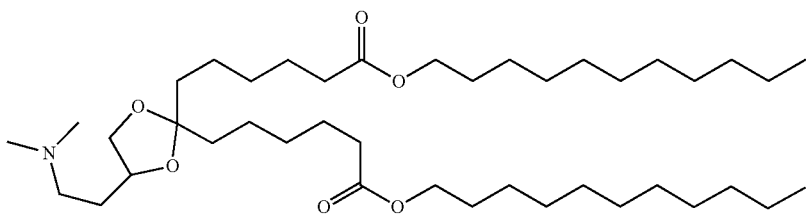 [SMILES: CCCCCCCCCCCOC(=O)CCCCCC1(CCCCCC(=O)OCCCCCCCCCCC)OCC(CCN(C)C)O1]

The method of preparation is the same as Compound 18, and 6-bromohexanoic acid and undecanol were used to replace Compound A1 and Compound B1 as raw materials to produce Compound 19 as an oil. $^1$H NMR (500 MHz, CDCl3) δ 4.08-3.98 (m, 6H), 3.44 (t, J=7.4 Hz, 1H), 2.46-2.38 (m, 1H), 2.37-2.29 (m, 1H), 2.29-2.20 (m, 10H), 1.83-1.74 (m, 1H), 1.72-1.65 (m, 1H), 1.61-1.52 (m, 11H), 1.29-1.22 (m, 41H), 0.85 (t, J=6.9 Hz, 6H); $^{13}$C NMR (126 MHz, CDCl$_3$) δ 173.94, 111.93, 74.78, 70.07, 64.50, 56.33, 45.44, 37.67, 37.39, 34.39, 31.99, 31.67, 29.68, 29.61, 29.50, 29.42, 29.34, 28.74, 26.01, 25.06, 23.75, 23.42, 22.77, 14.21; MS-ESI (m/z): 628.6 (M+H)+

Example 20A Compound 20A

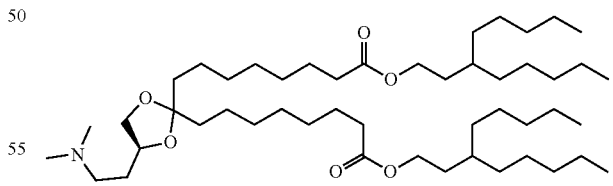

The synthetic route is shown below:

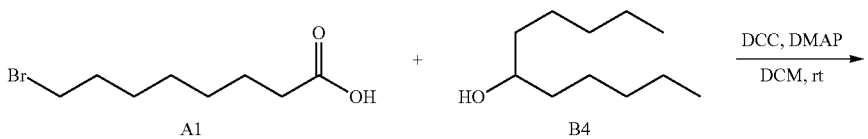

-continued
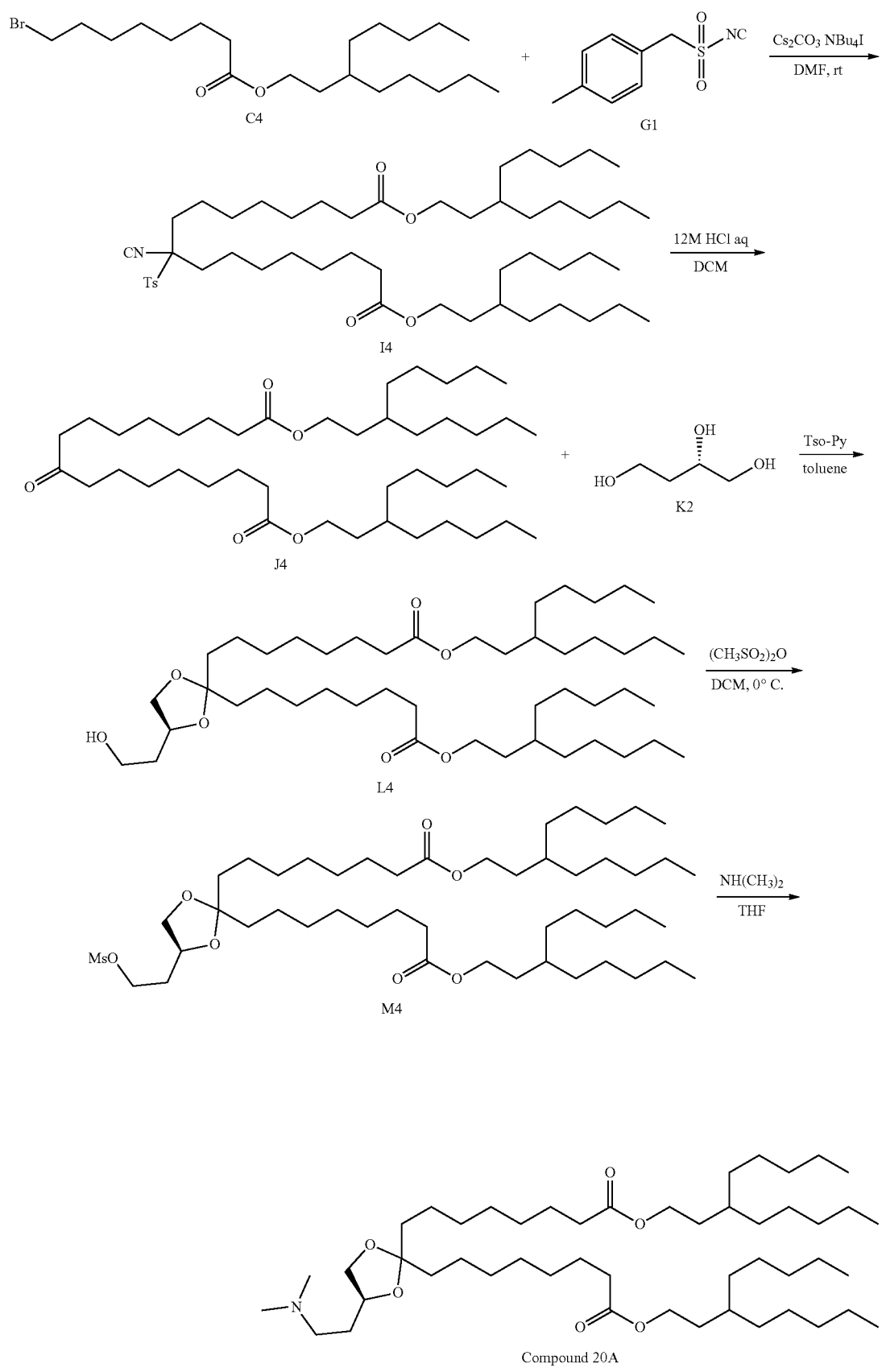

Specifically, to a solution of Compound A1 (0.28 g, 1.25 mmol) in dichloromethane (30 ml) were added Compound B4 (0.25 g, 1.25 mmol), DCC (0.28 g, 1.38 mmol) and DMAP (0.01 g, 0.06 mmol), and the reaction mixture was stirred for 2 hours at room temperature and monitored by TLC. After completion of the reaction, the reaction mixture was diluted by adding an equal volume of saturated sodium bicarbonate solution, and separated. The organic layer was dried by adding anhydrous sodium sulfate, and filtered. The filtrate was concentrated, and purified on silica gel column chromatography (petroleum ether:ethyl acetate=30:1) to obtain Compound C4 (0.50 g, 88.90%).

To a solution of Compound C4 (0.50 g, 1.23 mmol) in DMF (5 ml) were added Compound G1 (0.12 g, 0.62 mmol), NBu$_4$I (0.05 g, 0.12 mmol) and Cs2CO3 (1.21 g, 3.71 mmol), and the reaction mixture was stirred for 12 hours at room temperature and monitored by TLC. After completion of the reaction, the reaction mixture was diluted by adding an equal volume of water, extracted with ethyl acetate (10 ml×3), concentrated, to obtain the crude Compound 14, which was used directly in the next step of feeding.

To a solution of Compound 14 (crude, 1.23 mmol) in dichloromethane (10 ml) was added concentrated hydrochloric acid (5 ml), and the reaction mixture was stirred for 3 hours at room temperature and monitored by TLC. After completion of the reaction, the layers were separated. The organic layer was washed with saturated sodium bicarbonate solution, dried over anhydrous sodium sulfate, concentrated, and purified on silica gel column chromatography (petroleum ether:ethyl acetate=30:1) to obtain Compound J4 (0.27 g, 32.27% yield over two steps).

To a solution of Compound J4 (0.27 g, 0.40 mmol) in toluene (25 ml) were added Compound K2 (0.17 g, 1.59 mmol) and pyridinium 4-methylbenzenesulfonate (0.10 g, 0.02 mmol), and the reaction was heated to reflux for 20 h with Dean-Stark apparatus, and monitored by TLC. After completion of the reaction, the reaction mixture was cooled to room temperature, diluted by adding an equal volume of water, extracted with ethyl acetate (10 ml×3), concentrated, and purified on silica gel column chromatography (petroleum ether:ethyl acetate=5:1) to obtain Compound L4 (0.28 g, 91.79% yield).

To a solution of Compound L4 (0.28 g, 0.36 mmol) in dichloromethane (10 ml) were added methanesulfonic anhydride (0.10 g, 0.55 mmol) and anhydrous triethylamine (0.20 ml), and the reaction was stirred for 2 hours at room temperature, and monitored by TLC. After completion of the reaction, the reaction solution is cooled to room temperature, diluted by adding an equal volume of water, and separated. The organic layer was dried by adding anhydrous sodium sulfat, and filtered. The filtrate was concentrated to obtain the crude compound M4, which was directly used for the next step of feeding.

To Compound M4 (crude, 0.36 mmol) was added a solution of 20 ml dimethylamine (2M in THF) under the protection of nitrogen, and the reaction mixture was stirred at room temperature for 3 days, and monitored by TLC. After completion of the reaction, concentrated, and purified on silica gel column chromatography (dichloromethane:methanol=30:1) to obtain Compound 20A as an oil (0.21 g, 66.50% yield over two steps). 1H NMR (400 MHz, CDCl3) δ 4.20-4.09 (m, 6H), 3.55 (t, J=8.0 Hz, 1H), 2.87-2.69 (m, 2H), 2.55 (s, 6H), 2.32 (t, J=8.0 Hz, 4H), 1.94-1.87 (m, 2H), 1.68-1.56 (m, 12H), 1.36-1.21 (m, 50H), 0.92 (t, J=8.0 Hz, 9H); 13C NMR (400 MHz, CDCl3) δ 173.96, 112.52, 73.98, 69.66, 62.94, 55.97, 44.30, 37.66, 37.17, 34.63, 34.42, 33.57, 32.49, 32.23, 29.73 29.71, 29.27, 29.14, 26.21, 24.98, 23.97, 23.71, 22.66, 14.09; MS-ESI (m/z): 795.0 (M+H)$^+$.

Example 21 Compound 21

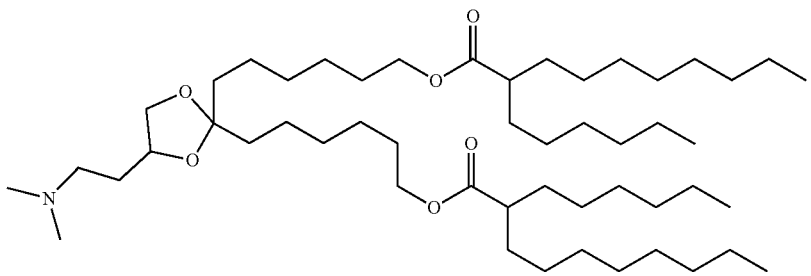 [SMILES: CCCCCCCCC(CCCCCC)C(=O)OCCCCCCC1(CCCCCCOC(=O)C(CCCCCC)CCCCCCCC)OCC(CCN(C)C)O1]

The method of preparation is the same as compound 18, and 6-bromohexanol and 2-hexyl decanoic acid were used to replace Compound A1 and Compound B1 as raw materials to produce Compound 21 as an oil. $^1$H NMR (600 MHz, Chloroform-d) δ 4.11-4.02 (m, 6H), 3.47 (t, J=7.6 Hz, 1H), 2.47-2.41 (brs, 1H), 2.37-2.33 (brs, 1H), 2.32-2.24 (m, 8H), 1.84-1.78 (brs, 1H), 1.72-1.65 (brs, 1H), 1.63-1.54 (m, 12H), 1.45-1.40 (m, 4H), 1.37-1.31 (m, 10H), 1.30-1.21 (m, 42H), 0.87 (td, J=7.0, 1.3 Hz, 12H); $^{13}$C NMR (600 MHz, Chloroform-d) δ 176.70, 111.95, 74.72, 69.98, 64.08, 56.24, 45.84, 45.34, 37.75, 37.43, 32.52, 31.85, 31.69, 31.62, 29.56, 29.44, 29.24, 29.22, 28.69, 27.46, 27.41, 25.99, 23.90, 23.60, 22.66, 22.58, 14.07; MS-ESI (m/z): 823.0 (M+H)$^+$.

TEST EXAMPLES

Experimental Example 1: Lipid Nanoparticle (LNP) Encapsulation

The mRNA stock solution was dispersed in 20 mM acetic acid solution (pH 5.0) to give a final concentration of 200 μg/mL (aqueous phase). Mixing was carried out by dissolving a mixture according to the molar ratio of Compound:cholesterol:DSPC:DMG-PEG2000=50:38.5:10:1.5 as shown in Table 1 with anhydrous ethanol to form a mixed lipid (oil phase). The mRNA was mixed with the lipid mixture by T-mixing and controlling the flow rate of aqueous phase and oil phase (3:1) with a total flow rate of 12-50 ml/min, to obtain LNP-encapsulated mRNA. The encapsulated LNP was diluted with buffer (pH 5.0-5.5) and then concentrated by ultrafiltration with replacement of diluent, and finally LNP was concentrated to 200 μg/mL~600 μg/mL of mRNA, while the pH of LNP was adjusted to about 7-8. Finally, Quant-iT™ RiboGreen™ RNA Assay Kit (Invirtogen by Thermo Fisher Scientific, cat #R11490), and 10% Triton X-100 solution or 10% OTG solution as an emulsion breaker were used to detect the total and free content of mRNA in the LNP, and the encapsulation efficiency of LNP was calculated. The final product of LNP was diluted with a diluent, then 1 ml was added to a particle size cell, and placed on the Malvern ZetaSizer instrument to detect the particle size of LNP, and the results are shown in Table 1.

TABLE 1

Characterization data of LNP of the compounds of the Examples

| Serial Number | Particle Size (nm) | PDI | Encapsulation Efficiency |
|---|---|---|---|
| Example 1 | 66.97 | 0.1125 | 97.22% |
| Example 2 | 70.27 | 0.03414 | 92.32% |
| Example 2A | 86.26 | 0.02967 | 96.44% |
| Example 3 | 95.04 | 0.1264 | 95.04% |
| Example 4 | 69.03 | 0.1387 | 96.23% |
| Example 5 | 89.54 | 0.04107 | 94.92% |
| Example 5A | 73.41 | 0.1311 | 96.0% |
| Example 5B | 67.95 | 0.04848 | 98.4% |
| Example 6 | 69.85 | 0.1676 | 95.50% |
| Example 7 | 92.38 | 0.1537 | 96.52% |
| Example 8 | 99.68 | 0.09334 | 90.99% |
| Example 9 | 71.61 | 0.1368 | 95.07% |
| Example 10 | 78.44 | 0.07 | 96.5% |
| Example 11 | 80.34 | 0.06 | 97.5% |
| Example 13 | 98.15 | 0.16 | 89.3% |
| Example 14 | 118.1 | 0.16 | 90.97% |
| Example 15 | 61.73 | 0.10 | 97.2% |
| Example 16 | 71.68 | 0.03 | 97.6% |
| Example 17 | 125.0 | 0.05 | 98.2% |
| Example 18 | 69.23 | 0.10 | 96.5% |
| Example 19 | 110.3 | 0.34 | 93.3% |
| Example 20A | 85.64 | 0.073 | 92.5% |
| Example 21 | 92.89 | 0.3138 | 96.8% |
| MC3 | 72.70 | 0.15 | 96.7% |
| SM-102 | 74.80 | 0.07 | 97.5% |

Experimental Example 2: Toxicity Assay

The nanoparticle samples containing different lipids were administered to rats (SD rats, Zhejiang Vital River Laboratory Animal Technology Co., Ltd, 3 males and 3 females per group, body weight: 220-300 g for female, 260-340 g for male) by intravenous injection at a dose of 3 mg/kg. The expression of various clinical markers was assessed at 24 hours after administration and compared with the expression induced by SM102 LNP formulation (i.e., LNP formulation made from the known SM102 lipid, which was prepared according to the method of Test Example 1 in the same ratio) as well as by phosphate buffered saline (PBS).

TABLE 2

| Test Sample | Alanine transaminase (U/L) | Aspartate transaminase (U/L) |
|---|---|---|
| PBS | 43.72 | 139.42 |
| SM102 | 286.51 | 486.42 |
| Compound 2 | 116.27 | 342.17 |
| Compound 5 | 65.72 | 251.10 |

The results as shown in Table 2, showed that the values of aspartate aminotransferase and alanine aminotransferase in the group of the compounds of the present invention were apparently decreased compared to the group of SM102, which indicated that the toxicity of the compounds of the present invention was further reduced, suggesting that the compounds of the present invention possess higher biological safety.

Experimental Example 3: Delivery and Expression Effects of the Lipid Nanoparticle Compositions of the Present Invention Five balb/c mice (Zhejiang Vital River Laboratory Animal Technology Co., Ltd, female, 6-8 weeks old, 18-20 g) were taken as a group, labeled with a black marker pen on the tail with numbers 1 # to 5 #; five mice in each group were sequentially injected intramuscularly (IM) with 5 μg of the lipid nanoparticle composition. The lipid nanoparticle compositions of the present invention were prepared according to Test Example 1, in which Luciferase mRNA was encapsulated. An MC3 LNP group was set up in parallel as a reference (i.e., LNP formulation made from the known MC3 lipid, which was obtained by preparation according to the method and ratio of Test Example 1).

Fluorescence assay was performed for each group of mice at 24 hours after intramuscular administration of the samples (fluorescein sodium salt YEASEN,LOT:D5330150, IP, 150 mg/kg was administered 10 minutes in advance for each group). The mice were anesthetized, and then put into a small animal living optical imaging system-IVIS® Lumina LT Series III according to the orders from tail mark 1 # to 5 #. The whole-body fluorescence was detected to evaluate the delivery and the expression of the formulated Luciferase mRNA.

The delivery and expression effects of the LNPs of the compounds of the present invention are shown in FIG. 1, with the MC3 expression as a reference. The data show that the compounds of the present invention have excellent delivery and expression effects. Comparable or even superior delivery and expression effects over MC3 were achieved by the compounds of the present invention. In particular, the delivery and expression effects of Compound 2, Compound 2A, Compound 5, Compound 5A, Compound 5B, Compound 8, Compound 13, Compound 14, and Compound 20A were 3-4 times over MC3. From the results of Compound 2, 2A, Compound 5, Compound 5A and Compound 5B, the difference in configuration does not apparently affect the delivery activity of the ionizable lipids of the present invention.

Experimental Example 4: Assay of Extrahepatic Delivery Effect of Lipid Compounds of the Present Invention Five balb/c mice (Zhejiang Vital River Laboratory Animal Technology Co., Ltd, female, 6-8 weeks old, 18-20 g) were taken as a group, labeled with a black marker pen on the tail with numbers 1 # to 5 #; five mice in each group were sequentially injected intravenously with 20 μg of the lipid nanoparticle composition. The lipid nanoparticle compositions of the present invention were prepared according to Test Example 1, in which Luciferase mRNA was encapsulated. A phosphate buffered saline (PBS) group was set up in parallel as a blank control, and an MC3 group was set up as a reference (obtained by preparation according to the method and ratio of Test Example 1).

Fluorescence assay was performed for each group of mice at 24 hours after intravenous administration of the samples (fluorescein sodium salt YEASEN,LOT:D5330150, IP, 150 mg/kg was administered 10 minutes in advance for each group), the mice were anesthetized, and then put into a small animal living optical imaging system-IVIS® Lumina LT Series III according to the orders from tail mark 1 # to 5 #. The whole-body fluorescence was detected to evaluate the delivery and the expression of the prepared Luciferase mRNA.

At the end of the test, the mice were sacrificed by cervical dislocation, and the liver, spleen, stomach, and intestine tract were harvested, and the organs were discharged according to the corresponding positions from 1 # to 5 # for fluorescence detection of the organs.

As shown in FIGS. 2A-2D, the group of Compound 2A, Compound 5A, and Compound 13 of the present invention achieved significant extrahepatic delivery effects, and the extrahepatic delivery effects were significantly better than those of the group of MC3 and Compound 20A, which demonstrates that the compounds of the present invention possessed reduced toxicity of hepatic accumulation and improved extrahepatic delivery properties.

Experimental Example 5: Toxicity Assay

Animals were grouped according to body weight (five animals per group) one day before administration (Zhejiang Vital River Laboratory Animal Technology Co. Ltd, male, body weight: 170-220 g). The animals were weighed before administration, and lipid nanoparticle compositions based on Compound 2A, Compound 5A, Compound 13 or Compound 20A (prepared according to Test Example 1) of the present invention were administered intravenously in a single dose according to body weight. Luciferase mRNA was encapsulated in said lipid nanoparticle compositions. SM102 LNP, MC3 LNP (each prepared according to the method and ratio of Test Example 1) and phosphate buffered saline (PBS) were set up in parallel as a control group, respectively.

The administration volume is 10 mL/kg, and the administration dosage is 3 mg/kg.

Detecting frequency: non-anticoagulated blood was collected before administration and 24 hours after administration, the method of blood sampling as follows:

Non-anticoagulated blood was collected (the night before sampling, the mice were fasted overnight but ad libitum access to water, and fed following the completion of sampling), and the non-anticoagulated whole blood was allowed to stand at room temperature for 30 min, centrifuged at 5000 rpm for 5 min, serum (200 μL) was aspirated, and serum ALT (alanine aminotransferase) and AST (aspartate aminotransferase) were measured with an automated biochemical detector (Automated Bio-Chemical Detector 7060 Hitachi).

During the test, four rats in the MC3 group died and all five rats in Compound 20A group died.

Figure 3A:
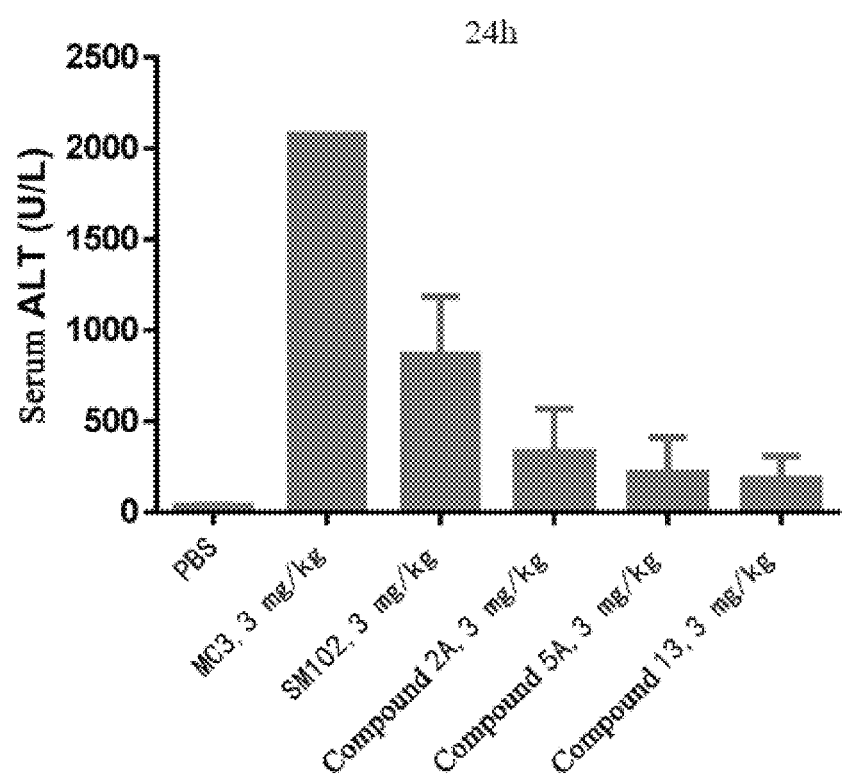
FIGS. 3A-3B shows the hepatic ALT/AST level of LNPs prepared based on the compounds of the present invention 24 h after intravenous injection.
Figure 3B:
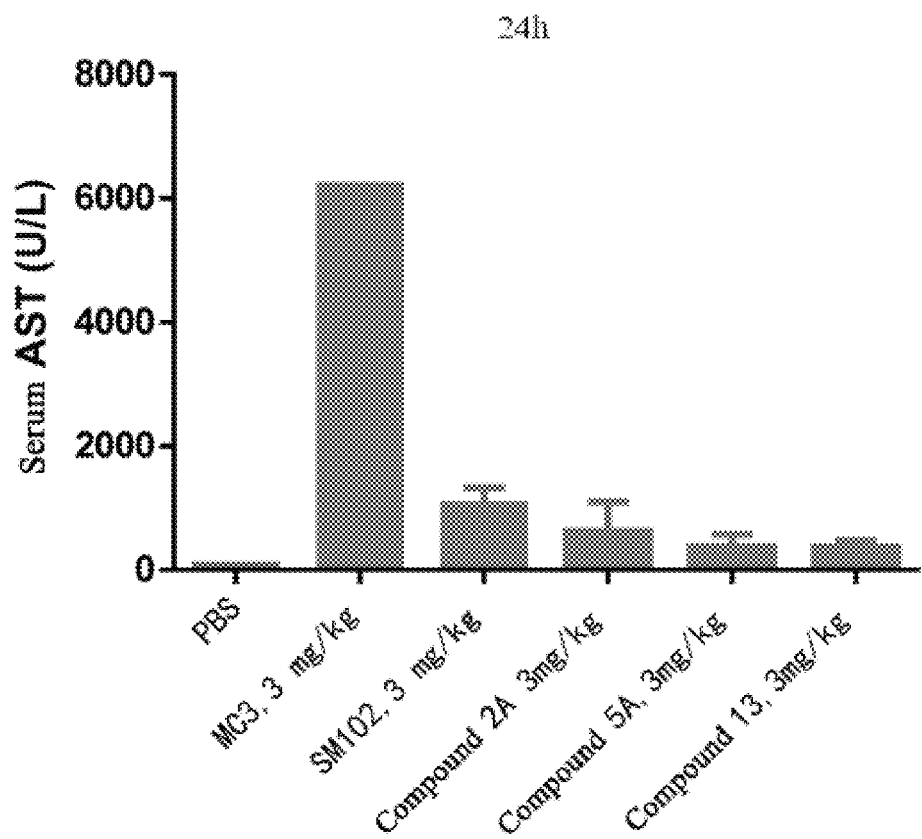

The results as shown in FIGS. 3A-3B showed that the aspartate aminotransferase and alanine aminotransferase values of the Compound 2A, Compound 5A and Compound 13 groups of the present invention were lower than those of the groups of the ionizable lipids MC3 and SM102 which are used for LNPs in the commercially available products respectively, which indicates that the compounds of the present invention have lower hepatotoxicity and higher biological safety.

While the above have been described in connection with embodiments of the present application, the present application is not to be limited by the foregoing specific embodiments and application fields. The foregoing specific embodiments are intended to illustrate but not limit the scope of the present disclosure. Multiple forms without departing from the claimed scope of the present application can be made by a person skilled in the art under the inspiration of the specification of the present application, which are within the claimed scope of the present application.

The invention claimed is:

1. A compound of formula (I), or a salt or a stereoisomer thereof,

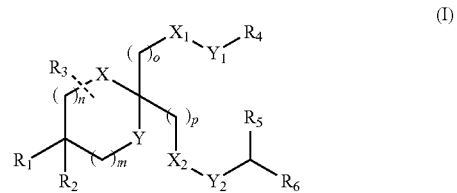

(I)

wherein
$R_1$ is

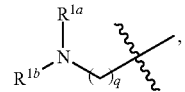

$R^{1a}$ and $R^{1b}$ are each independently —$CH_3$;
$R_2$ and $R_3$ are each independently H;
$R_4$ is C10, C11 or C12 linear alkyl;
$R_5$ and $R_6$ are identical and are selected from C6, C7 and C8 linear alkyl;
X and Y are each independently O;
$X_1$ and $X_2$ are independently selected from C=O and O, $Y_1$ and $Y_2$ are independently selected from C=O and O, with the proviso that $X_1$ and $Y_1$ are not both C=O or O, and $X_2$ and $Y_2$ are not both C=O or O;
m is 0, and n is 1;
o is 5 or 6;
p is 7 or 8, and
q is 2, 3 or 4.

2. The compound according to claim 1, or a salt or a stereoisomer thereof, wherein o is 6; and/or p is 7.

3. The compound according to claim 1, or a salt or a stereoisomer thereof,
the compound of formula (I) having the following structure of formula (IIA):

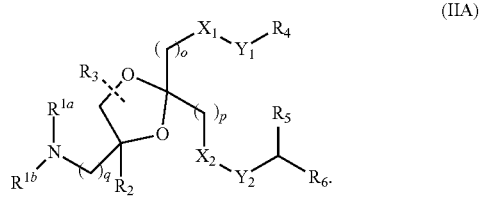

(IIA)

wherein;
$R^{1a}$ and $R^{1b}$ are each independently —$CH_3$;
$R_2$ and $R_3$ are each independently H;
$R_4$ is C10, C11 or C12 linear alkyl;
$R_5$ and $R_6$ are identical and are selected from C6, C7 and C8 linear alkyl;
$X_1$ and $X_2$ are both C=O, and $Y_1$ and $Y_2$ are both O; or $X_1$ is O, $Y_1$ is C—O, and $X_2$ is C—O, Y₂ is O;
o is 5 or 6;
p is 7; and
q is 2 or 3.

4. The compound according to claim 1, or a salt or a stereoisomer thereof,
the compound of formula (I) having a structure selected from:

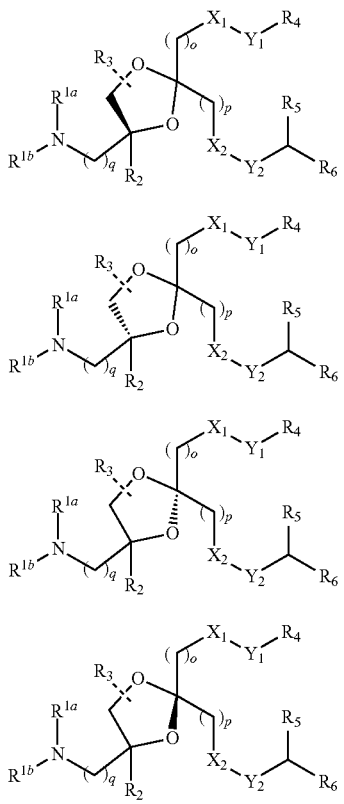

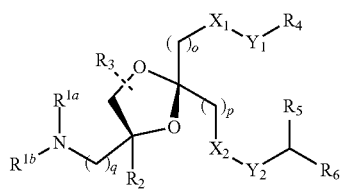

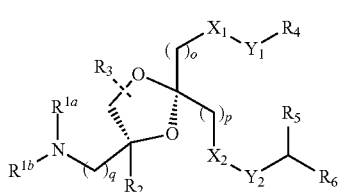

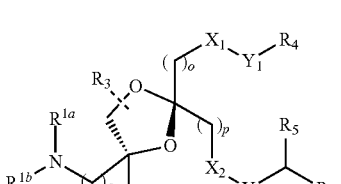

5. The compound according to claim 1, or a salt or a stereoisomer thereof,
wherein q is 2.

6. The compound according to claim 1, or a salt or a stereoisomer thereof,
wherein $X_1$ and $X_2$ are both C—O, and $Y_1$ and $Y_2$ are both O; or $X_1$ is O, $Y_1$ is C—O, and $X_2$ is C=O, $Y_2$ is O; or, $X_1$ is C=O, $Y_1$ is O, and $X_2$ is O, $Y_2$ is C=O.

7. The compound according to claim 1, or a salt or a stereoisomer thereof,
wherein $R_4$ is C10-C11 linear alkyl; and/or $R_5$ and $R_6$ are both C8 linear alkyl.

8. The compound according to claim 1, or a salt or a stereoisomer thereof,
wherein
o is 5, $R_4$ is C11 linear alkyl, p is 7, and $R_5$ and $R_6$ are both C8 linear alkyl, or
o is 6, $R_4$ is C10 linear alkyl, p is 7, and $R_5$ and $R_6$ are both C8 linear alkyl.

9. A compound, or a salt or a stereoisomer thereof, wherein the compound is selected from Compound 1

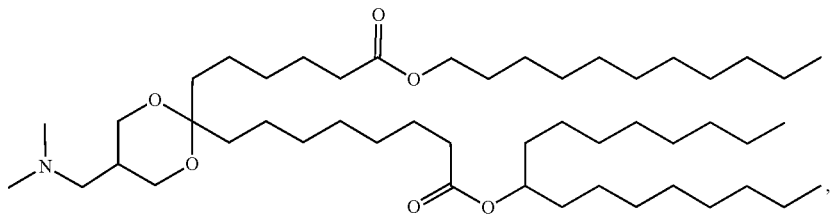

-continued
Compound 2
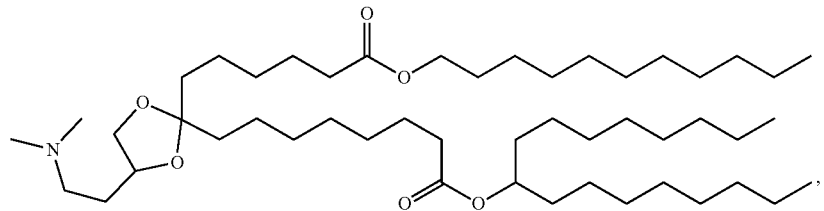
Compound 3
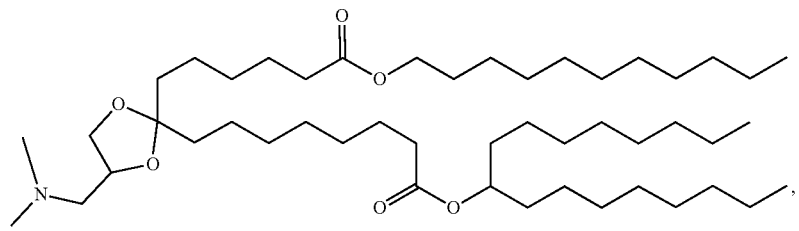
Compound 4
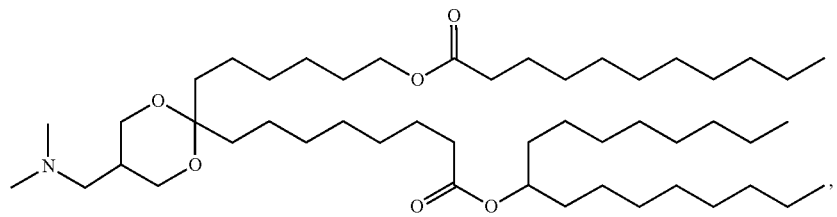
Compound 5
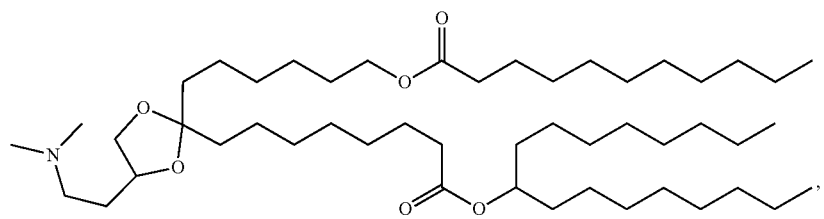
Compound 6
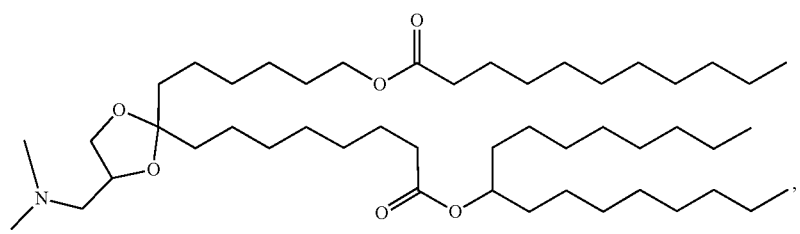
Compound 7
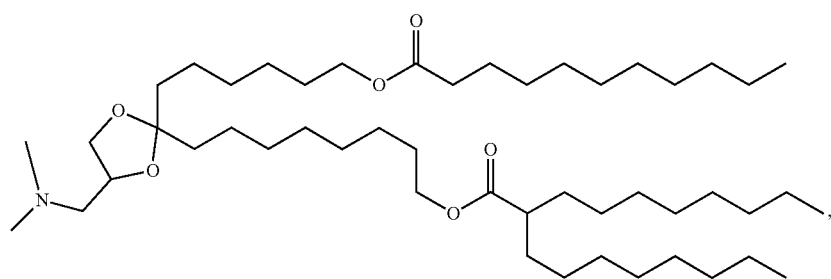

-continued
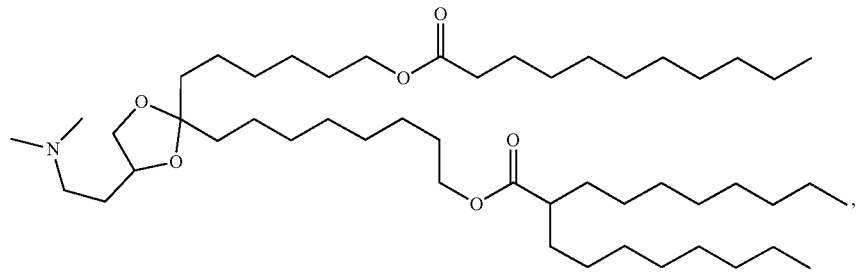
Compound 8
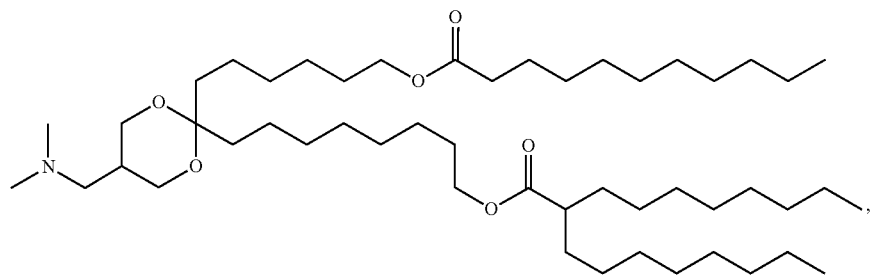
Compound 9
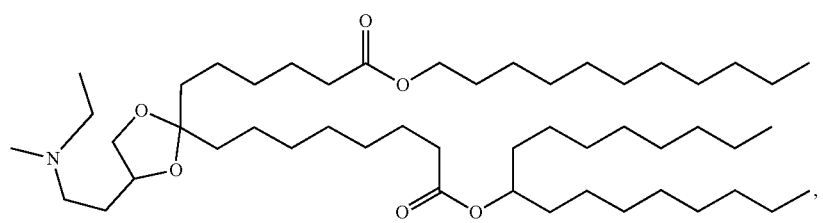
Compound 10
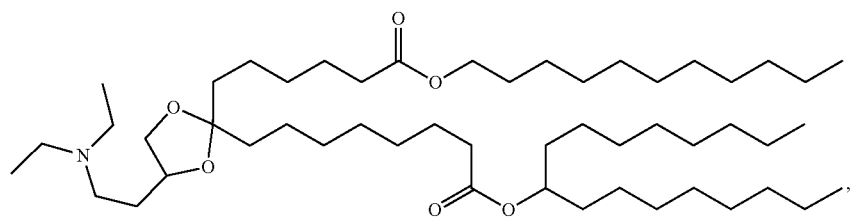
Compound 11
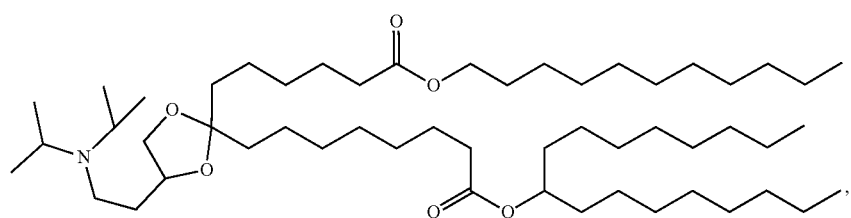
Compound 12
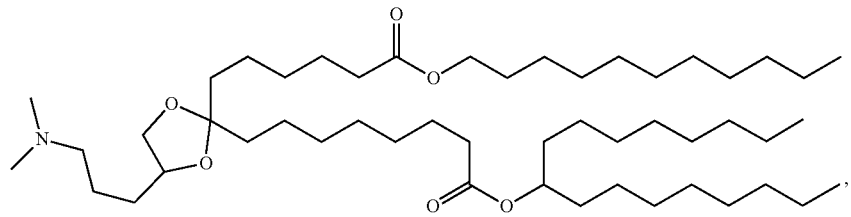
Compound 13

-continued
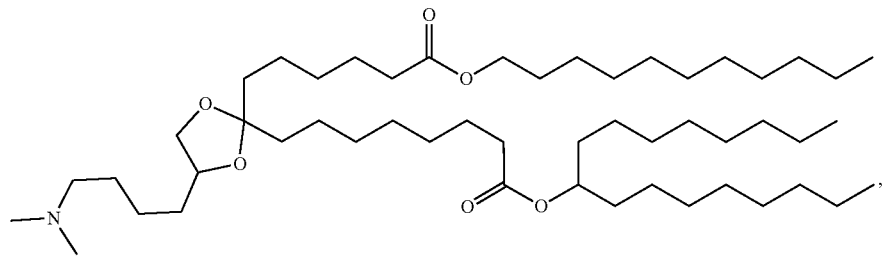
Compound 14
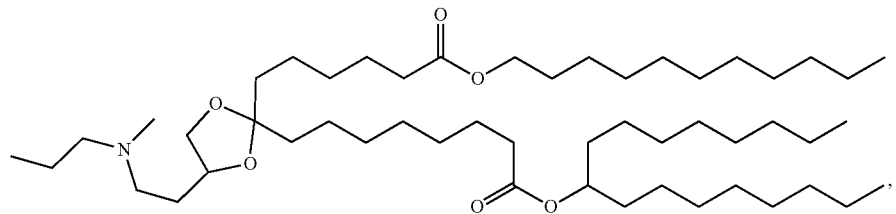
Compound 15
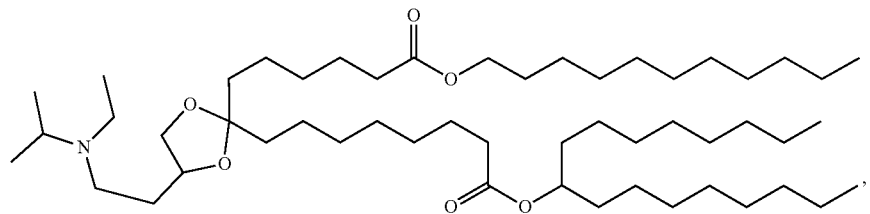
Compound 16
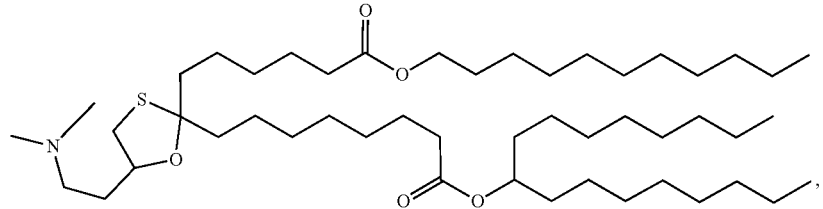
Compound 22
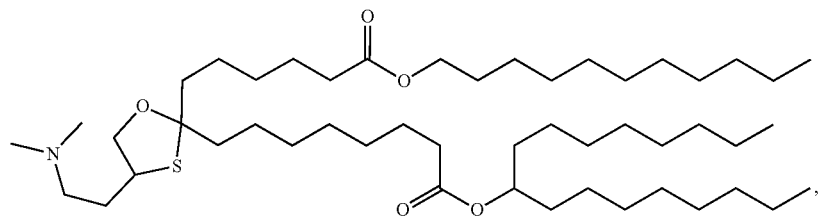
Compound 23
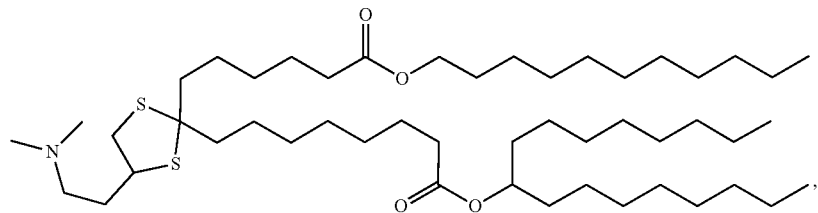
Compound 24

-continued
Compound 25
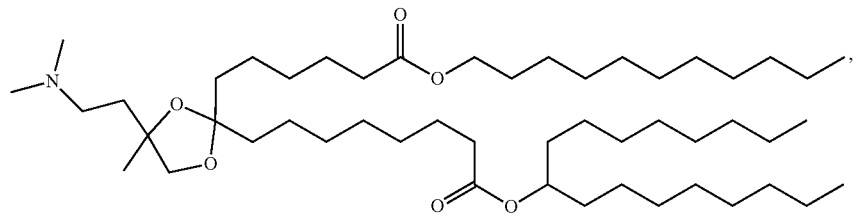
Compound 26
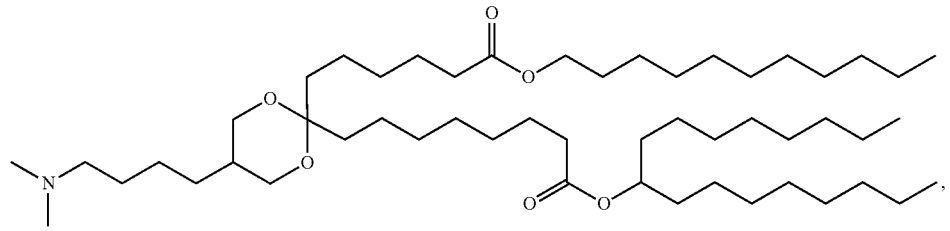
10. The compound according to claim 9 or a salt or a stereoisomer thereof,
wherein the compound is selected from:
Compound 2A
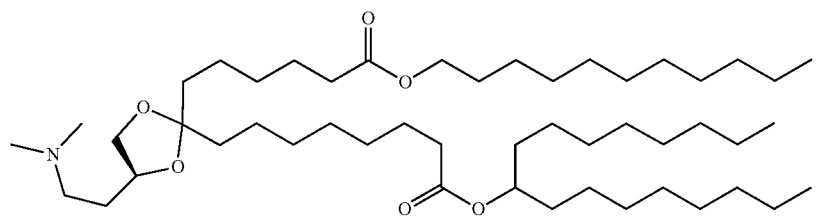
Compound 2B
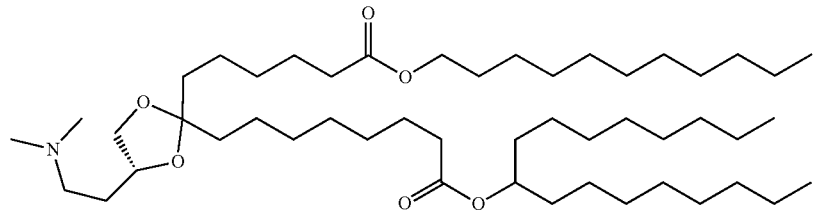
Compound 2C
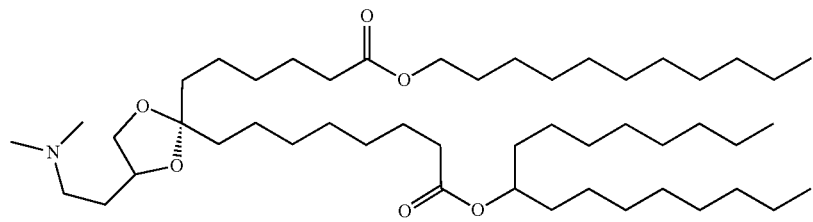
Compound 2D
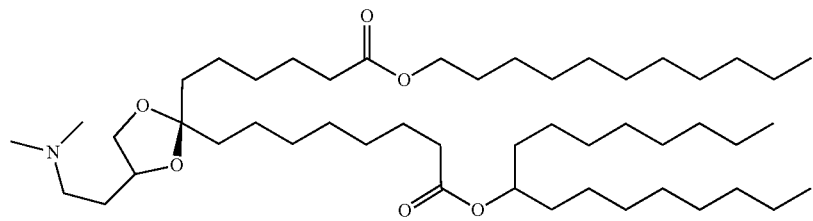

-continued
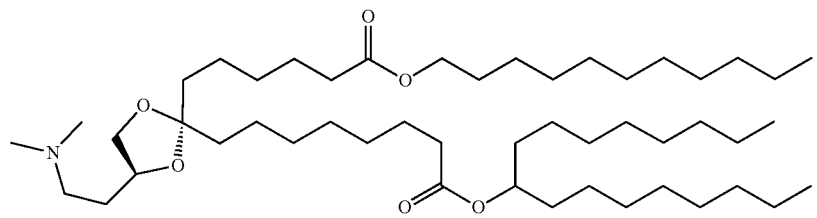
Compound 2E
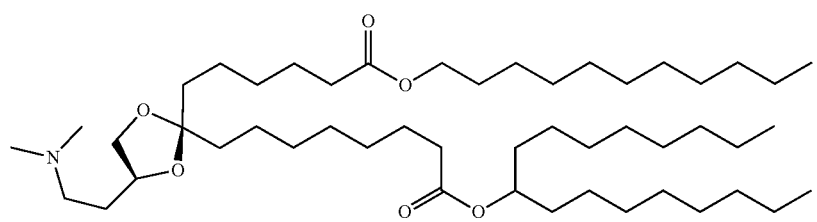
Compound 2F
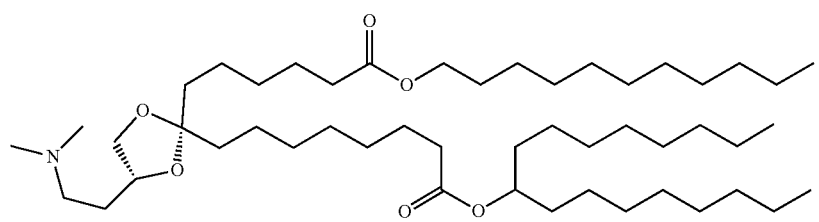
Compound 2G
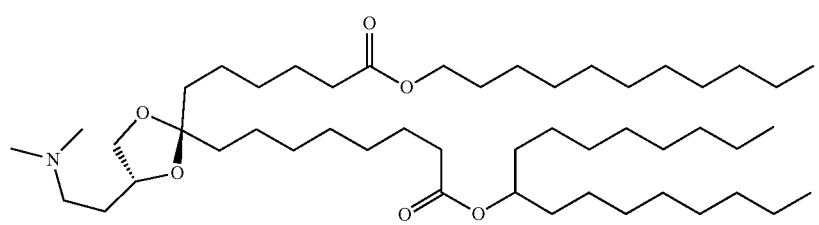
Compound 2H
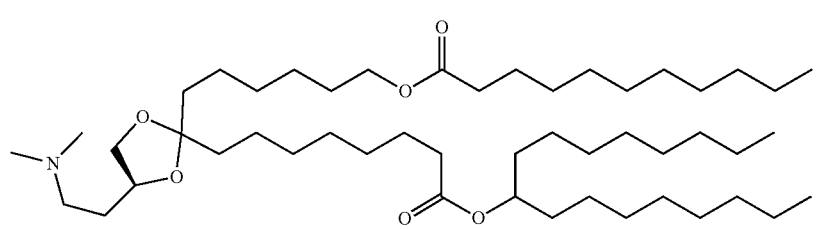
Compound 5A
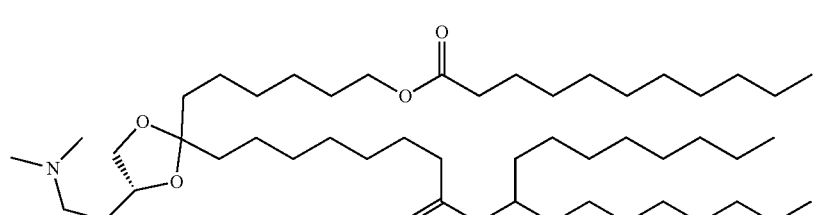
Compound 5B
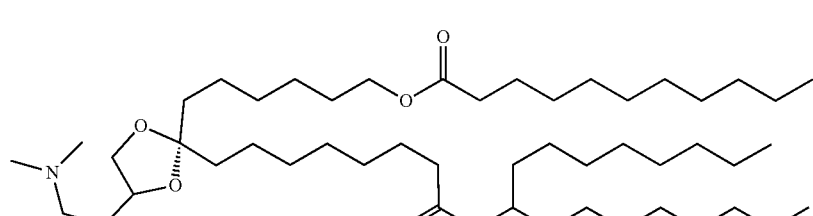
Compound 5C -continued
Compound 5D
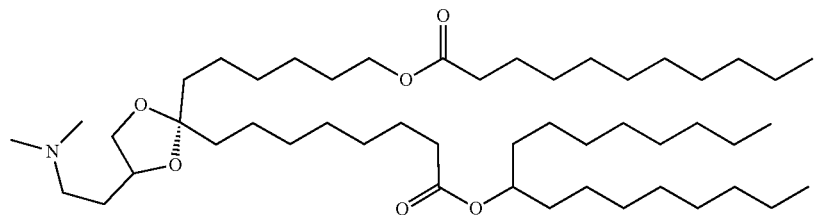
Compound 5E
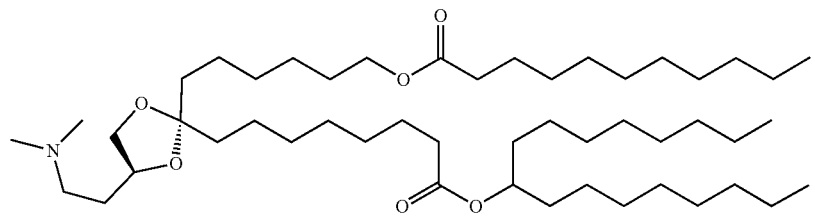
Compound 5F
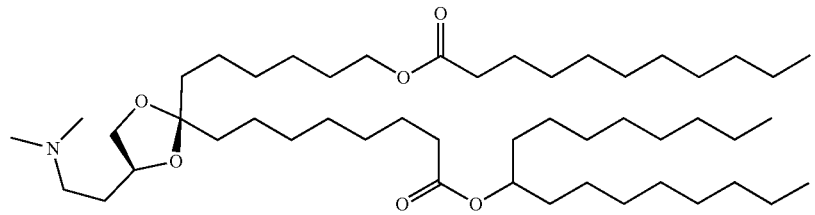
Compound 5G
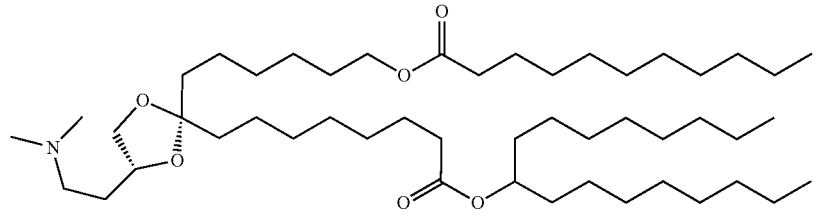
Compound 5H
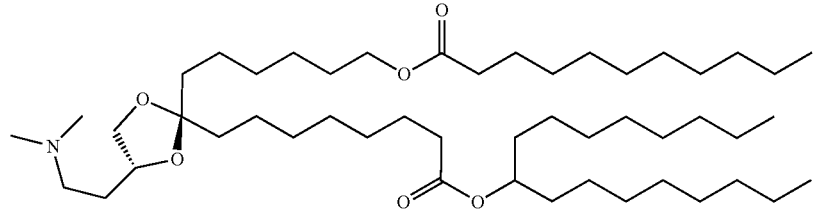
Compound 13A
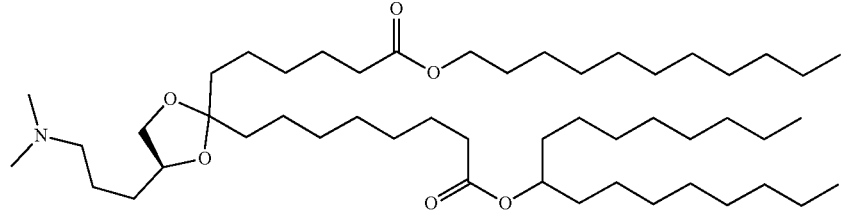
Compound 13B
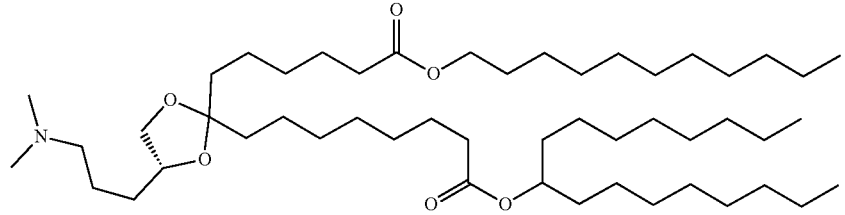

-continued

Compound 13C

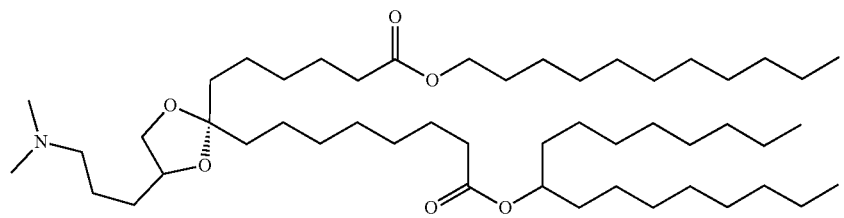

Compound 13D

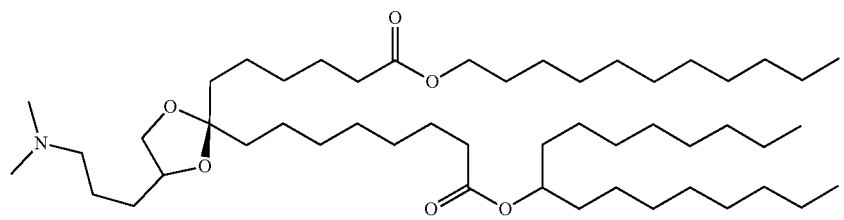

Compound 13E

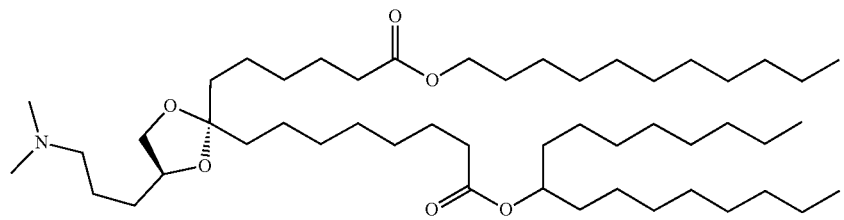

Compound 13F

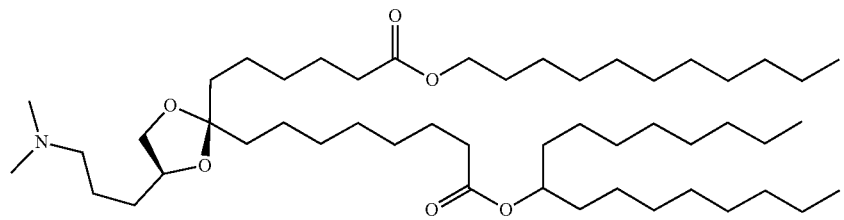

Compound 13G

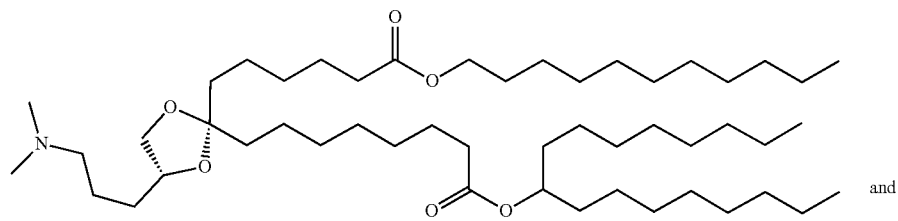

and

Compound 13H

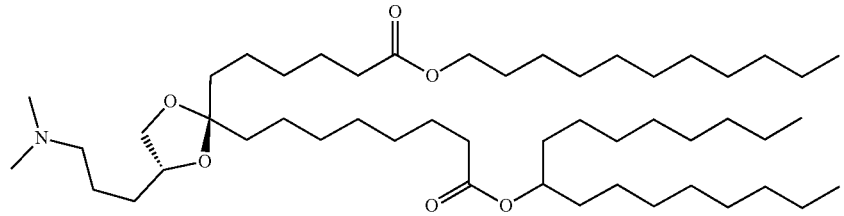

.

11. A nanoparticle composition comprising a lipid component which comprises a compound according to claim 1, or a salt or a stereoisomer thereof; said nanoparticle composition is lipid nanoparticle (LNP).

12. The nanoparticle composition according to claim 11, wherein said lipid component further comprises a phospholipid, a structural lipid and/or a PEG lipid;

wherein said phospholipid is optionally selected from one, two or more of the following compounds:
Dilauroyl lecithin (DLPC),
Dimyristoyl phosphatidylcholine (DMPC),
Dioleoyl lecithin (DOPC),
Dipalmitoyl phosphatidylcholine (DPPC),
Distearoyl phosphatidylcholine (DSPC), Dioleoyl phosphatidylcholine (DUPC),
Palmitoyl oleoyl phosphatidylcholine (POPC),
1,2-Di-O-octadecyl-sn-glycero-3-phosphocholine (18:0 Diether PC),
1-Oleoyl-2-cholesteryldimethylsuccinoyl-sn-glycero-3-phosphocholine (OChemsPC),
1-Hexadecyl-sn-glycero-3-phosphocholine (C16 Lyso PC),
1,2-Divinyl-sn-glycero-3-phosphocholine,
1,2-Diarylacyl-sn-glycero-3-phosphocholine,
1,2-Dioleoyl-sn-glycero-3 phosphorylethanolamine (DOPE),
1,2-Di-phytanoyl-sn-glycero-3-phosphoethanolamine (ME 16.0 PE),
1,2-Distearoyl-sn-glycero-3-phosphoethanolamine,
1,2-Diethenol-sn-glycero-3-phosphoethanolamine,
1,2-Divinyl-sn-glycero-3-phosphoethanolamine,
1,2-Diaryl-sn-glycero-3-phosphoethanolamine,
1,2-Dithiohexaenoate-sn-glycero-3-phosphoethanolamine,
1,2-dioleoyl-sn-glycero-3-phosphate-(1-glycerol) sodium salt (DOPG) or sphingomyelin,
  said structural lipid is optionally selected from one, two or more of cholesterol, coprosterol, sitosterol, ergosterol and stigmasterol; and/or
  said PEG lipid is optionally selected from one, two or more of PEG-modified phosphatidylethanolamine, PEG-modified phosphatidic acid, PEG-modified ceramide, PEG-modified dialkylamine, PEG-modified diacylglycerol or PEG-modified dialkylglycerol.

13. The nanoparticle composition according to claim 11, further comprising a therapeutic agent and/or a prophylactic agent, wherein said therapeutic and/or prophylactic agent is selected from vaccines, compounds capable of eliciting an immune response and nucleic acids,
  wherein the nucleic acid is optionally RNA, and said RNA is selected from one, two or more of siRNA, aiRNA, miRNA, dsRNA, shRNA or mRNA.

14. The nanoparticle composition according to claim 12, wherein said lipid component further comprises a phospholipid, a structural lipid and a PEG lipid; wherein said phospholipid is DOPE or DSPC, said structural lipid is cholesterol, and said PEG lipid is selected from PEG-modified phosphatidylethanolamine, PEG-modified phosphatidic acid, PEG-modified ceramide, PEG-modified dialkylamine, PEG-modified diacylglycerol and PEG-modified dialkylglycerol.

15. A pharmaceutical composition comprising the nanoparticle composition according to claim 13 and a pharmaceutically acceptable excipient.

16. A method of preparation of a lipid nanoparticle composition, comprising mixing the compound according to claim 1 or a salt or stereoisomer thereof with a phospholipid, structural lipid, and/or PEG lipid.

17. A method of delivering a therapeutic and/or prophylactic agent to a mammalian cell, comprising administering the nanoparticle composition according to claim 13 to a subject, wherein said administration comprises contacting the cell with said nanoparticle composition to deliver the therapeutic and/or prophylactic agent to the cell.

18. A method of delivering a therapeutic and/or prophylactic agent to a patient, comprising administering to a patient in need thereof the nanoparticle composition according to claim 13.

19. A method of introducing a nucleic acid into a cell, comprising contacting said cell with a nanoparticle composition according to claim 13.

20. A method of treating a disease or condition in a mammal, comprising administering a therapeutically or prophylactically effective amount of a nanoparticle composition according to claim 13 to the mammal; wherein said disease or condition is selected from infectious diseases, cancer and proliferative diseases, genetic diseases, autoimmune diseases, diabetes, neurodegenerative diseases, cardiovascular diseases, renal vascular diseases and metabolic diseases; and wherein the treating consists of achieving partial or complete response, alleviation, amelioration, or remission of said disease or condition, inhibiting progression of said disease or condition, reducing severity of said disease or condition and/or reducing incidence of one or more symptoms or signs thereof.

* * * * *

UNITED STATES PATENT AND TRADEMARK OFFICE
CERTIFICATE OF CORRECTION

| | |
|---|---|
| PATENT NO. | : 12,391,662 B2 |
| APPLICATION NO. | : 18/675317 |
| DATED | : August 19, 2025 |
| INVENTOR(S) | : Shan Cen et al. |

It is certified that error appears in the above-identified patent and that said Letters Patent is hereby corrected as shown below:

On the Title Page

Indicate the Assignee as:
(73) Assignee: RINUAGENE BIOTECHNOLOGY CO., LTD. (CN); RINUAGENE INTERNATIONAL HK LIMITED (CN)

In the Specification

In Columns 17 and 18, depict Compound 5A as:

" 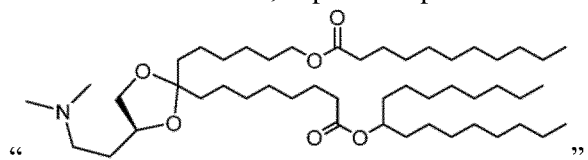 "

In Columns 19 and 20, depict Compound 5B as:

" 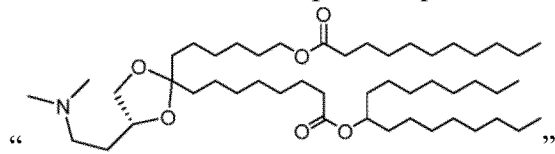 "

In Columns 19 and 20, depict Compound 5C as:

" 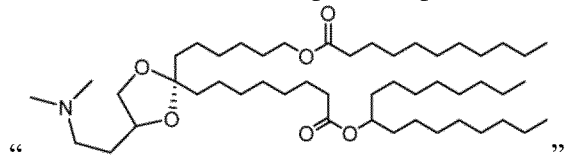 "

Signed and Sealed this
Seventh Day of October, 2025

John A. Squires
*Director of the United States Patent and Trademark Office*

CERTIFICATE OF CORRECTION (continued)
U.S. Pat. No. 12,391,662 B2

In Columns 19 and 20, depict Compound 5D as:

" 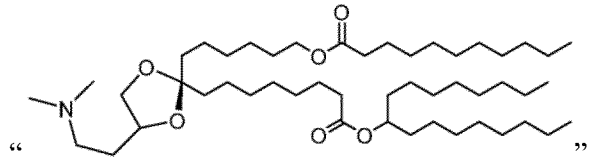 "

In Columns 19 and 20, depict Compound 5E as:

" 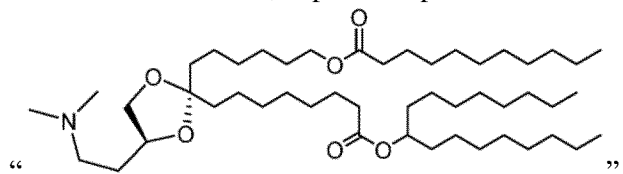 "

In Columns 19 and 20, depict Compound 5F as:

" 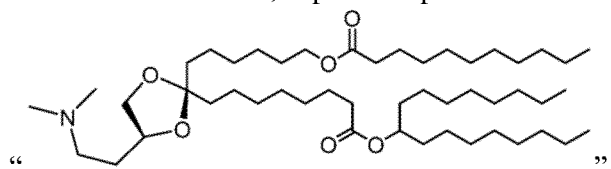 "

In Columns 19 and 20, depict Compound 5G as:

" 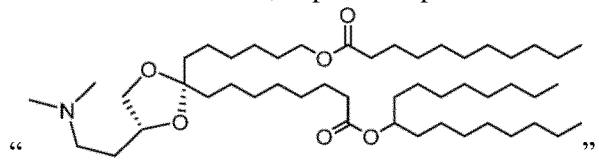 "

In Columns 19 and 20, depict Compound 5H as:

" 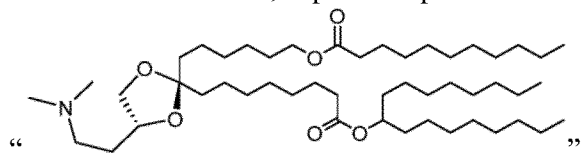 "

In the Claims

In Column 144, Line 67, Claim 3, replace "$Y_1$ is C–O, and $X_2$ is C–O," with "$Y_1$ is C=O, and $X_2$ is C=O,"

In Column 146, Line 34, Claim 6, replace "$X_1$ and $X_2$ are both C–O," with "$X_1$ and $X_2$ are both C=O,"

In Column 146, Line 35, Claim 6, replace "Y1 is C-O," with "Y1 is C=O,"

CERTIFICATE OF CORRECTION (continued)
U.S. Pat. No. 12,391,662 B2

In Columns 157 and 158, Claim 10, depict Compound 5D as:

" 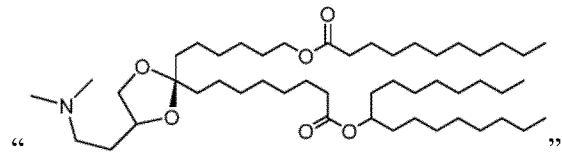 ,"